(12) United States Patent
Kim et al.

(10) Patent No.: US 10,900,043 B2
(45) Date of Patent: Jan. 26, 2021

(54) COMPOSITIONS AND METHODS FOR TREATING BACTERIAL DISEASE

(71) Applicants: ARIZONA BOARD OF REGENTS ON BEHALF OF THE UNIVERSITY OF ARIZONA, Tucson, AZ (US); THE HENRY M. JACKSON FOUNDATION FOR THE ADVANCEMENT OF MILITARY MEDICINE, INC., Bethesda, MD (US)

(72) Inventors: Won Jong Kim, Tucson, AZ (US); María Auxilio Rendón-Espinosa, Tucson, AZ (US); Magdalene Yh So, Tucson, AZ (US); Maira Goytia, Atlanta, GA (US); Ann Jerse, Bethesda, MD (US); Dustin Higashi, Notre Dame, IN (US)

(73) Assignees: ARIZONA BOARD OF REGENTS ON BEHALF OF THE UNIVERSITY OF ARIZONA, Tucson, AZ (US); THE HENRY M. JACKSON FOUNDATION FOR THE ADVANCEMENT OF MILITARY MEDICINE, INC., Bethesda, MD (US)

(*) Notice: Subject to any disclaimer, the term of this patent is extended or adjusted under 35 U.S.C. 154(b) by 0 days.

(21) Appl. No.: 16/411,856

(22) Filed: May 14, 2019

(65) Prior Publication Data
US 2019/0262374 A1 Aug. 29, 2019

Related U.S. Application Data

(63) Continuation-in-part of application No. 15/508,409, filed as application No. PCT/US2015/048114 on Sep. 2, 2015, now Pat. No. 10,286,016.

(60) Provisional application No. 62/691,146, filed on Jun. 28, 2018, provisional application No. 62/044,776, filed on Sep. 2, 2014.

(51) Int. Cl.
| | |
|---|---|
| A61K 39/095 | (2006.01) |
| C12N 15/70 | (2006.01) |
| A61K 35/74 | (2015.01) |
| A61K 9/00 | (2006.01) |
| C07K 14/22 | (2006.01) |
| A61K 9/06 | (2006.01) |
| A61P 15/00 | (2006.01) |

(52) U.S. Cl.
CPC ............ *C12N 15/70* (2013.01); *A61K 9/0034* (2013.01); *A61K 35/74* (2013.01); *A61K 39/095* (2013.01); *C07K 14/22* (2013.01); *A61K 9/06* (2013.01); *A61P 15/00* (2018.01)

(58) Field of Classification Search
None
See application file for complete search history.

(56) References Cited

U.S. PATENT DOCUMENTS

| 10,286,016 B2 * | 5/2019 | Kim ...................... A61K 45/06 |
| 2003/0026809 A1 | 2/2003 | Robinson et al. |
| 2009/0318382 A1 | 12/2009 | Ghigo et al. |
| 2011/0256232 A1 | 10/2011 | Nygaard et al. |

FOREIGN PATENT DOCUMENTS

| WO | 2003/006672 | 1/2003 |
| WO | 2006/036406 | 4/2006 |
| WO | 2011/077143 | 6/2011 |
| WO | 2014/078656 | 5/2014 |
| WO | 2014/121301 | 8/2014 |

OTHER PUBLICATIONS

Higashi et al. PLoS ONE 6: e21373: 1-7, 2011.*
So M. Tribal Warfare: Killing of pathogen N. gonorrhoeae by commensal N. elongata. Research Project, Grantome, 2015: https://www.grantome.com/grant/NIH/R21-AI111944-02.*
Aagaard, K., et al., "A Metagenomic Approach to Characterization of the Vaginal Microbiome Signature in Pregnancy" PLoS One, 2012. 7(6): p. e36466.
Berry, J.L., et al., "Functional Analysis of the Interdependence between DNA Uptake Sequence and Its Cognate ComP Receptor during Natural Transformation in *Neisseria* Species" PLoS Genet, 2013. 9(12): p. e1004014.
CartWright, K.A., et al., "The Stonehouse survey: nasopharyngeal carriage of meningococci and Neisseria lactamica." Epidemiol Infect, 1987. 99(3): p. 591-601.
Cascales, E., et al., "Colicin biology." Microbiol Mol Biol Rev, 2007. 71(1): p. 158-229.
Cole et al. "Opacity proteins increase Neisseria gonorrhoeae fitness in the female genital tract due to a factor under ovarian control." Infect Immun, 2010. 78(4): p. 1629-1641.
Dillard, J.P., "Genetic Manipulation of Neisseria gonorrhoeae." Curr Protoc in Microbiol, 2011(Chapter 4:Unit4A.2), 24 pages.
Gerbase, A., et al., "Global burden of Sexually Transmitted Diseases (excluding HIV) in the year 2000" Sex Transm Dis, 2000. 15, pp. 1-27.
Han, X.Y., T. Hong, and E. Falsen, J "*Neisseria bacilliformis* sp. nov. isolated from human infections." Clin Microbiol, 2006. 44(2): p. 474-479.
Hancock, V., M. Dahl, and P. Klemm, "Probiotic *Escherichia coli* strain Nissle 1917 outcompetes intestinal pathogens during biofilm formation." J Med Microbiol, 2010. 59(Pt 4): p. 392-399.

(Continued)

*Primary Examiner* — Sarvamangala Devi
(74) *Attorney, Agent, or Firm* — Casimir Jones, S.C.; Tanya A. Arenson

(57) ABSTRACT

The present invention relates to compositions and methods for preventing and/or treating bacterial disease (e.g., disease caused by *Neisseria* sp. such as gonorrhea). In particular, the present invention provides compositions comprising an effective amount of a nucleic acid, wherein such compositions are capable of killing or inhibiting the growth of a *Neisseria* sp. (e.g., *Neisseria gonorrhoeae*).

12 Claims, 22 Drawing Sheets

Specification includes a Sequence Listing.

(56) References Cited

OTHER PUBLICATIONS

Hobbs, M.M., et al., "Experimental Gonococcal Infection in Male Volunteers: Cumulative Experience with Neisseria gonorrhoeae Strains FA1090 and MS11mkC" Front Microbiol, 2011. 2:123; p. 1-12.

Howie, H.L., S.L. Shiflett, and M. So, "Extracellular signal-regulated kinase activation by Neisseria gonorrhoeae downregulates epithelial cell proapoptotic proteins Bad and Bim. Infection and immunity." Infect Immun, 2008. 76(6): p. 2715-2721.

International Search Report and Written Opinion, International Patent Application No. PCT/US2015/048114, dated Dec. 4, 2015.

Iwase, T., et al., "*Staphylococcus epidermidis* Esp inhibits *Staphylococcus aureus* biofilm formation and nasal colonization." Nature, 2010. 465(7296): p. 346-349.

Jerse, A.E., et al., "Estradiol-Treated Female Mice as Surrogate Hosts for Neisseria gonorrhoeae Genital Tract Infections." Front Microbiol, 2011. 2:107; pp. 1-13.

Johnson-Henry, K.C., et al., "Amelioration of the Effects of Citrobacter rodentium Infection in Mice by Pretreatment with Probiotics" J Infect Dis, 2005. 191(12): p. 2106-2117.

Knapp J.S., et al, "Prevalence and persistence of Neisseria cinerea and other *Neisseria* spp. in adults. J Clin Microbiol" J Clin Microbiol, 1988. 26(5): p. 896-900.

Krediet, C.J., et al., "Members of native coral microbiota inhibit glycosidases and thwart colonization of coral mucus by an opportunistic pathogen." ISME J, 2013. 7(5): p. 980-990.

Laga, M., et al., "Non-ulcerative sexually transmitted diseases as risk factors for HIV-1 transmission in women: results from a cohort study." Aids, 1993. 7(1): p. 95-102.

Makarova, K.S., Y.I. Wolf, and E.V. Koonin, "Comparative genomics of defense systems in archaea and bacteria." Nucleic Acids Res, 2013. 41(8): p. 4360-4377.

Maltby, R., et al., "Nutritional Basis for Colonization Resistance by Human Commensal *Escherichia coli* Strains HS and Nissle 1917 against *E. coli* O157:H7 in the Mouse Intestine" PLoS One, 2013. 8(1): p. e53957.

Marri, P.R., et al., "Genome Sequencing Reveals Widespread Virulence Gene Exchange among Human *Neisseria* Species" PLoS One, 2010. 5(7): p. e11835.

Merz, A.J. and M. So, "Interactions of pathogenic Neisseriae with epithelial cell membranes." Annu Rev Cell Dev Biol, 2000. 16: p. 423-457.

Miller, K., et al., "Isolation of Neisseria elongata and of Capnocytophaga ochracea from vaginal specimens" J Infect, 1985. 10(2): p. 174-175.

Packiam, M., et al., "Protective role of Toll-like receptor 4 in experimental gonococcal infection of female mice." Mucosal Immunol, 2012. 5(1): p. 19-29.

Peters, R.P., et al., "Screening of oropharynx and anorectum increases prevalence of Chlamydia trachomatis and Neisseria gonorrhoeae infection in female STD clinic visitors." Sex Transm Dis, 2011. 38(9): p. 783-787.

Poland, G.A., "Prevention of meningococcal disease: current use of polysaccharide and conjugate vaccines." Clin Infect Dis, 2010. 50 Suppl 2: p. S45-S53.

Ramsey, M.E., et al., "New complementation constructs for inducible and constitutive gene expression in Neisseria gonorrhoeae and Neisseria meningitidis." Appl Environ Microbiol, 2012. 78(9): p. 3068-3078.

Royce, R.A., et al., "Sexual transmission of HIV." N Engl J Med, 1997. 336(15): p. 1072-1078.

Simms, A.N. and A.E. Jerse, "In Vivo Selection for Neisseria gonorrhoeae Opacity Protein Expression in the Absence of Human Carcinoembryonic Antigen Cell Adhesion Molecules" Infect Immun, 2006. 74(5): p. 2965-2974.

Stephens, D.S., "Biology and pathogenesis of the evolutionarily successful, obligate human bacterium Neisseria menigitidis" Vaccine, 2009. 27 Suppl 2: p. B71-B77.

Swanson, J., "Studies on gonococcus infection. IV. Pili: their role in attachment of gonococci to tissue culture cells." J Exp Med, 1973. 137(3): p. 571-589.

Unemo, M. and W.M. Shafer, "Antibiotic resistance in Neisseria gonorrhoeae: origin, evolution, and lessons learned for the future." Ann N Y Acad Sci, 2011. 1230: p. E19-E28.

Warner, D.M., et al., "Regulation of the MtrC—MtrD—MtrE efflux-pump system modulates the in vivo fitness of Neisseria gonorrhoeae." J Infect Dis, 2007. 196(12): p. 1804-1812.

Warner, D.M., et al. "Clinically relevant mutations that cause derepression of the Neisseria gonorrhoeae MtrC—MtrD—MtrE Efflux pump system confer different levels of antimicrobial resistance and in vivo fitness." Mol Microbiol, 2008. 70(2): p. 462-478.

Whiley, D.M., et al., "The ticking time bomb: escalating antibiotic resistance in Neisseria gonorrhoeae is a public health disaster in waiting." J Antimicrob Chemother, 2012. 67(9): p. 2059-2061.

Wolfgang, M., et al., "The comP locus of Neisseria gonorrhoeae encodes a type IV prepilin that is dispensable for pilus biogenesis but essential for natural transformation." Mol Microbiol, 1999. 31(5): p. 1345-1357.

Wolfgang, W.J., et al., "*Neisseria oralis* sp. nov., isolated from healthy gingival plaque and clinical samples." Int J Syst Evol Microbiol, 2013. 63(Pt 4): p. 1323-1328.

Wu, H., et al. "A strain-specific catalase mutation and mutation of the metal-binding transporter gene mntC attenuate Neisseria gonorrhoeae in vivo but not by increasing susceptibility to oxidative killing by phagocytes." Infect Immun, 2009. 77(3): p. 1091-1102.

Wu, H.M., et al., "Emergence of ciprofloxacin-resistant Neisseria meningitidis in North America." N Engl J Med, 2009. 360(9): p. 886-892.

Xie, H., et al., "*Streptococcus cristatus* ArcA interferes with Porphyromonas gingivalis pathogenicity in mice." J Periodontal Res, 2012. 47(5): p. 578-583.

\* cited by examiner $*p < 0.01, **p < 0.001$

Colonization load of WT Ngo in mice inoculated with and without Nel

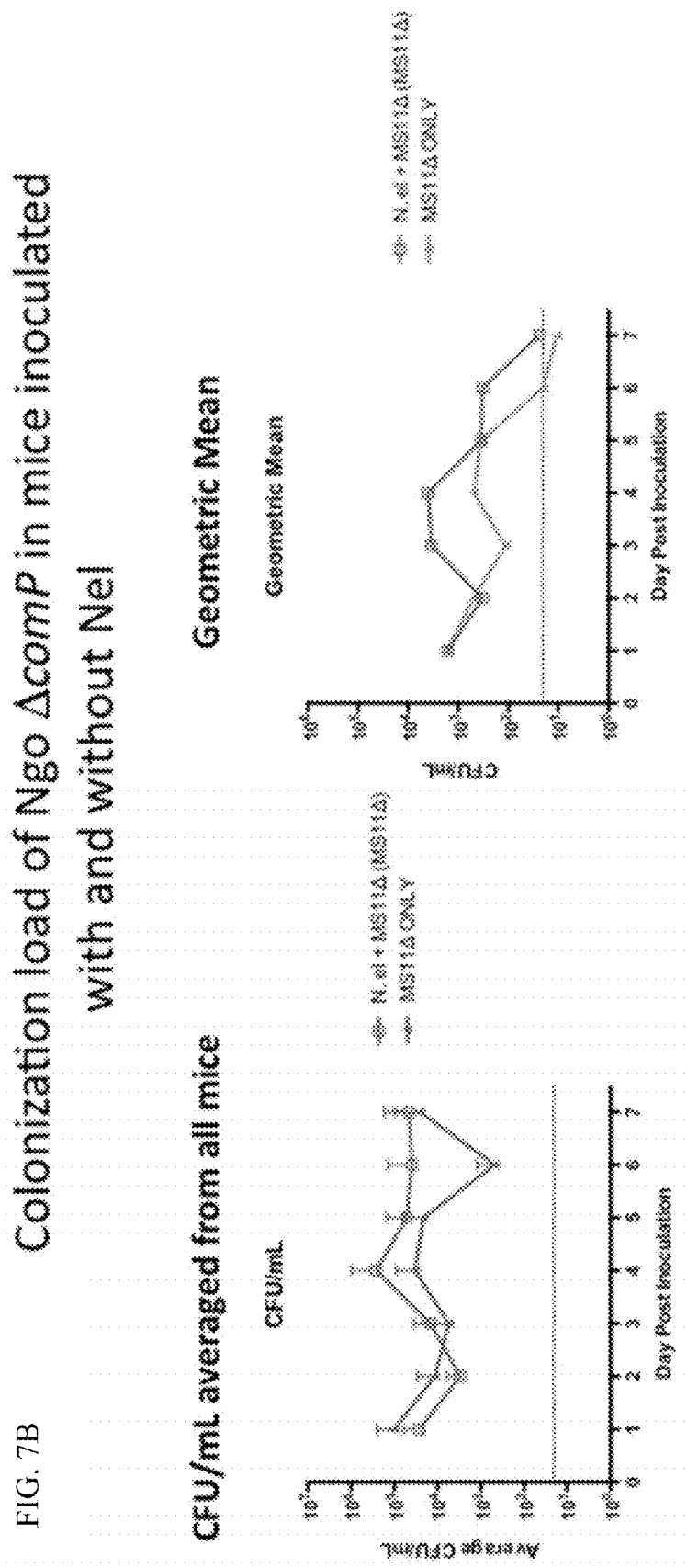
FIG. 7B  Colonization load of Ngo ΔcomP in mice inoculated with and without Nel

*P<0.005, **P<0.0001

**P<0.005

```
                            SEQUENCE LISTING

<160> NUMBER OF SEQ ID NOS: 39

<210> SEQ ID NO 1
<211> LENGTH: 12
<212> TYPE: DNA
<213> ORGANISM: Artificial
<220> FEATURE:
<223> OTHER INFORMATION: synthetic
<220> FEATURE:
<221> NAME/KEY: N
<222> LOCATION: (1)..(1)
<223> OTHER INFORMATION: N is A or T
<220> FEATURE:
<221> NAME/KEY: N
<222> LOCATION: (2)..(2)
<223> OTHER INFORMATION: N is T, G, or A
<220> FEATURE:
<221> NAME/KEY: N
<222> LOCATION: (3)..(3)
<223> OTHER INFORMATION: N is G or C
<220> FEATURE:
<221> NAME/KEY: N
<222> LOCATION: (4)..(4)
<223> OTHER INFORMATION: N is C or T
<220> FEATURE:
<221> NAME/KEY: N
<222> LOCATION: (5)..(5)
<223> OTHER INFORMATION: N is C, T, or A
<220> FEATURE:
<221> NAME/KEY: N
<222> LOCATION: (6)..(6)
<223> OTHER INFORMATION: N is G or A
<220> FEATURE:
<221> NAME/KEY: N
<222> LOCATION: (7)..(7)
<223> OTHER INFORMATION: N is T or C
<220> FEATURE:
<221> NAME/KEY: N
<222> LOCATION: (11)..(11)
<223> OTHER INFORMATION: N is C or A

<400> SEQUENCE: 1
nnnnnnnctg na                                                         12

<210> SEQ ID NO 2
<211> LENGTH: 12
<212> TYPE: DNA
<213> ORGANISM: Artificial
<220> FEATURE:
<223> OTHER INFORMATION: Synthetic
<220> FEATURE:
<221> NAME/KEY: N
<222> LOCATION: (2)..(2)
<223> OTHER INFORMATION: N is T or G

<400> SEQUENCE: 2
angccgtctg aa                                                         12

<210> SEQ ID NO 3
<211> LENGTH: 10
<212> TYPE: DNA
<213> ORGANISM: Artificial
<220> FEATURE:
<223> OTHER INFORMATION: Synthetic

<400> SEQUENCE: 3
gccgtctgaa                                                            10
```

```
<210> SEQ ID NO 4
<211> LENGTH: 6
<212> TYPE: DNA
<213> ORGANISM: Artificial
<220> FEATURE:
<223> OTHER INFORMATION: synthetic

<400> SEQUENCE: 4 rgcgcy                                                                    6

<210> SEQ ID NO 5
<211> LENGTH: 4
<212> TYPE: DNA
<213> ORGANISM: Artificial
<220> FEATURE:
<223> OTHER INFORMATION: synthetic

<400> SEQUENCE: 5 ggcc                                                                      4

<210> SEQ ID NO 6
<211> LENGTH: 6
<212> TYPE: DNA
<213> ORGANISM: Artificial
<220> FEATURE:
<223> OTHER INFORMATION: synthetic

<400> SEQUENCE: 6 ccgcgg                                                                    6

<210> SEQ ID NO 7
<211> LENGTH: 6
<212> TYPE: DNA
<213> ORGANISM: Artificial
<220> FEATURE:
<223> OTHER INFORMATION: synthetic

<400> SEQUENCE: 7 gccggc                                                                    6

<210> SEQ ID NO 8
<211> LENGTH: 6
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (3)..(4)
<223> OTHER INFORMATION: n is a, c, g, or t

<400> SEQUENCE: 8 ggnncc                                                                    6

<210> SEQ ID NO 9
<211> LENGTH: 14
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(11)
<223> OTHER INFORMATION: n is a, c, g, or t

<400> SEQUENCE: 9
```

```
gcannnnnnn ntgc                                                         14

<210> SEQ ID NO 10
<211> LENGTH: 11
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(8)
<223> OTHER INFORMATION: n is a, c, g, or t

<400> SEQUENCE: 10
gagnnnnnta c                                                            11

<210> SEQ ID NO 11
<211> LENGTH: 5
<212> TYPE: DNA
<213> ORGANISM: Artificial
<220> FEATURE:
<223> OTHER INFORMATION: synthetic

<400> SEQUENCE: 11 ggtga                                                                    5

<210> SEQ ID NO 12
<211> LENGTH: 5
<212> TYPE: DNA
<213> ORGANISM: Artificial
<220> FEATURE:
<223> OTHER INFORMATION: synthetic

<400> SEQUENCE: 12 ccacc                                                                    5

<210> SEQ ID NO 13
<211> LENGTH: 5
<212> TYPE: DNA
<213> ORGANISM: Artificial
<220> FEATURE:
<223> OTHER INFORMATION: synthetic

<400> SEQUENCE: 13 agaaa                                                                    5

<210> SEQ ID NO 14
<211> LENGTH: 5
<212> TYPE: DNA
<213> ORGANISM: Artificial
<220> FEATURE:
<223> OTHER INFORMATION: synthetic

<400> SEQUENCE: 14 tcacc                                                                    5

<210> SEQ ID NO 15
<211> LENGTH: 13
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(9)
<223> OTHER INFORMATION: n is a, c, g, or t

<400> SEQUENCE: 15
```
aacnnnnnng tcg                                                          13

<210> SEQ ID NO 16
<211> LENGTH: 4
<212> TYPE: DNA
<213> ORGANISM: Artificial
<220> FEATURE:
<223> OTHER INFORMATION: synthetic

<400> SEQUENCE: 16 gatc                                                                     4

<210> SEQ ID NO 17
<211> LENGTH: 5
<212> TYPE: DNA
<213> ORGANISM: Artificial
<220> FEATURE:
<223> OTHER INFORMATION: synthetic

<400> SEQUENCE: 17 ccwgg                                                                    5

<210> SEQ ID NO 18
<211> LENGTH: 1000
<212> TYPE: DNA
<213> ORGANISM: Artificial
<220> FEATURE:
<223> OTHER INFORMATION: synthetic

<400> SEQUENCE: 18
cggtttgggc gtggatacgc ctgaccacgc cgcgccgatt acttcgggcg caccgattgg        60
cgtactgcac ggcttccgca gctatctgat gcaggacgaa aacggccaag tcttggggac       120
gcactctgtt tccgcaggct tggattaccc cggcatcggc ccggaacaca gccatctgca       180
cgacatcaag cgcgtcgaat acaccgttgc caaagatgac gaagcactcg aagcctttga       240
cttgctctgc cgattcgagg gcatcatccc cgcgctcgaa tccagccacg ccgttgcttg       300
ggcggtgaaa aacgcgccga aaatgggtaa agaccaagtg attttggtca acctgtcggg       360
tcgcggcgac aaagacatca ataccgtggc gaaactcaaa ggcattgagc tgtagctttg       420
ttagtctgat aaaaatgccg tccgaagctt gagttcagac ggcattttat tttgctatga       480
atttggtatt gcgatcgcat gccgtctgaa ttagaaacga atctgtattt taattttgtcc      540 ggatttttgt ttttccaatt gttttccttt tgtaatactg ccatttacgt ttaatgtaac       600
attacggtac agtaacgcgg cgcctgctga atattgctgt tgattatctg ctttataggc       660
gaaggattta ccgcccacat tcacgccgcc tttgccataa ttggcaaagt aagctgcaga       720
taacaagggt tttacggtaa ggttgccgac tttaaaccga taagcaaaat ccagtccggc       780
cgttagtgtt tcactgccaa tagaacttac tttaacactg tcgtcaccca acttgtaatc       840
tgcagatgac aggcggctgt aacggatacc cgcactaggg acaatctcga attgattgat       900
tttcagcgta ttgcccaaag taaggccggt ttggatgctt gttcggttaa agtttgcttt       960
ttgctgcgtt tgtaaccggc ttctcaagct gcccgcacca                            1000

<210> SEQ ID NO 19
<211> LENGTH: 1000
<212> TYPE: DNA
<213> ORGANISM: Artificial
<220> FEATURE:
<223> OTHER INFORMATION: synthetic

<400> SEQUENCE: 19

```
tcgtgttgtt tgattttatc tgcaaattct tttttataga tattccattc ttgccatgat        60
ttttttccgt aacctgccca ataatcgtaa gttcccaaaa agacccattg atttttttgt       120
ttgtcaaaag caaatagtgg agagccgcta tcgcccaaca cgccgtaatt tgttaacgca       180
tcttgcgaaa gtgcttgttt aagttcttct gccgaatact gtttattatg attaccaaag       240
ccgatcaaac cttcggtatt cattgtttgg tcaatattaa tatctttata aggcgtacct       300
gcaatggcat aacgataggc ttgtgaaaga tcgcgcaaat cgtagccttt tcatttcct        360
tcttgatgat aaaccccttt tcataaact  aattgcctgc ccgcaccgat ctgacaaaa        420
gaggaaaaac ggtttttatc tttgtaggta tccaatccgc cgccggcatc agttggtgca       480
atcggtgcca atgccgtctg aagcgatcgc cttcggttac aaacttatta aaacgcgcca       540
tattataatc ttcgaggcgg cctaaattgc tcgcacccca agctttatgg ggttcatagt       600
tattttgttc gacaacgcgg tattcatttt ctttgtcggc tacatcatta tgaccgttgt       660
attggccgta ataaaagta  tggacttctg ctttggcgtg tttgacgctg acggcatatt       720
ggggatcgac taccgttgct atgcgtttgt tgacatctgc aacgctaaaa tcaatcatcg       780
gtacgttgga taatgcgttg ccgatgtttt gacctcgttt gttttttcact gataaatcgg      840
ttgcgccgac aaaaaatttg cctttgtttt ctgcaaagtc acggaatatt tgataatcga       900
catcgtctct caccaatgcc gcttctgagt atggcgtaag gcataggca  agaaagatgg       960
ataaggatat ggcgttaatt ttaaaacgtt tggctttcat                            1000
```

<210> SEQ ID NO 20
<211> LENGTH: 183
<212> TYPE: DNA
<213> ORGANISM: Artificial
<220> FEATURE:
<223> OTHER INFORMATION: synthetic

<400> SEQUENCE: 20

```
cgcccgcacc aaaaggcccc gccaaaccgg tgctgcctgc ggttaaaaaa tagagtggga        60
aatatgcata ctgctgaatg ggatagtaag tctgttcaaa gaaatatgtt gaataatctg       120
ttcttattgg aagtaaagta atgactgata atcgggggtt tctcgagggc ttgacacttt       180
atg                                                                    183
```

<210> SEQ ID NO 21
<211> LENGTH: 155
<212> TYPE: DNA
<213> ORGANISM: Artificial
<220> FEATURE:
<223> OTHER INFORMATION: synthetic

<400> SEQUENCE: 21

```
gatacggatc acgggtcata actataggct taatattaca cgattctcat tccatcaagg        60
cggaaaaccg cacaaatact gaaacactat cgatcgattt gtaaacaagc ctacttaagt       120
aacttgcagt catcgatgtt taaacttcag acggc                                 155
```

<210> SEQ ID NO 22
<211> LENGTH: 20
<212> TYPE: DNA
<213> ORGANISM: Artificial
<220> FEATURE:
<223> OTHER INFORMATION: synthetic

<400> SEQUENCE: 22
ccgtccattt cggtattcac                                          20

<210> SEQ ID NO 23
<211> LENGTH: 20
<212> TYPE: DNA
<213> ORGANISM: Artificial
<220> FEATURE:
<223> OTHER INFORMATION: synthetic

<400> SEQUENCE: 23
ttttcgattt cttcgctgtg                                          20

<210> SEQ ID NO 24
<211> LENGTH: 20
<212> TYPE: DNA
<213> ORGANISM: Artificial
<220> FEATURE:
<223> OTHER INFORMATION: synthetic

<400> SEQUENCE: 24
gtaaacatca atgcggcttc                                          20

<210> SEQ ID NO 25
<211> LENGTH: 20
<212> TYPE: DNA
<213> ORGANISM: Artificial
<220> FEATURE:
<223> OTHER INFORMATION: synthetic

<400> SEQUENCE: 25
ctcgaagcct ttgacttgct                                          20

<210> SEQ ID NO 26
<211> LENGTH: 19
<212> TYPE: DNA
<213> ORGANISM: Artificial
<220> FEATURE:
<223> OTHER INFORMATION: synthetic

<400> SEQUENCE: 26
caaaatgcgc caaatcaac                                           19

<210> SEQ ID NO 27
<211> LENGTH: 20
<212> TYPE: DNA
<213> ORGANISM: Artificial
<220> FEATURE:
<223> OTHER INFORMATION: synthetic

<400> SEQUENCE: 27
gggttcagtc ccaagtttga                                          20

<210> SEQ ID NO 28
<211> LENGTH: 20
<212> TYPE: DNA
<213> ORGANISM: Artificial
<220> FEATURE:
<223> OTHER INFORMATION: synthetic

<400> SEQUENCE: 28
gaaatcgccg aacacgttat                                          20

<210> SEQ ID NO 29
<211> LENGTH: 20
<212> TYPE: DNA

```
<213> ORGANISM: Artificial
<220> FEATURE:
<223> OTHER INFORMATION: synthetic

<400> SEQUENCE: 29
ccaatacgcc gacataatcc                                              20

<210> SEQ ID NO 30
<211> LENGTH: 20
<212> TYPE: DNA
<213> ORGANISM: Artificial
<220> FEATURE:
<223> OTHER INFORMATION: synthetic

<400> SEQUENCE: 30
tcgcgcacaa tcaaaatatc                                              20

<210> SEQ ID NO 31
<211> LENGTH: 20
<212> TYPE: DNA
<213> ORGANISM: Artificial
<220> FEATURE:
<223> OTHER INFORMATION: synthetic

<400> SEQUENCE: 31
acgcgtaaaa acttcggttg                                              20

<210> SEQ ID NO 32
<211> LENGTH: 36
<212> TYPE: DNA
<213> ORGANISM: Artificial
<220> FEATURE:
<223> OTHER INFORMATION: synthetic

<400> SEQUENCE: 32
atgccgtctg aagtacggca gtttaaggtt tacacc                            36

<210> SEQ ID NO 33
<211> LENGTH: 20
<212> TYPE: DNA
<213> ORGANISM: Artificial
<220> FEATURE:
<223> OTHER INFORMATION: synthetic

<400> SEQUENCE: 33
gtataggctg cgcaactgtt                                              20

<210> SEQ ID NO 34
<211> LENGTH: 18
<212> TYPE: DNA
<213> ORGANISM: Artificial
<220> FEATURE:
<223> OTHER INFORMATION: synthetic

<400> SEQUENCE: 34
tgtaaaacga cggccagt                                                18

<210> SEQ ID NO 35
<211> LENGTH: 17
<212> TYPE: DNA
<213> ORGANISM: Artificial
<220> FEATURE:
<223> OTHER INFORMATION: synthetic

<400> SEQUENCE: 35
caggaaacag ctatgac                                                 17
```

```
<210> SEQ ID NO 36
<211> LENGTH: 20
<212> TYPE: DNA
<213> ORGANISM: Artificial
<220> FEATURE:
<223> OTHER INFORMATION: synthetic

<400> SEQUENCE: 36
gcagctatct gatgcaggac                                             20

<210> SEQ ID NO 37
<211> LENGTH: 20
<212> TYPE: DNA
<213> ORGANISM: Artificial
<220> FEATURE:
<223> OTHER INFORMATION: synthetic

<400> SEQUENCE: 37
agcttgagaa gccggttaca                                             20

<210> SEQ ID NO 38
<211> LENGTH: 21
<212> TYPE: DNA
<213> ORGANISM: Artificial
<220> FEATURE:
<223> OTHER INFORMATION: synthetic

<400> SEQUENCE: 38
ttccattctt gccatgattt t                                           21

<210> SEQ ID NO 39
<211> LENGTH: 20
<212> TYPE: DNA
<213> ORGANISM: Artificial
<220> FEATURE:
<223> OTHER INFORMATION: synthetic

<400> SEQUENCE: 39
ttcttgccta tgcccttacg                                             20
```

COMPOSITIONS AND METHODS FOR TREATING BACTERIAL DISEASE

CROSS-REFERENCE TO RELATED APPLICATIONS

The present application claims the benefit of U.S. Provisional Patent Application No. 62/691,146, filed Jun. 28, 2018 and is a continuation-in-part of U.S. patent application Ser. No. 15/508,409, filed Mar. 2, 2017, now U.S. Pat. No. 10,286,016, which is a Section 371 U.S. national stage entry of International Patent Application No. PCT/US2015/048114, International Filing Date Sep. 2, 2015, which claims the benefit of U.S. Provisional Patent Application No. 62/044,776, filed Sep. 2, 2014, the contents of which are incorporated by reference in their entireties.

STATEMENT REGARDING FEDERALLY SPONSORED RESEARCH OR DEVELOPMENT

This invention was made with government support under Grant No. R21 AI111944, awarded by NIH. The government has certain rights in the invention.

FIELD OF THE INVENTION

The present invention relates to compositions and methods for preventing and/or treating bacterial disease (e.g., disease caused by *Neisseria* sp. such as gonorrhea). In particular, the present invention provides compositions comprising an effective amount of a nucleic acid, wherein such compositions are capable of killing or inhibiting the growth of a *Neisseria* sp. (e.g., *Neisseria gonorrhoeae*).

BACKGROUND

Gonorrhea, an important public health problem and the second most common notifiable disease in the United States, is a purulent infection of mucous membrane surfaces caused by the gram-negative diplococcus *Neisseria gonorrhoeae*. Although gonorrhea (known colloquially as the clap and the drip) is most frequently spread during sexual contact, it can also be transmitted from the mother's genital tract to the newborn during birth, causing opthalmia neonatorum and systemic neonatal infection.

In women, the cervix and urethra are the most common site of gonorrheal infections. *Neisseria gonorrhoeae* can also spread to other parts of the body to cause infections of the joints (gonococcal arthritis) and Fallopian tubes, which can result in Pelvic inflammatory disease (PID) and ectopic pregnancy. In men, *Neisseria gonorrhoeae* most often causes localized infections of the anterior urethra. In men and women, *Neisseria gonorrhoeae* infections increase susceptibility to human immunodeficiency virus (HIV) infection. Most commonly, the term gonorrhea refers to urethritis and/or cervicitis in a sexually active person.

Gonococcal infections following sexual and perinatal transmission are a major source of morbidity worldwide. In the developed world, where prophylaxis for neonatal eye infection is standard, the vast majority of infections follow genitourinary mucosal exposure.

Improved therapeutic options for treating gonorrhea and/or conditions involving *Neisseria gonorrhoeae* activity are needed.

SUMMARY OF THE INVENTION

Experiments conducted during the course of developing embodiments for the present invention demonstrated that *Neisseria elongata* (Nel) dramatically reduces *Neisseria gonorrhoeae* (Ngo) viability in vitro and in vivo. Specifically, Nel DNA was identified as a lethal agent. Indeed, it was shown that DNA purified from intact Nel cells as well as the Nel DNA in the growth medium were able to kill Ngo. It was concluded that Ngo is killed when it takes up Nel DNA, via its Type IV pilus (Tfp), and containing the DNA Uptake Sequence (DUS) that is present in multiple copies in all neisserial genomes. This conclusion is based on the following data: Ngo mutants deleted of DNA uptake genes comP, pilT and pilE (AcomP, ApilT, ApilE) are resistant to killing by Nel DNA, in contrast to the complemented strains, which are sensitive to DNA killing. comP encodes a protein on Tfp that binds the neisserial DUS, pilT to encode the Tfp motor protein that is required for taking up the DNA, and pilE to encode pilin (PilE), the structural protein of the Tfp fiber. N400, a Ngo strain not expressing recA, is also resistant to Nel DNA killing, while the N400 strain induced to express RecA is sensitive to DNA killing. The RecA enzyme is required to recombine incoming neisserial DNA into homologous regions in the Ngo genome. Ngo deleted of any one of these genes is not transformed by neisserial DNA. The conducted animal experiments are consistent with in vitro results. Wild type (WT) Ngo is cleared more quickly from mice when inoculated together with Nel, compared to WT Ngo inoculated alone into animals. In contrast, the Ngo DNA uptake mutant AcomP mutant is resistant to accelerated clearance from mice by Nel.

Further experiments demonstrated that Ngo is killed when it takes up and undergoes homologous recombination with the commensal genomic DNA (gDNA). gDNA purified from commensal *Neisseria* efficiently kills Ngo. In contrast, Ngo mutants lacking the ability to uptake DNA or undergo homologous recombination are not affected by commensal *Neisseria* gDNA. Further, it was demonstrated that the methylation state of any DNA, and the presence of the DUS, determine its toxicity. DNA modified to mimic the methylation pattern of Ngo gDNA became significantly less toxic. In addition, Ngo gDNA, normally harmless to itself, kills Ngo whan its methylation state is altered.

Accordingly, in certain embodiments, the present invention provides a method for the inhibition of bacterial growth and/or for the killing of a target bacterium, comprising the step of adding to the target bacterium a composition comprising an effective amount of a nucleic acid comprising at least one (e.g., 1, 2, 3, or more) DNA uptake sequence (DUS) and a methylation pattern different from the target bacterium (e.g., wherein at least a portion of the nucleic acid is derived from a commensal species of *Neisseria*), thereby inhibiting bacterial growth and/or killing the bacteria.

Further embodiments provide a method for treatment of a bacterial infection by a target bacterium in an individual in need thereof comprising the step of administering to the individual a composition comprising a therapeutically effective amount of a nucleic acid comprising at least one DNA uptake sequence (DUS) and a methylation pattern different from the target bacterium (e.g., wherein at least a portion of the nucleic acid is derived from a commensal species of *Neisseria*).

Certain embodiments provide a pharmaceutical composition comprising a nucleic acid comprising at least one DNA uptake sequence (DUS) and a methylation pattern different from a target bacterium and a pharmaceutically acceptable carrier. In some embodiments, at least a portion of the nucleic acid is derived from a commensal species of *Neisseria*.

Also provided is an article (e.g. condom or medical device) comprising the composition.

The present invention is not limited to a particular DUS. In some embodiments, the DUS has the sequence $N_1N_2N_3N_4N_5N_6N_7CTGN_8A$ (SEQ ID NO:1), wherein $N_1$ is A or T, N2 is T, G, or A, $N_3$ is G or C, $N_4$ is C or T, $N_5$ is C, T, or A, $N_6$ is G or A, $N_7$ is T or C, and $N_8$ is C or A. For example, in some embodiments, the DUS has the sequence A[T/G]GCCGTCTGAA (SEQ ID NO:2) or GCCGTCTGAA (SEQ ID NO:3).

The present invention is not limited to a particular length of nucleic acid. In some embodiments, the nucleic acid is 0.1-100 kb (e.g., approximately 0.1, 10, 50, or 100 kb) in length. In some embodiments, the nucleic acid is plasmid, a bacterial artificial chromosome, or genomic DNA.

In some embodiments, the methylation is cytosine methylation in CpG or GpC dinucleotides and/or adenine methylation. In some embodiments, the nucleic acid is produced in a microorganism (e.g., *E. coli*) that possesses a methylation system (e.g., cytosine or adenine methylation system) that results in different methylation that the target microorganism.

In some embodiments, the product or composition further comprises an agent that enhances DNA recombination in said target bacterium.

In some embodiments, the composition is a pharmaceutical composition. In some embodiments, the composition is an antibacterial composition selected from a preservative, an antiseptic, a disinfectant, an anti-fouling agent, or a medicament. In some embodiments, the antibacterial composition is a preservative in a food product, feed composition, beverage, cosmetics or pharmaceuticals. In some embodiments, the composition is a toothpaste or mouthwash or inhaler. In some embodiments, the composition is administered topically (e.g., as a vaginal gel, e.g., hydroxyethycellulose)).

The present invention is not limited to a particular target bacterium. In some embodiments, the target bacterium is *Neisseria gonorrhoeae* (Ngo) or *Neisseria meningitidis* (Nme).

The present disclosure is not limited to a particular commensal species of *Neisseria*. In some embodiments, the commensal species is a human-dwelling commensal species (e.g. including but not limited to *Neisseria elongata* (Nel) or *Neisseria polysaccharea* (Npo)).

In some embodiments, the composition is administered to a human being. In some embodiments, the composition is administered to an individual in need thereof by topical, enteral, parenteral, or inhaled administration. For example, in some embodiments, composition is delivered topically to a mucosal surface. In some embodiments, the composition is a gel.

In some embodiments, the composition is co-administered with one or more additional drugs (e.g., one or more antibiotics).

Additional embodiments are described herein.

BRIEF DESCRIPTION OF THE DRAWINGS

(FIG. 5A) Average colonization load of Ngo and Nel. CFU/ml: colony forming units. The difference in Ngo colonization load between mice inoculated with Ngo alone and mice inoculated with Ngo and Nel was statistically significant ($P<0.021$ repeated measures ANOVA). (FIG. 5B) Percent of mice colonized with Ngo in the presence or absence of Nel (measure of clearance). Kaplan Meier colonization curves showing faster clearance of Ngo from mice co-inoculated with Nel ($P\leq0.003$, log rank test).

(FIG. 6A) The vagina of mice were inoculated with WT Ngo alone or WT Ngo and Nel in a 50:50 ratio, and Ngo counts were measured over the course of 7 days. Percent of mice colonized with WT Ngo when Nel is present (orange line) or absent (red line). ($P=0.0333$ log rank test). (FIG. 6B) The vagina of mice were inoculated with Ngo ΔcomP alone or Ngo ΔcomP and Nel in a 50:50 ratio, and Ngo ΔcomP counts were measured over the course of 7 days. Percent of mice colonized with Ngo DcomP when Nel is present (brown line) or absent (green line). ($P=0.2509$ log rank test; not statistically significant.) These results indicate that the susceptibility of Ngo to Nel clearance from mice requires its ability to take up neisserial DNA.

FIGS. 7A and 7B show the colonization load data (number of viable bacteria) recovered from the inoculated mice described in FIG. 6*a*. FIG. 7A shows the number of WT Ngo MS11 recovered from mice inoculated with or without Nel; FIG. 7B shows the number of Ngo MS11 ΔcomP recovered from mice inoculated with or without Nel. The data are expressed as Colony Forming Units/mL (CFU/mL) averaged for all mice (left), and as the Geometric Mean of the bacterial counts (right).

(FIG. 12A) Ngo CFUs recovered after a 5 h incubation with cell-free Nel supernates (SN) harvested at the indicated times from liquid cultures. n=3. Error bars: SEM. ($P<0.005$, *$P<0.0001$; One-way ANOVA with Tukey's Multiple Comparison Test). (FIG. 12B) A representative agar plate from a spot assay used to identify the toxic component in cell-free Nel supernates. (FIG. 12C) CFUs of Ngo recovered after a 4 h incubation with purified Nel DNA at the indicated final concentrations.

(FIG. 14A) WT Ngo CFUs. (FIG. 14B) Nel CFUs (FIG. 14C) Ngo ΔcomP. n=8 mice/group. (Log-rank test).

(FIG. 15A) CFUs of Ngo recovered after a 4 h incubation with Nel chromosomal DNA and DNA from plasmids pCR-Blunt and pCR-Blunt (DUS) replicated in *E. coli* DH5α (5 µg/mL). (FIG. 15B) CFUs of Ngo recovered after a 4 h incubation with Nel or Ngo DNA at the final concentrations indicated. (FIG. 15C) CFUs of Ngo recovered after a 4 h incubation with DNA (5 µg/mL) from *E. coli* and the *Neisseria* species indicated. Nla: *N. lactamica*, Nci: *N. cinerea*, Nmu: *N. mucosa*, Nsi: *N. sicca*, Npo: *N. polysacharea*, and Nme: *N. meningitidis*. n=3. LOD: 10 CFUs. (FIG. 15D) CFUs of Ngo recovered after a 4 h incubation with 5 µg/mL of unmodified Nel DNA or Nel DNA whose cytosines were methylated at GpC and CpG sequences using M.CviPI and M.SssI methyltransferases (Nel DNAm). (FIG. 15E) Ngo WT and TD3 DNA digested with HaeIII, NgoIV, and NlaIV restriction enzymes that cleave unmethylated GGCC, GCCGGC, and GGNNCC sequences, respectively. (FIG. 15F) CFUs of Ngo recovered after a 4 h incubation with (left to right) Nel chromosomal DNA (20 µg/mL), ADIDA replicated in Ngo i35A, and ADIDA replicated in *E. coli* (1 µg/mL each). Percent survival was calculated as noted.

DETAILED DESCRIPTION

Figure 1:
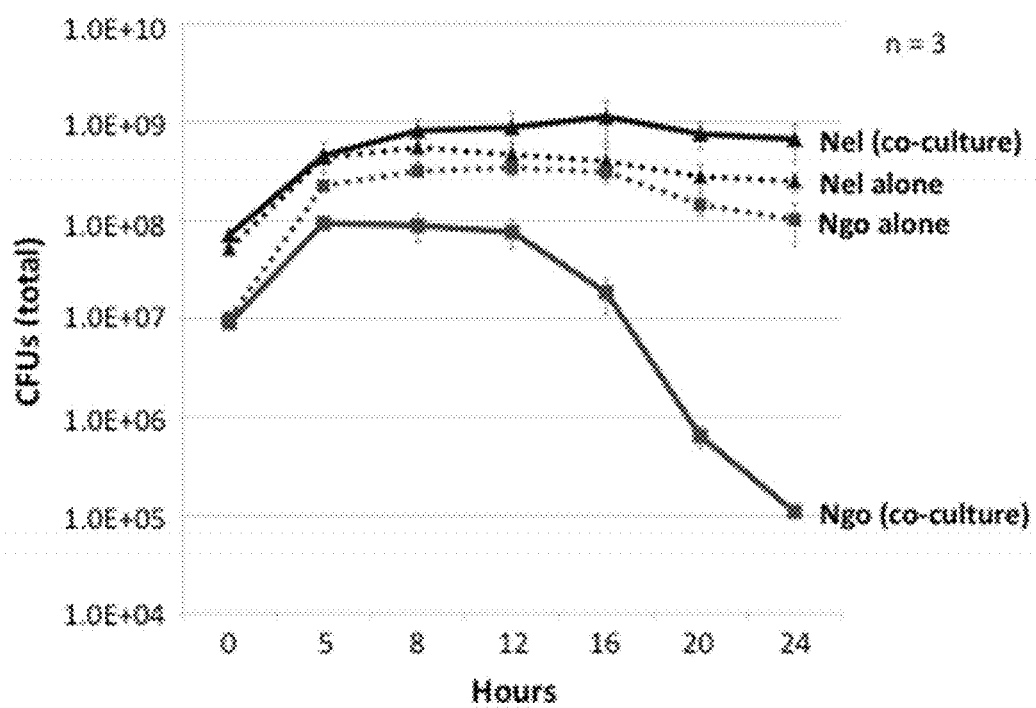
FIG. 1 shows Nel reduces the viability of Ngo during co-culture in vitro. Values and SEM were calculated from three independent experiments.

At least 16 species of *Neisseria* have been isolated from humans (e.g., *N. bacilliformis*, *N. cinerea*, *N. denitrificans*, *N. elongata*, *N. flavescens*, *N. gonorrhoeae*, *N. lactamica*, *N. macacae*, *N. meningitidis*, *N. mucosa*, *N. pharyngis*, *N. polysacharea* (Npo), *N. sicca*, *N. subflava*). Two of these are pathogens, *Neisseria gonorrhoeae* (Ngo) and *Neisseria meningitidis* (Nme); the others are commensals that form part of the normal flora (see, e.g., Knapp, J. S. et al, J Clin Microbiol, 1988. 26(5): p. 896-900; Wolfgang, W. J., et al., Int J Syst Evol Microbiol, 2013. 63(Pt 4): p. 1323-8) (e.g., *Neisseria bacilliformis*, *Neisseria cinerea*, *Neisseria elongata*, *Neisseria flavescens*, *Neisseria lactamica*, *Neisseria mucosa*, *Neisseria polysacharea*, *Neisseria sicca*, *Neisseria subflava*, *Neisseria flava*). 106 million new cases of gonorrhea occur each year, worldwide (see, e.g., Gerbase, A., et al., Sex Transm Dis, 2000. 15). Ngo primarily causes urogenital tract (UGT) infections; it is also found in the oropharynx of patients or partners of patients with UGT gonorrhea (see, e.g., Hobbs, M. M., et al., Front Microbiol, 2011. 2: p. 123; Peters, R. P., et al., Sex Transm Dis, 2011. 38(9): p. 783-7). Persistent infection can lead to such serious complications as salpingitis, pelvic inflammatory disease and ectopic pregnancy. There is a strong epidemiological link between gonorrhea and HIV/AIDs (see, e.g., Laga, M., et al., Aids, 1993. 7(1): p. 95-102; Royce, R. A., et al., N Engl J Med, 1997. 336(15): p. 1072-8). Antibiotics are the mainstay of infection control, as vaccine development is hampered by antigenic variation of bacterial surface components (see, e.g., Hobbs, M. M., et al., Front Microbiol, 2011. 2: p. 123). However, Ngo has acquired resistance to all antibiotics recommended for its treatment, and it is now considered a "ticking time bomb" (see, e.g., Whiley, D. M., et al., J Antimicrob Chemother, 2012. 67(9): p. 2059-61; Unemo, M. and W. M. Shafer, Ann N Y Acad Sci, 2011. 1230: p. E19-28). Nme asymptomatically colonizes the upper respiratory tract and causes disease when it crosses the epithelial and/or endothelial barriers (see, e.g., Stephens, D. S., Vaccine, 2009. 27 Suppl 2: p. B71-7). Infection is often fatal unless treated quickly with antibiotics. Vaccines have dramatically lowered the incidence of Nme infection (see, e.g., Poland, G. A., Clin Infect Dis, 2010. 50 Suppl 2: p. S45-53). As these vaccines do not protect against all serogroups, efforts to improve coverage are ongoing.

Commensal species of *Neisseria* receive little attention because they rarely cause disease. Currently, PubMed lists 294 publications on these organisms, and >20,000 on Ngo and Nme. Commensal *Neisseria* are known to colonize the oropharynx (see, e.g., Knapp, J. S. et al, J Clin Microbiol, 1988. 26(5): p. 896-900; Han, X. Y., T. Hong, and E. Falsen, J Clin Microbiol, 2006. 44(2): p. 474-9; Cartwright, K. A., et al., Epidemiol Infect, 1987. 99(3): p. 591-601); they also colonize other sites, including the vagina (see, e.g., Miller, K., et al., J Infect, 1985. 10(2): p. 174-5; Aagaard, K., et al., PLoS One, 2012. 7(6): p. e36466). Widespread horizontal gene transfer (HGT) has occurred among commensal and pathogenic *Neisseria* (see, e.g., Wu, H. M., et al., N Engl J Med, 2009. 360(9): p. 886-92; Marri, P. R., et al., PLoS One, 2010. 5(7): p. e11835), supporting the epidemiological evidence that these two groups of bacteria can inhabit similar niches. Whether they interact with each other when in proximity is unknown.

Some commensal bacteria have the ability to inhibit pathogen colonization. In mouse models of infection, *Lactobacillus rhamnosum* and *Lactobacillus acidophilus* reduce *Citrobacter rodentium* colonization in the gut (see, e.g., Johnson-Henry, K. C., et al., J Infect Dis, 2005. 191(12): p. 2106-17). *Streptococcus cristatus* attenuates *Porphyromonas gingivalis* colonization in the oral cavity (see, e.g., Xie, H., et al., J Periodontal Res, 2012. 47(5): p. 578-83); and *E. coli* biotype Nissle 1917, which has been used as a probiotic in Europe since the 1920s, prevents *E. coli* O157:H7 colonization in the gut (see, e.g., Maltby, R., et al., PLoS One, 2013. 8(1): p. e53957). In vitro, Nissle 1917 outperforms and outcompetes pathogenic *E. coli* in biofilm formation (see, e.g., Hancock, V., M. Dahl, and P. Klemm, J Med Microbiol, 2010. 59(Pt 4): p. 392-9). *Streptococcus epidermidis* is also better at forming biofilms than *Streptococcus aureus*, and secretes a protease that dissolves pathogen biofilms, rendering the bacteria more susceptible to antibiotics (see, e.g., Iwase, T., et al., Nature, 2010. 465(7296): p. 346-9). Environmental microbes also exhibit such antagonistic behavior. Commensal *Exiguobacterium* spp inhibits colonization of coral by opportunist *Serratia marcescens* (see, e.g., Krediet, C. J., et al., ISME J, 2013. 7(5): p. 980-90). The mechanisms by which commensals inhibit pathogen colonization are largely unknown; there is much interest in identifying these mechanisms because of the implications for therapy.

Experiments conducted during the course of developing embodiments for the present invention involved in vitro and in vivo approaches to determine whether the commensal, *Neisseria elongata* (Nel), antagonizes pathogen Ngo. Nel was found to dramatically reduce the viability of one lab strain and three recent clinical isolates of Ngo in vitro. Strikingly, the susceptibilty of Ngo to killing by Nel required its uptake of Nel genomic DNA. Experiments using the mouse model for Ngo colonization and persistence replicated this in vitro antagonistic behavior: Ngo is cleared from mice more rapidly when Nel is present.

Figure 2:
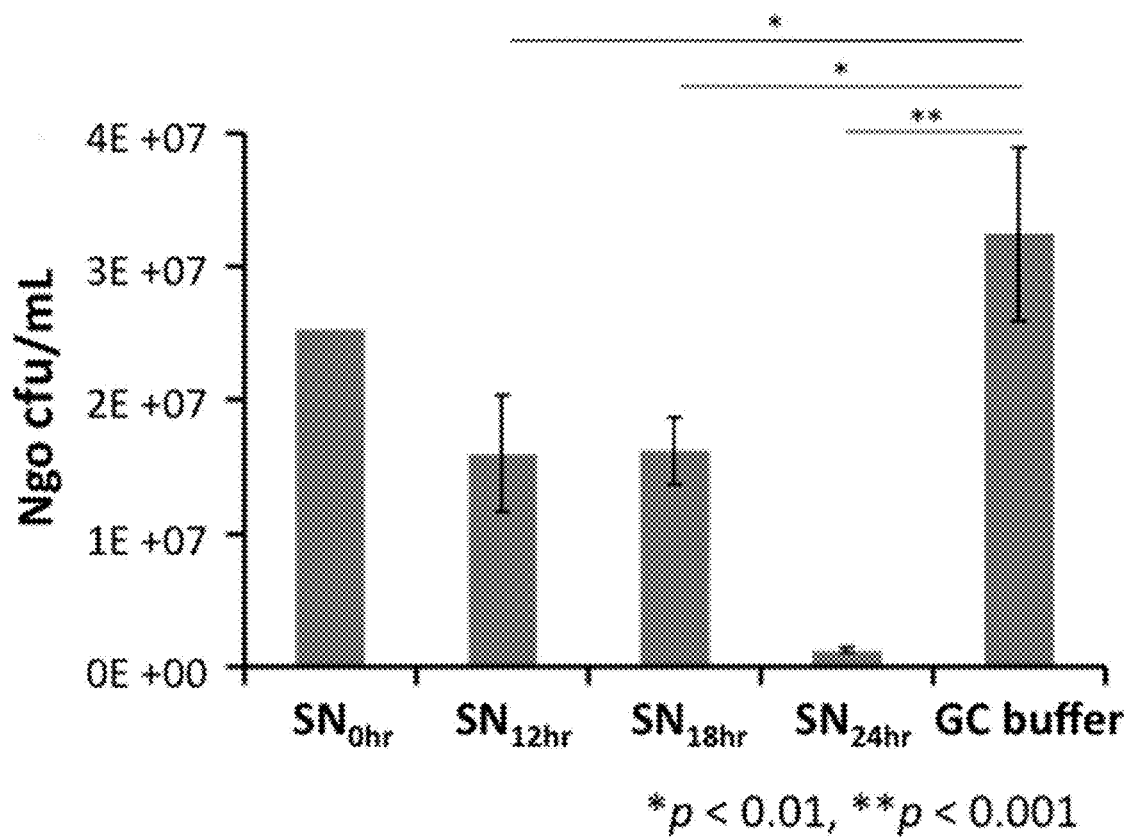
FIG. 2 shows Nel supernates reduce Ngo viability. Values, Standard Deviation and P values were calculated from three independent experiments. SN: supernate. GC buffer: media used to grow Nel. cfu/mL: colony forming units per ml of mixture. *$p<0.01$, **$p<0.001$, Student's t-test.
Figure 3:
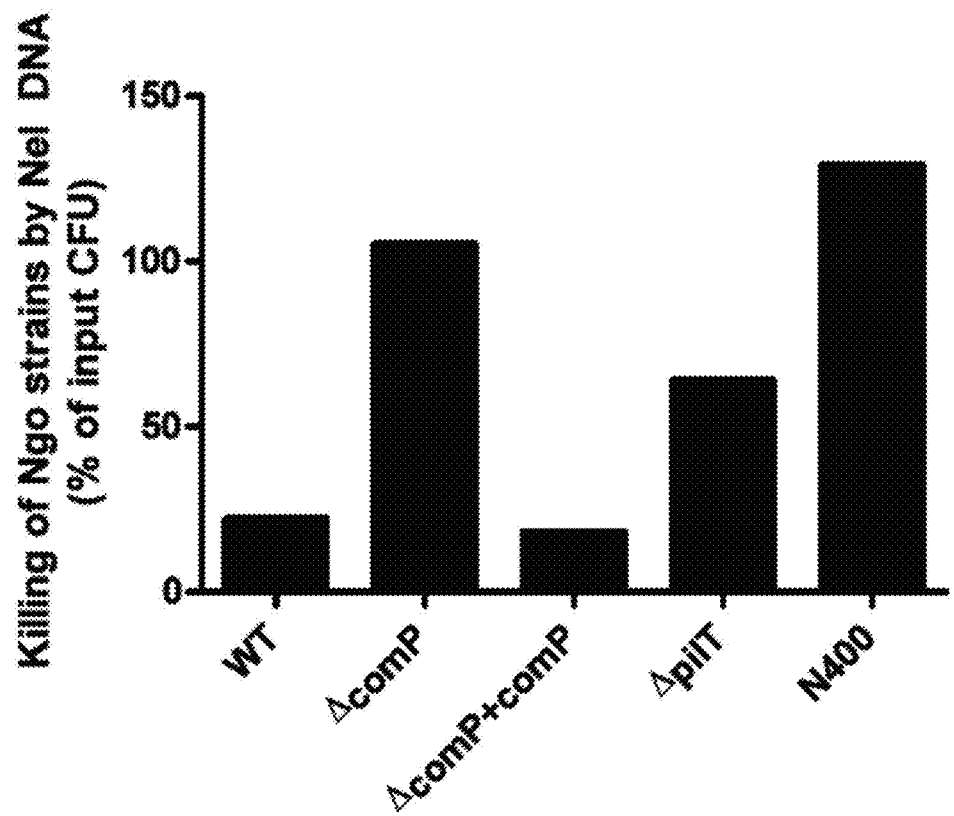
FIG. 3: Killing of Ngo strains by Nel DNA. WT and mutant Ngo were incubated with 20 ug/mL of purified Nel DNA for 4 hours, and the number of surviving Colony Forming Units (CFU) were expressed as a percent of input CFUs. WT: wild type Ngo. ΔcomP: Ngo mutant deleted of the comP gene and unable to take up neisserial DNA. ΔcomP+comP: the ΔcomP mutant complemented with a WT copy of comP. ΔpilT: Ngo mutant deleted of the pilT gene that encodes the Tfp retraction motor and cannot take up *neisseria* DNA. N400: Ngo mutant that cannot recombine the DNA taken up into the cell. These results indicate that WT Ngo is readily killed by Nel DNA, but Ngo mutants which cannot take up neisserial DNA are resistant to killing by Nel DNA.

Specifically, results from such experiments demonstrate that Ngo is killed when cultured in the presence of Nel (FIG. 1). Furthermore, Ngo is killed by the spent medium in which Nel was grown (FIG. 1), and by Nel DNA purified away from protein and RNA (FIG. 3). Such experiments also demonstrate that Ngo mutants ΔcomP, ΔpilT or ΔpilE, which cannot take up neisserial DNA, and Ngo mutant recA, which cannot recombine incoming neisserial DNA into the genome, are resistant to killing by Nel DNA (FIG. 2). Studies have shown that comP encodes the Tfp-associated protein that binds the DUS in neisserial DNA, pilT encodes the PilT motor complex that allows Ngo to take up the bound DNA into the bacterial cell, pilE encodes pilin, the structural subunit of the Tfp fiber.

Figure 4:
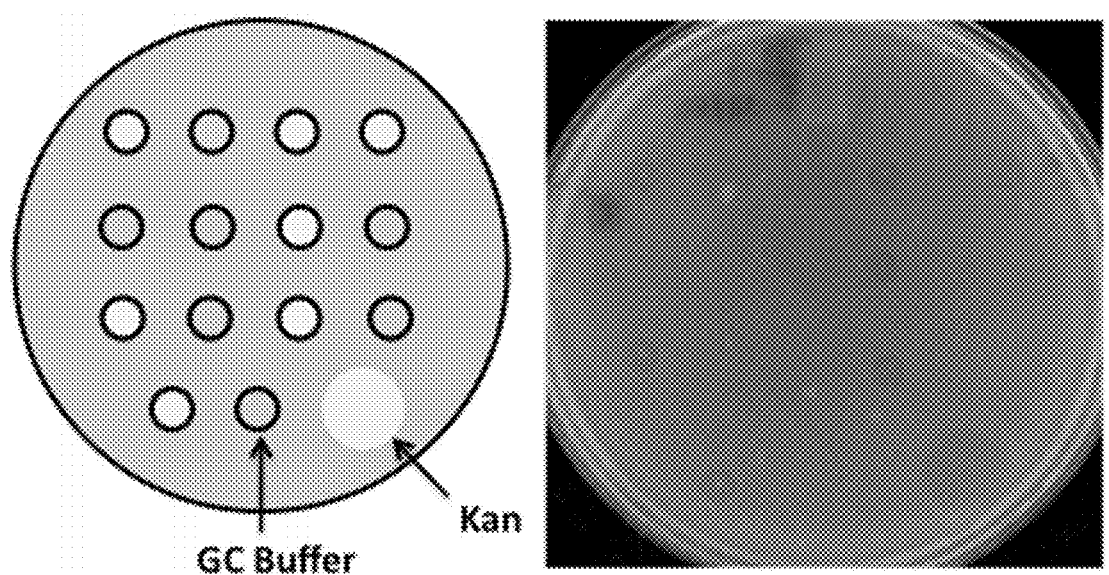
FIG. 4: Agar plate assay developed for detecting killing of Ngo by Nel supernate. Left: Diagram of an agar plate on which extracts from Nel were spotted on a lawn of Ngo cells. Circles indicate the location of the spotted extracts. Lighter circles indicate extracts that killed Ngo cells. Darker circles indicate extracts that failed to kill Ngo cells. GC buffer: media for growing *Neisseria* spotted on the lawn as a negative control (no killing of Ngo). Kan: Kanamycin spotted on the lawn as a positive control (Ngo killed).
Figure 8:
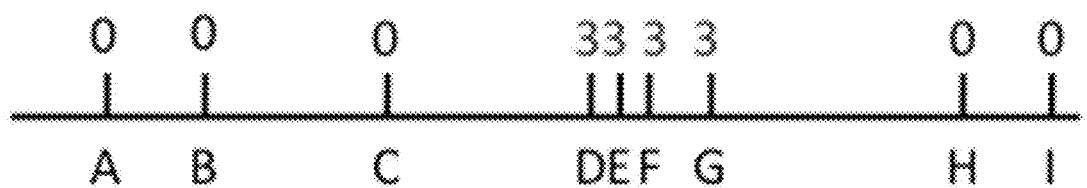
FIG. 8: Diagram of a hypothetical region of Nel DNA (solid line). Shown below are cut sites for hypothetical restriction enzymes A-I. Shown above are scores for restriction enzymes A-I based on their ability to abolish the killing activity of Nel DNA against Ngo; a score of 3 indicates maximal killing activity and a score of 0 indicates no killing activity.

Results from these in vitro experiments are recapitulated in animals. Ngo is cleared from mice more quickly when inoculated with Nel into the animals, compared to Ngo inoculated alone (FIG. 4). Importantly, one key Ngo mutant, Ngo ΔcomP, which cannot take up neisserial DNA, is cleared at the same rate whether Nel is present or not (FIG. 8). These results indicate that clearance of Ngo from the mouse is due to its killing by Nel, and requires its ability to take up Nel DNA.

Further experiments demonstrated that commensal species of *Neisseria* kill *N. gonorrhoeae* based on genetic competence and DNA methylation state. Killing occurs when the genetically competent pathogen takes up commensal DNA with a methylation pattern it does not recognize. Indeed, any DNA kills *N. gonorrhoeae* provided it is able to enter the cell and its methylation pattern is not native to the pathogen. Consistent with these findings, commensal *Neisseria elongata* accelerates the clearance of *N. gonorrhoeae* from the mouse vagina in a mouse model of infection, and a DNA uptake mutant of *N. gonorrhoeae* resists this clearance.

*Neisseria gonorrhoeae* (Ngo) and *Neisseria meningitidis* (Nme) are closely related pathogens that cause disease exclusively in humans. Ngo infects the urinary tract and oropharynx. Nme colonizes the upper respiratory tract, entering the bloodstream to cause septicemia and crossing the blood-brain barrier to cause meningitis.

Ngo is transmitted primarily by sexual contact. This bacterium causes over 160 million new infections each year across the world. In the body, Ngo reactivates Human Immunodeficiency Virus (HIV) in immune cells. Ngo has quickly developed resistance to all antibiotics currently used for its treatment. No new antibiotics against Ngo are in the drug development pipeline, and there is no vaccine against this bacterial pathogen (Rice et al., Annu Rev Microbiol 71, 665-686, doi:10.1146/annurev-micro-090816-093530 (2017). For these reasons, the National Institutes of Health, the Centers for Disease Control, and the World Health Organization have placed Ngo in their list of "superbugs".

Vaccines against Nme have significantly reduced the incidence of meningococcal disease. However, they do not cover all serogroups of Nme and are unaffordable in poor countries (Borrow, R. et al. The Global Meningococcal Initiative: global epidemiology, the impact of vaccines on meningococcal disease and the importance of herd protection. Expert Rev Vaccines 16, 313-328, doi:10.1080/14760584.2017.1258308 (2017)). The incidence of infection by serogroups of Nme not covered by the vaccines appears to be on the rise. Nme continues to cause occasional epidemics in Africa and the Middle East.

Ngo and Nme colonize asymptomatically at high frequency. Approximately 60% of Ngo cervical infections result in asymptomatic carriage, and 10-20% of healthy adults carry Nme in the upper respiratory tract with no symptoms of disease (Janda, W., et al., Prevalence and Site-Pathogen Studies of *Neisseria meningitidis* and *N. gonorrhoeae* in Homosexual Men. JAMA 244, 2060-2064 (1980); Gerbase, A., et al., Global burden of sexually transmitted diseass (excluding HIV) in the year 2000. Sexually Transmitted Diseases 15-08-06 (2000); Caugant, D. A. & Maiden, M. C. Meningococcal carriage and disease-population biology and evolution. Vaccine 27 Suppl 2, B64-70, doi:S0264-410X(09)00615-X [pii] 10.1016/j.vaccine.2009.04.061 (2009)). Asymptomatic infection, or "carriage", is an important aspect of infection because it is key to person-to-person transmission.

Thus, in certain embodiments, the present invention provides compositions comprising an effective amount of a commensal species of *Neisseria* (e.g., an effective amount of an extract of a commensal species of *Neisseria*). In some embodiments, the extract of a commensal species of *Neisseria* is capable of inhibiting the growth of Ngo and/or is capable of killing Ngo. Examples of commensal species of *Neisseria* capable of killing Ngo and/or inhibiting the growth of Ngo include, but are not limited to Nel and *N. polysaccharea* (Npo).

Such compositions are not limited to a particular type of extract of the commensal species of *Neisseria* capable of inhibiting the growth of Ngo and/or is capable of killing Ngo. In some embodiments, the extract is one or more polypeptides (e.g., 1, 2, 3, 4, 5, 6, 7, 8, 10, 20, 200, 2000, 9999, etc.) of the respective commensal *Neisseria* species. In some embodiments, the extract is one or more gene products of the respective commensal *Neisseria* species. In some embodiments, the extract includes at least a portion of nucleic acid of the respective commensal *Neisseria* species. In some embodiments, the extract includes one or more specific DNA loci of the respective commensal *Neisseria* species. In some embodiments, the extract includes at least a portion of genomic DNA of the respective commensal *Neisseria* species. In some embodiments, the extract includes at least a portion of chromosomal DNA of the respective commensal *Neisseria* species. In some embodiments, the extract is the entire live organism (e.g., in the form of a probiotic).

The compositions of the present invention can be prepared from a *Neisseria* species by any method suitable for obtaining a composition capable of inhibiting the growth of Ngo and/or killing Ngo. For example, in some embodiments, a sample having a particular strain of *Neisseria* (Nel) (or portion thereof) is provided and one or more purification steps and/or isolation steps and/or concentration steps resulting in purification and/or isolation and/or concentration from the sample a composition having an extract of the commensal species of *Neisseria* capable of inhibiting the growth of Ngo and/or killing Ngo.

In some embodiments, the composition comprises an isolated or purified nucleic acid comprising one or more copies of a DNA uptake sequence (DUS) and a methylation pattern different from a target bacterium (e.g., wherein at least a portion of the nucleic acid is derived from a commensal species of *Neisseria*).

The present invention is not limited to a particular DUS (See e.g., Frye S. A., Nilsen, M., Tonjum, T., Ambu, O. H. Dialects of the DNA uptake sequence in Neisseria. PLoS Genet. April; 9(4):e1003458. doi: 10.1371/journal.pgen.1003458. Epub 2013 Apr. 18 (2013).; herein incorporated by reference in its entirety). In some embodiments, the DUS has the sequence $N_1N_2N_3N_4N_5N_6N_7CTGN_8A$ (SEQ ID NO:1), wherein $N_1$ is A or T, $N_2$ is T, G, or A, $N_3$ is G or C, $N_4$ is C or T, $N_5$ is C, T, or A, $N_6$ is G or A, $N_7$ is T or C, and $N_8$ is C or A. For example, in some embodiments, the DUS has the sequence A[T/G]GCCGTCTGAA (SEQ ID NO:2) or GCCGTCTGAA (SEQ ID NO:3).

In some embodiments, at least a portion (e.g., at least 8, 15, 20, 30, 50 or more nucleotides) of the nucleic acid sequence is specific to the target bacterium and absent in commensal species of *Neisseria* that are normal inhabitants of the body. For example, in some embodiments, the portion comprises at least a portion of a gene selected from, for example, tdfF, tdfH, or iga.

In some embodiments, the nucleic acid does not inhibit the growth of or kill a commensal strain of *Neisseria*. In some embodiments, the at least a portion comprises sequences that are cleavable by restriction enzymes from the target bacterium if they are not methylated by the cognate methylase.

In some embodiments, the nucleic acid is synthesized de novo (e.g., with 5' phosphate and 3' hydroxyl groups), a plasmid, a bacterial artificial chromosome, or genomic DNA. In some embodiments, the methylation is cytosine methylation in CpG or GpC dinucleotides and/or adenine methylation. In some embodiments, the nucleic acid is produced in a microorganism (e.g., *E. coli*) that possesses a cytosine or adenine methylation system that results in different methylation that the target microorganism. In some embodiments, the nucleic acid is 0.1-100 kb in length (e.g., 0.1, 5, 10, 50, 100, or other lengths).

In some embodiments, the product or composition further comprises an agent that enhances DNA recombination in said target bacterium.

In some embodiments, such nucleic acids are prepared in vivo by culturing in an organism that has a different methylation pattern that a target bacterium (e.g., by culturing in *E. coli*). In some embodiments, the nucleic acid is plasmid, a bacterial artificial chromosome, or genomic DNA. In some embodiments, the methylation is cytosine methylation in CpG dinucleotides and/or adenine methylation. While the present disclosure is not limited to a particular methylation pattern, experiments described herein demonstrated that nucleic acids with a different methylation pattern than the target organism resulted in killing of the target organism. Thus, in some embodiments, the methylation pattern is different for nucleic acids that target different bacterium (e.g., nucleic acids for killing Ngo have different methylation pattern than those for killing Nme). Without being limited to a particular mechanism, it is contemplated that killing results during recombination when endogenous restriction systems target host nucleic acids due to the restriction enzyme recognition sites generated by methylation patterns of the nucleic acids in compositions of the present disclosure.

In some embodiments, the product or composition further comprises an agent that enhances DNA recombination in said target bacterium.

Such compositions are not limited to particular uses. In some embodiments, the compositions are capable of a static action wherein Ngo growth is inhibited. In some embodiments, the compositions are capable of a cidal action wherein Ngo organisms are killed. In some embodiments, the compositions are capable of a lytic action wherein Ngo organisms are killed and lysed.

In some embodiments, such compositions are heat stable (e.g., retains desired activity at any temperature for any desired amount of time).

In some embodiments, the composition is an antiseptic. Antiseptics are antimicrobial substances that are applied to living tissue/skin to reduce the possibility of infection and/or sepsis, and/or putrefaction. Antiseptics are generally distinguished from antibiotics by their ability to be transported through the lymphatic system to destroy bacteria within the body, and from disinfectants, which destroy microorganisms found on non-living objects. In some embodiments, antiseptic compositions comprising an effective amount of a commensal species of *Neisseria* (e.g., an effective amount of an extract of a commensal species of *Neisseria*) (e.g., Nel, Npo) capable of inhibiting the growth of Ngo and/or is killing Ngo are provided. For example, in some embodiments, such an antiseptic composition can be applied to the tissue of a subject (e.g., a human subject) for purposes of preventing the growth or inducing the killing of Ngo.

In some embodiments, the composition is a disinfectant. In some embodiments, disinfectant compositions comprising an effective amount of a commensal species of *Neisseria* (e.g., an effective amount of an extract of a commensal species of *Neisseria*) (e.g., Nel, Npo) capable of inhibiting the growth or of inducing the killing of Ngo are provided. For example, in some embodiments, such a disinfectant composition can be used in the cleaning of hospitals such as in cleaning of an operating room and/or surgery equipment. Disinfectants should generally be distinguished from antibiotics that destroy microorganisms within the body, and from antiseptics, which destroy microorganisms on living tissue.

In some embodiments, the compositions are used for anti-fouling. Anti-fouling is the process of removing or inhibiting the accumulation of biofouling. Biofouling or biological fouling is the undesirable accumulation of microorganisms, plants, algae, and animals on surfaces.

In some embodiments, the present invention relates to a pharmaceutical composition comprising an effective amount of a commensal species of *Neisseria* (e.g., an effective amount of an extract of a commensal species of *Neisseria*) (e.g., Nel, Npo) capable of inhibiting the growth or inducing the killing of Ngo. In some embodiments, the pharmaceutical composition comprises the entire live organism (e.g., the entire commensal species of *Neisseria*) (e.g., in the form of a probiotic). In some embodiments, such pharmaceutical compositions can be used as a medicament (e.g., for purposes of treating a subject having gonorrhea and/or any condition involving the presence of Ngo). In some embodiments, the treatment can be ameliorating, curative or prophylactic treatment of gonorrhea and/or any condition involving the presence of Ngo.

In some embodiments, the composition is a gel (e.g., formulated for delivery to a mucosal surface). In some embodiments, the gel coats a product for use in treating or preventing infection by Ngo or Nme (e.g., a condom). In some embodiments, the composition stabilizes the nucleic acid from degradation by enzymes in the mucosa.

In some embodiments, the composition is formulated for delivery to the oropharynx (e.g., as a toothpaste or mouthwash or inhaler).

The individual treated can be a human being or an animal. The animal can be a dog, cat, horse, rabbit, hamster, mouse, rat, monkey, cow, pig, donkey, fish, bird, reptile or any other animal in need of treatment. In one embodiment the animal is a laboratory/test animal. In another embodiment the animal in need of treatment is a pet or livestock such as domesticated cows, pigs, sheep, poultry or farmed fish.

The human being can be a man, a woman, a post-menopausal woman, a pregnant woman, a lactating woman, an infant, a child, or an adult. The individual such as a human being can be of any age such as from newborn to 120 years old, for example from 0 to 6 months, such as from 6 to 12 months, for example from 1 to 5 years, such as from 5 to 10 years, for example from 10 to 15 years, such as from 15 to 20 years, for example from 20 to 25 years, such as from 25 to 30 years, for example from 30 to 35 years, such as from 35 to 40 years, for example from 40 to 45 years, such as from 45 to 50 years, for example from 50 to 60 years, such as from 60 to 70 years, for example from 70 to 80 years, such as from 80 to 90 years, for example from 90 to 100 years, such as from 100 to 110 years, for example from 110 to 120 years.

In certain embodiments, methods for treating human subjects having gonorrhea are provided. In such embodiments, pharmaceutical compositions comprising an effective amount of a commensal species of *Neisseria* (e.g., an effective amount of an extract of a commensal species of *Neisseria*) (e.g., Nel, Npo) capable of inhibiting the growth or inducing the killing of Ngo are administered to such a human subject resulting the inhibition of and/or killing of Ngo.

In certain embodiments, methods for preventing human subjects from developing gonorrhea are provided. In such embodiments, pharmaceutical compositions comprising an effective amount of a commensal species of *Neisseria* (e.g., an effective amount of an extract of a commensal species of *Neisseria*) (e.g., Nel, Npo) capable of inhibiting the growth or inducing the killing of Ngo are administered to such a human subject resulting the inhibition or killing of Ngo exposed to the subject.

Such compositions may be administered using one or more of the following routes of administration. Indeed, routes of administration can broadly be divided into: Topical: local effect, substance is applied directly where its action is desired; Enteral: desired effect is systemic (non-local), substance is given via the digestive tract; Parenteral: desired effect is systemic, substance is given by routes other than the digestive tract.

Topical administration includes Epicutaneous (application onto the skin), Inhalational, Enema, Eye drops (onto the conjunctiva), Ear drops, Intranasal route (into the nose), and Vaginal.

Enteral administration is any form of administration that involves any part of the gastrointestinal tract and includes by mouth (peroral), by gastric feeding tube, duodenal feeding tube, or gastrostomy, and/or rectally.

Parenteral by injection or infusion include Intravenous (into a vein), Intraarterial (into an artery), Intramuscular (into a muscle), Intracerebral (into the cerebrum) direct injection into the brain, Intracerebroventricular (into the cerebral ventricles) administration into the ventricular system of the brain, Intracardiac (into the heart), Subcutaneous (under the skin), Intraosseous infusion (into the bone marrow) is, in effect, an indirect intravenous access because the bone marrow drains directly into the venous system, Intradermal, (into the skin itself), Intrathecal (into the spinal canal), Intraperitoneal, (infusion or injection into the peritoneum), Intravesical infusion is into the urinary bladder, and Intracavernosal injection is into the base of the penis. Other parenteral administration modes include Transdermal (diffusion through the intact skin), Transmucosal (diffusion through a mucous membrane), e.g. insufflation, sublingual, i.e. under the tongue, vaginal suppositories, Inhalational, Intracisternal: given between the first and second cervical vertebrae, Other epidural (synonym: peridural) (injection or infusion into the epidural space), and Intravitreal, through the eye.

Peroral intake may be in the form of Tablets, Capsules, Mixtures, Liquid, and Powder.

Injections may be either systemic or local injections.

Other administration modes of the present invention include Jet-infusion (micro-drops, micro-spheres, micro-beads) through skin, Drinking solution, suspension or gel, Inhalation, Nose-drops, Eye-drops, Ear-drops, Skin application as ointment, gel, lotion, cream or through a patch, Vaginal application as ointment (e.g., via condum, spermacide ointment, etc.), gel, crème or washing, Gastro-Intestinal flushing, and Rectal washings or by use of suppositories. In some embodiments, the composition is administered as a vaginal gel (e.g., hydroxyethycellulose). Administration can be performed as a single administration such as single intake, injection, application, washing; multiple administrations such as multiple intakes, injections, applications, washings; on a single day basis or over prolonged time as days, month, years.

A dose or dosage of the composition according to the present invention may be given as a single dose or in divided doses. A single dose occurs only once, with the drug administered either as a bolus or by continuous infusion. Alternatively, the dose may be divided into multiple doses and given recurrently, such as twice (two times), for example three times, such as four times, for example five times, such as six times, for example seven times, such as eight times, for example nine times, such as ten divided doses. Furthermore, the dose may be given repeatedly, i.e. more than once, such as twice (two times), for example three times, such as four times, for example five times, such as six times, for example seven times, such as eight times, for example nine times, such as ten times a day. Alternatively, the dose may be in sustained release form. A bolus is in theory regarded as given immediately, and should be administered in less than 5 minutes.

It follows that the composition according to the present invention may be given once or more daily, or alternatively may be given with intervals of 1 day, such as 2 days, for example 3 days, such as 4 days, such as 5 days, for example 6 days, such as 7 days (1 week), for example 8 days, such as 9 days, such as 10 days, for example 11 days, such as 12 days, for example 13 days, such as 14 days (2 weeks), such as 3 weeks, for example 4 weeks, such as 5 weeks, for example 6 weeks, such as 7 weeks, such as 8 weeks, for example 12 weeks.

The composition according to the present invention is given in an effective amount to an individual in need thereof. The amount of composition according to the present invention in one preferred embodiment is in the range of from about 0.01 milligram per kg body weight per dose to about 1000 milligram per kg body weight per dose. In some embodiments, the effective amount is the amount necessary for the composition to induce Ngo growth inhibition and/or killing of Ngo.

The composition according to the present invention can be co-administered to an individual in need thereof in combination with one or more drugs such as one or more drugs with antibacterial effect. The one or more antibiotics can be selected from the group consisting of Amikacin disulfate salt, Amikacin hydrate, Anisomycin from *Streptomyces griseolus*, Apramycin sulfate salt, Azithromycin, Blasticidine S hydrochloride, Brefeldin A, Brefeldin A from *Penicillium brefeldianum*, Butirosin sulfate salt, Butirosin A from *Bacillus vitellinus*, Chloramphenicol, Chloramphenicol base, Chloramphenicol succinate sodium salt, Chlortetracycline hydrochloride, Chlortetracycline hydrochloride from *Streptomyces aureofaciens*, Clindamycin 2-phosphate, Clindamycin hydrochloride, Clotrimazole, Cycloheximide from microbial, Demeclocycline hydrochloride, Dibekacin sulfate salt, Dihydrostreptomycin sesquisulfate, Dihydrostreptomycin solution, Doxycycline hyclate, Duramycin from *Streptoverticillium cinnamoneus*, Emetine dihydrochloride hydrate), Erythromycin, Erythromycin USP, Erythromycin powder, Erythromycin, Temephos, Erythromycin estolate, Erythromycin ethyl succinate, Erythromycin standard solution, Erythromycin stearate, Fusidic acid sodium salt, G 418 disulfate salt, G 418 disulfate salt powder, G 418 disulfate salt solution liquid, Gentamicin solution liquid, Gentamicin solution, Gentamicin sulfate *Micromonospora purpurea*, Gentamicin sulfate salt, Gentamicin sulfate salt powder USP, Gentamicin-Glutamine solution liquid, Helvolic acid from *Cephalosporium caerulens*, Hygromycin B *Streptomyces hygroscopicus*, Hygromycin B *Streptomyces hygroscopicus* powder, Hygromycin B solution *Streptomyces hygroscopicus*, Josamycin, Josamycin solution, Kanamycin B sulfate salt, Kanamycin disulfate salt from *Streptomyces kanamyceticus*, Kanamycin monosulfate from *Streptomyces kanamyceticus*, Kanamycin monosulfate from *Streptomyces kanamyceticus* powder USP, Kanamycin solution from *Streptomyces kanamyceticus*, Kirromycin from *Streptomyces collinus*, Lincomycin hydrochloride, Lincomycin standard solution, Meclocycline sulfosalicylate salt, Mepartricin, Midecamycin from *Streptomyces mycarofaciens*, Minocycline hydrochloride crystalline, Neomycin solution, Neomycin trisulfate salt hydrate, Neomycin trisulfate salt hydrate powder, Neomycin trisulfate salt hydrate USP powder, Netilmicin sulfate salt, Nitrofurantoin crystalline, Nourseothricin sulfate, Oleandomycin phosphate salt, Oleandomycin triacetate, Oxytetracycline dihydrate, Oxytetracycline hemicalcium salt, Oxytetracycline hydrochloride, Paromomycin sulfate salt, Puromycin dihydrochloride from *Streptomyces alboniger*, Rapamycin from *Streptomyces hygroscopicus*, Ribostamycin sulfate salt, Rifampicin, Rifamycin SV sodium salt, Rosamicin *Micromonospora rosaria*, Sisomicin sulfate salt, Spectinomycin dihydrochloride hydrate, Spectinomycin dihydrochloride hydrate powder, Spectinomycin dihydrochloride pentahydrate, Spiramycin, Spiramycin from *Streptomyces* sp., Spiramycin solution, Streptomycin solution, Streptomycin sulfate salt, Streptomycin sulfate salt powder, Tetracycline, Tetracycline hydrochloride, Tetracycline hydrochloride USP, Tetracycline hydrochloride powder, Thiamphenicol, Thiostrepton from *Streptomyces azureus*, Tobramycin, Tobramycin sulfate salt, Tunicamycin $A_1$ homolog, Tunicamycin C2 homolog, Tunicamycin *Streptomyces* sp., Tylosin solution, Tylosin tartrate, Viomycin sulfate salt, Virginiamycin $M_1$, (S)-(+)-Camptothecin, 10-Deacetylbaccatin III from *Taxus baccata*, 5-Azacytidine, 7-Aminoactinomycin D, 8-Quinolinol crystalline, 8-Quinolinol hemisulfate salt crystalline, 9-Dihydro-13-acetylbaccatin III from *Taxus canadensis*, Aclarubicin, Aclarubicin hydrochloride, Actinomycin D from *Streptomyces* sp., Actinomycin I from *Streptomyces antibioticus*, Actinomycin V from *Streptomyces antibioticus*, Aphidicolin *Nigrospora sphaerica*, Bafilomycin A1 from *Streptomyces griseus*, Bleomycin sulfate from *Streptomyces verticillus*, Capreomycin sulfate from *Streptomyces capreolus*, Chromomycin A₃ *Streptomyces griseus*, Cinoxacin, Ciprofloxacin BioChemika, cis-Diammineplatinum(II) dichloride, Coumermycin A1, Cytochalasin B *Helminthosporium dematioideum*, Cytochalasin D *Zygosporium mansonii*, Dacarbazine, Daunorubicin hydrochloride, Daunorubicin hydrochloride USP, Distamycin A hydrochloride from *Streptomyces distallicus*, Doxorubicin hydrochloride, Echinomycin, Echinomycin BioChemika, Enrofloxacin BioChemika, Etoposide, Etoposide solid, Flumequine, Formycin, Fumagillin from *Aspergillus fumigatus*, Ganciclovir, Gliotoxin from *Gliocladium fimbriatum*, Lomefloxacin hydrochloride, Metronidazole purum, Mithramycin A from *Streptomyces plicatus*, Mitomycin C *Streptomyces caespitosus*, Nalidixic acid, Nalidixic acid sodium salt, Nalidixic acid sodium salt powder, Netropsin dihydrochloride hydrate, Nitrofurantoin, Nogalamycin from *Streptomyces nogalater*, Nonactin from *Streptomyces tsusimaensis*, Novobiocin sodium salt, Ofloxacin, Oxolinic acid, Paclitaxel from *Taxus yannanensis*, Paclitaxel from *Taxus brevifolia*, Phenazine methosulfate, Phleomycin *Streptomyces verticillus*, Pipemidic acid, Rebeccamycin from *Saccharothrix aerocolonigenes*, Sinefungin, Streptonigrin from *Streptomyces flocculus*, Streptozocin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Trimethoprim, Trimethoprim lactate salt, Tubercidin from *Streptomyces tubercidicus*, 5-Azacytidine, Cordycepin, Formycin A, (+)-6-Aminopenicillanic acid, 7-Aminodesacetoxycephalosporanic acid, Amoxicillin, Ampicillin, Ampicillin sodium salt, Ampicillin trihydrate, Ampicillin trihydrate USP, Azlocillin sodium salt, Bacitracin *Bacillus licheniformis*, Bacitracin zinc salt *Bacillus licheniformis*, Carbenicillin disodium salt, Cefaclor, Cefamandole lithium salt, Cefamandole nafate, Cefamandole sodium salt, Cefazolin sodium salt, Cefinetazole sodium salt, Cefoperazone sodium salt, Cefotaxime sodium salt, Cefsulodin sodium salt, Cefsulodin sodium salt hydrate, Ceftriaxone sodium salt, Cephalexin hydrate, Cephalosporin C zinc salt, Cephalothin sodium salt, Cephapirin sodium salt, Cephradine, Cloxacillin sodium salt, Cloxacillin sodium salt monohydrate, D-{tilde over ( )}( )-Penicillamine hydrochloride, D-Cycloserine microbial, D-Cycloserine powder, Dicloxacillin sodium salt monohydrate, D-Penicillamine, Econazole nitrate salt, Ethambutol dihydrochloride, Lysostaphin from *Staphylococcus staphylolyticus*, Moxalactam sodium salt, Nafcillin sodium salt monohydrate, Nikkomycin, Nikkomycin Z *Streptomyces tendae*, Nitrofurantoin crystalline, Oxacillin sodium salt, Penicillic acid powder, Penicillin G potassium salt, Penicillin G potassium salt powder, Penicillin G potassium salt, Penicillin G sodium salt hydrate powder, Penicillin G sodium salt powder, Penicillin G sodium salt, Phenethicillin potassium salt, Phenoxymethylpenicillinic acid potassium salt, Phosphomycin disodium salt, Pipemidic acid, Piperacillin sodium salt, Ristomycin monosulfate, Vancomycin hydrochloride from *Streptomyces orientalis*, 2-Mercaptopyridine N-oxide sodium salt, 4-Bromocalcimycin A23187 BioChemika, Alamethicin *Trichoderma viride*, Amphotericin B *Streptomyces* sp., Amphotericin B preparation, Calcimycin A23187, Calcimycin A23187 hemi(calcium-magnesium) salt, Calcimycin A23187 hemicalcium salt, Calcimycin A23187 hemimagnesium salt, Chlorhexidine diacetate salt monohydrate, Chlorhexidine diacetate salt hydrate, Chlorhexidine digluconate, Clotrimazole, Colistin sodium methanesulfonate, Colistin sodium methanesulfonate from *Bacillus* colistinus, Colistin sulfate salt, Econazole nitrate salt, Hydrocortisone 21-acetate, Filipin complex *Streptomyces filipinensis*, Gliotoxin from *Gliocladium fimbriatum*, Gramicidin A from *Bacillus brevis*, Gramicidin C from *Bacillus brevis*, Gramicidin from *Bacillus aneurinolyticus* (*Bacillus brevis*), lonomycin calcium salt *Streptomyces conglobatus*, Lasalocid A sodium salt, Lonomycin A sodium salt from *Streptomyces ribosidificus*, Monensin sodium salt, N-(6-Aminohexyl)-5-chloro-1-naphthalenesulfonamide hydrochloride, Narasin from *Streptomyces auriofaciens*, Nigericin sodium salt from *Streptomyces hygroscopicus*, Nisin from *Streptococcus lactis*, Nonactin from *Streptomyces* sp., Nystatin, Nystatin powder, Phenazine methosulfate, Pimaricin, Pimaricin from *Streptomyces chattanoogensis*, Polymyxin B solution, Polymyxin B sulfate salt, DL-Penicillamine acetone adduct hydrochloride monohydrate, Polymyxin B sulfate salt powder USP, Praziquantel, Salinomycin from *Streptomyces albus*, Salinomycin from *Streptomyces albus*, Surfactin from *Bacillus subtilis*, Valinomycin, (+)-Usnic acid from *Usnea dasypoga*, (±)-Miconazole nitrate salt, (S)-(+)-Camptothecin, 1-Deoxymannojirimycin hydrochloride, 1-Deoxynojirimycin hydrochloride, 2-Heptyl-4-hydroxyquinoline N-oxide, Cordycepin, 1,10-Phenanthroline hydrochloride monohydrate puriss., 6-Diazo-5-oxo-L-norleucine, 8-Quinolinol crystalline, 8-Quinolinol hemisulfate salt, Antimycin A from *Streptomyces* sp., Antimycin A₁, Antimycin Az, Antimycin A3, Antipain, Ascomycin, Azaserine, Bafilomycin A1 from *Streptomyces griseus*, Bafilomycin B1 from *Streptomyces* species, Cerulenin BioChemika, Chloroquine diphosphate salt, Cinoxacin, Ciprofloxacin, Mevastatin BioChemika, Concanamycin A, Concanamycin A *Streptomyces* sp, Concanamycin C from *Streptomyces* species, Coumermycin A1, Cyclosporin A from *Tolypocladium inflatum*, Cyclosporin A, Econazole nitrate salt, Enrofloxacin, Etoposide, Flumequine, Formycin A, Furazolidone, Fusaric acid from *Gibberella fujikuroi*, Geldanamycin from *Streptomyces hygroscopicus*, Gliotoxin from *Gliocladium fimbriatum*, Gramicidin A from *Bacillus brevis*, Gramicidin C from *Bacillus brevis*, Gramicidin from *Bacillus aneurinolyticus* (*Bacillus brevis*), Gramicidin from *Bacillus brevis*, Herbimycin A from *Streptomyces hygroscopicus*, Indomethacin, Irgasan, Lomefloxacin hydrochloride, Mycophenolic acid powder, Myxothiazol BioChemika, N-(6-Aminohexyl)-5-chloro-1-naphthalenesulfonamide hydrochloride, Nalidixic acid, Netropsin dihydrochloride hydrate, Niclosamide, Nikkomycin BioChemika, Nikkomycin Z *Streptomyces tendae*, N-Methyl-l-deoxynojirimycin, Nogalamycin from *Streptomyces nogalater*, Nonactin □80% from *Streptomyces tsusimaensis*, Nonactin from *Streptomyces* sp., Novobiocin sodium salt, Ofloxacin, Oleandomycin triacetate, Oligomycin *Streptomyces diastatochromogenes*, Oligomycin A, Oligomycin B, Oligomycin C, Oligomycin *Streptomyces diastatochromogenes*, Oxolinic acid, Piericidin A from *Streptomyces mobaraensis*, Pipemidic acid, Radicicol from *Diheterospora chlamydosporia* solid, Rapamycin from *Streptomyces hygroscopicus*, Rebeccamycin from *Saccharothrix aerocolonigenes*, Sinefungin, Staurosporine *Streptomyces* sp., Stigmatellin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Triacsin C from *Streptomyces* sp., Trimethoprim, Trimethoprim lactate salt, Vineomycin A$_1$ from *Streptomyces albogriseolus* subsp., Tectorigenin, and Paracelsin *Trichoderma reesei*.

In a further embodiment the present invention relates to a kit of parts comprising the composition according to the present invention. The kit of parts comprises at least one additional component, such as instructions for use, and/or one or more drugs for co-administration.

EXPERIMENTAL

Materials and Methods
Reagents

Restriction enzymes and methyltransferases were purchased from New England Biolabs (NEB) (Ipswich, Mass., USA). Tissue culture plates were purchased from Corning (Corning, N.Y., USA). DNAse I and the T4 ligase were purchased from Promega (Madison, Wis., USA). Proteinase K was purchased from Thermo Fisher Scientific (Waltham, Mass., USA). Pure ethanol (molecular biology grade) was purchased from Sigma (St Louis, Mo., USA). Microplate dishes were purchased from Corning (Corning, N.Y., USA);
Bacterial Strains

*Neisseria gonorrhoeae*(Ngo) strain MS11 and *Neisseria elongata* (Nel) ATCC 29315 was used for all experiments (unless otherwise indicated) and was maintained on GCB agar plus Kellogg's supplements I and II at 37° C. and 5% $CO_2$. Clinical Ngo isolates D006 and D0020 were kindly provided by Dr. Joseph Duncan. Only piliated and Opa-non expressing bacteria, as monitored by colony morphology, were used, unless otherwise indicated. For genomic DNA extraction, 5-7 piliated commensal *Neisseria* and *Neisseria meningitidis* (strain MC58) colonies were lawned onto GCB agar (see Genomic DNA extraction). *E. coli* K12 was used for genomic extraction.

At the beginning of each experiment phenotypes were checked by monitoring colony morphology. In some experiments, MS11 ΔpilT (Dietrich et al., 2009) was used. For extraction of chromosomal DNA, the following strains were used: *E. coli* DH5a, *N. lactamica* ATCC 23970, *N. cinerea* ATCC 14685, *N. mucosa* ATCC 25996, *N. sicca* ATCC 29256, *N. polysaccharea* ATCC32768, and *Neisseria meningitidis* 8013. Ngo clinical isolates D006 and D0020 were isolated from the urethra of symptomatic male patients at Durham County STD clinic (Durham, N.C., USA). *E. coli* was grown on LB medium or agar. Bacterial density was calculated using the following formulas. Ngo MS11 and Nme 8013: $OD_{600}$ 1.4=1×10$^9$ CFUs; Nel 29315: $OD_{600}$ 1.0=1.2×10$^9$ CFUs. Table 11 shows exemplary bacterial strains.
DNA Spot Assay Ngo grown in GCB+VCN agar for 16 h was collected and suspended in liquid GCB at OD of 0.2. 100 uL of the resuspension was plated onto a new GCB+VCN agar. 5 uL of DNA (20 ng/uL) or Nel supernatant was added onto the plate and allowed to dry for 5-10 min. The plate was incubated at 37 C/5% $CO_2$ for 12-16 h, before the plate was read for clearance zones.
DNA Liquid Culture Killing Assay 5×10$^5$ CFU of Ngo was seeded onto 24 well dish (with 24 μM $FeNO_3$ for growth) in presence of different concentrations of purified Nel DNA. $MgSO_4$ (5 mM) was added to each well. The plate was incubated for 4 h at 37 C/5% $CO_2$ for 4 h. The serial dilutions of the harvested bacteria were plated onto GCB+VCN agar plates.
BAC cloning 180 ug of Nel genomic DNA was partially digested with 10 u of SphI for 15 minutes at 37 C. Digested DNA was run on a Clamped Homogenous Electric Fields (CHEF) gel. Gel regions containing 20-60 kb sized fragments were excised and DNA was eluted via electrophoresis. Eluted DNA was size selected for the second time via 0.6% agarose (50 V, 4 h), to remove DNA fragments smaller than 20 kb. 6 ng of pBeloBAC11 BAC vector digested with SphI was ligated with 65 ng of insert prepared above. The ligation mixture was electroporated into *E. coli* Turbo Electrocompetent 5alpha (NEB). Transformed bacteria were plated onto selected via blue/white colony selection.
Modification of pBlunt Vector pBlunt vector was purchased from Thermo Fisher Scientific. For addition of DUS, the complete sequence of pBlunt was amplified using a forward primer containing DUS. To clone a fragment of Ngo genome into pBlunt, the coding region of NgoIV restriction modification system was PCR amplified. The amplicon was then ligated to pBlunt vector per manufacturer's specification.
Genomic DNA Extraction Bacteria grown on agar plates were harvested and lysed using 0.05% SDS. Proteins from the lysed contents were removed via addition of Phenol. Residual proteins and phenol were subsequently removed via extraction using 25:24:1 Phenol-Chloroform-Isoamylalcohol mixture. Pure ethanol was used to precipitate the gDNA. The precipitated DNA was washed 3 times with 70% ethanol.
In Vitro DNA Methylation CpG and GpC methyltransferases (NEB) were incubated with DNA per manufacturer's specifications. Briefly, 100 ug of DNA was incubated with 20 uL of the methyltransferase in Nuclease free water in total volume of 500 uL in 1×NEB methyltransferase buffer. Final concentration of 640 uM S-adenosylmethionine (SAM) was added to supply the methyl groups.
Deletion of RM Systems NgoII restriction enzyme gene was replaced with a kanamycin cassette. For deletion of NgoIV and NgoV RM systems, the coding sequences were removed via 1 kb DNA fragment containing the sequences flanking NgoIV and NgoV. The deletion mutants were verified by sequencing as well as restriction digests of the gDNA by isoschizomers of deleted enzymes.
Statistics Statistical analysis was performed using standard student t-test analysis with GraphPad 5.0 (San Diego, Calif., USA).
Scanning Electron Microscopy Ngo and Nel (5×10$^7$ CFUs of each organism) were cultured alone or in a 1:1 ratio on glass coverslips in a 6-well microplate for 5 h. Bacteria were imaged by scanning electron microscopy as described (Higashi et al., 2011, infra).
Co-Culture Experiments Nel and Ngo cells harvested from 15 h agar plates (in log phase) were resuspended in GC broth with Kellogg's Supplements I and II (Kellogg et al., 1963). Cells were adjusted to approximately the same density and either grown separately (~5×10$^7$ CFUs) or together (~5×10$^7$ CFUs each strain) in 1 ml total volume in 6-well microplate dishes at 37° C., 5% $CO_2$. At the indicated times, the cultures were harvested and serial dilutions made with GC broth were plated on LB agar for Nel CFUs, and GCB agar containing vancomycin (3 mg/mL), colistin (7.5 mg/mL), and nystatin (12.5 mg/mL) (Jacobs and Kraus, 1975) for Ngo CFUs. Plates were incubated overnight and colony forming units were quantitated. Plates incubated for up to 48 h did not increase CFU counts. For co-culture experiments with Ngo clinical isolates D006 and D0020, 0.5 ml of fresh supplemented GC broth was added to each well every 24 hrs to replenish nutrients.

Construction of ΔcomP and Complemented ΔcomP

The comP open reading frame (ORF) was replaced with the kanamycin resistance gene (kan). Primers comP_MS11_F and comP_MS11_R (Table 14) containing Ngo comP flanking sequences were used to amplify kan from plasmid pNBNeiKan (Weyand et al., 2016). WT was transformed with the amplicon by spot transformation. Transformants were selected on GCB supplemented agar containing kanamycin (30 μg/ml). To construct the complemented comP strain, a copy of comP and its native promoter was inserted between the iga and trpB sites in WT Ngo MS11 and this region was cloned into the SacI and NdeI sites of pMR68 (Ramsey et al., 2012) to generate plasmid pcomPc. The plasmid was then introduced into Ngo by spot transformation. Transformants were selected on GCB supplemented agar containing erythromycin (10 μg/mL). The comP insertion was verified by PCR and sequencing using primers listed in Table 14. In a verified comP clone, the native comP was removed as described above. The resulting Ngo ΔcomP/comP strain was confirmed by PCR and sequencing.

Competitive Mouse Infection Experiments

A modification of the female mouse model of experimental Ngo genital tract infection (Jerse et al., 2011) was used to determine whether Nel inhibited Ngo in vivo. Female BALB/c mice (6 to 8 weeks old; National Cancer Institute or Charles River) in the anestrus or diestrus stage of the estrous cycle were identified by vaginal smear and treated with Premarin (Pfizer) on days −2, 0, and +2 and antibiotics to reduce the overgrowth of commensals that occurs under the influence of estrogen (streptomycin, 2.4 mg, BID; vancomycin, 0.4 mg, BID; and trimethoprim, 0.4 g/liter of drinking water) (Jerse et al., 2011). Mice were inoculated vaginally on day 0 with 20 μl of a phosphate-buffered saline (PBS) suspension containing similar numbers of Nel mixed with piliated Ngo, Ngo ΔcomP, or Ngo ΔcomP/comPwT (total CFU ~2×10$^6$ per 20 μl inoculum) (n=8-9 mice per group). Control groups received 10$^6$ CFU of Nel alone or each Ngo strain alone. Vaginal swabs were collected daily for 7 days post-inoculation and plated on GCB agar with VCNT supplement (Sigma) and 100 μg/ml streptomycin (Sm) for Ngo CFUs, and on LB agar with 100 μg/ml Sm for Nel CFUs. Differences in the percentage of mice colonized with each species over the 7-day period were analyzed by the Log Rank test. The number of Ngo and Nel CFUs recovered over time was analyzed by a repeated measures ANOVA.

Assaying Toxicity of Nel Supernatants for Ngo

Nel at a starting density of 2×10$^6$ CFUs/mL were grown in GC broth with Kellogg's supplements I and II for 0, 12, 18, and 24 h at 37° C., 5% $CO_2$. Cells were pelleted by centrifugation and the supernatants collected. Supernatants were filtered through a 0.22 μM PVDF filter unit (Millipore) pre-blocked with supplemented GC broth containing 50 mg/mL BSA, then being washed with supplemented GC broth. An equal volume of fresh supplemented GC broth was added to the filtered supernatant and used as the assay broth. Ngo was added to the assay broth at 2×10$^7$ CFUs/mL and 0.5 mL was added to each well of a 12 well culture plate (Falcon). As a negative control, a parallel set of cultures was initiated in which Ngo was incubated with filtered supplemented GC broth (Millipore) with an equal volume of fresh supplemented GC broth. Cultures were incubated for 5 h at 37° C., 5% $CO_2$. Ngo CFUs were quantitated by plating serial dilutions on GCB+VCN agar plates. Plates were incubated overnight and colony forming units were quantitated. Plates incubated for up to 48 h did not increase CFU counts.

Spot Assay

Ngo grown on GCB agar plates for 16 h was collected with a sterile Dacron swab and suspended in liquid GC broth to $OD_{600}$ of 0.2. 100 μL of the bacterial suspension was spread evenly on a GCB agar plate. 5 μL of DNA (20 ng/mL) or Nel supernatant was spotted onto defined sections of the plate, and the liquid was allowed to dry at 37° C. for 5-10 min. The plate was incubated at 37° C., 5% $CO_2$ for 12-16 h and the zones of clearance were recorded. 5 μl each of kanamycin (20 μg/ml) and GC broth were spotted on the agar to serve as positive and negative controls, respectively.

DNA Liquid Culture Killing Assay

Ngo, Nel and Nme (5×10$^5$ CFUs each) were suspended in GC broth containing Kellogg's Supplements I and II and $MgSO_4$ (5 mM), and seeded into 24-well microplates (Corning). DNA was added to the wells at the indicated concentrations, and the plates were incubated for 4 h at 37° C., 5% $CO_2$. The bacteria were harvested with a P1000 pipette, and serially diluted in liquid GC broth. The serial dilutions were plated onto GCB agar containing Kellogg's Supplements I and II and the plates incubated overnight before colony forming units were counted.

Extraction of Chromosomal DNA

*Neisseria* spp. were grown on GCB agar with Kellogg's supplements I and II, and *E. coli* on LB agar plates, for 16 to 18 h at 37° C., 5% $CO_2$. Cells from one plate were collected with a sterile Dacron swab (Fisher Scientific, Hampton, N.H., USA) into 500 μL of GC lysis buffer (0.5 M NaCl, 10 mM EDTA, 50 mM Tris, pH 8.0) with 1% SDS and 1 mg/μL RNAse A (Qiagen, Hilden, Germany). Cells were allowed to lyse at RT for 5 min. DNA from the lysates were extracted sequentially with an equal volume of phenol, phenol-chloroform-isoamyl alcohol (25:24:1), and chloroform. For each extraction step, lysate-organic solvent mixtures were vortexed (1 min) and transferred to phase lock gels (VWR, Radnor, Pa., USA). The mixtures were centrifuged at 16,000×g for 5 min and the aqueous (upper) phases were collected into 15 mL conical tubes. DNA was precipitated with 5 volumes of molecular biology grade 100% ethanol (Sigma-Aldrich, USA) and 2.5 M ammonium acetate at 4° C. for 30 min. Precipitated DNA was washed twice with 70% ethanol and dissolved in TE buffer (10 mM Tris, 0.1 mM EDTA, pH 8.0). To assess DNA purity, the NanoDrop spectrophotometer (Thermofisher) was used to determine the ratio of absorbance at 260 nm to 280 nm. The OD260/OD280 ratio of DNA preparations were 1.8-2.0.

Construction of Bacterial Artificial Chromosomes (BAC)

For preparation of inserts, 15 μg of Nel chromosomal DNA was partially digested with 10 units of SphI restriction enzyme (NEB) for 15 min at 37° C. Digested DNA was separated in a 1% agarose gel, in 0.5×TBE buffer, using clamped homogenous electric fields (CHEF) (Bio-Rad Laboratories, Hercules, Calif., USA) at 1-50 sec linear ramp, 6 V/cm for 14 h. Regions of the gel containing 20-60 kb fragments were excised and the DNA was eluted using Model 422 Electro-Eluter (Bio-Rad Laboratories) per vendor specifications. Eluted DNA was further size selected using 0.6% megabase agarose (Bio-Rad Laboratories, USA) at 50V for 4 h (1×TAE buffer), to exclude fragments smaller than 20 kb. For preparation of vector DNA, 8 ng of pBeloBAC11 (NEB) was digested with 10 units of SphI at 37° C. for 1 h. Digested pBeloBAC11 was incubated with 180 ng of inserts, prepared above, in the presence of 5 μL of T4 ligase (Promega), per vendor instruction, at 16° C. overnight. The ligation mixtures were desalted on 0.1 M glucose/1% agarose cones for 90 min on ice (Atrazhev and Elliott, 1996). Desalted DNA was electroporated (325 DC V, 4 kΩ, 330 μF) into E. coli Turbo Electrocompetent 5alpha (NEB #2984H). After recovery in SOC medium at 37° C. for 1 h with continuous shaking, electroporated E. coli cells were plated on LB agar containing chloramphenicol (12.5 μg/mL), X-gal (80 mg/mL) and IPTG (100 μg/mL). White colonies were picked and grown in liquid LB containing 12.5 μg/mL chloramphenicol at 37° C. for 16 h with continuous shaking. BACs were extracted using NucleoBond Midi columns (Macherey-Nagel, Düren, Germany).

Restriction Enzyme Analysis of pBeloBAC11 Inserts

5 μg of purified BACs were digested with 20 units of NotI or SphI restriction enzymes (NEB, USA). Digested DNA was separated by 0.6% megabase agarose (Bio-Rad Laboratories, USA) at 50V for 4 h. To determine the expected fragment sizes, BAC inserts were sequenced with M13 primers and the sequences matched to the Nel reference genome (Accession # NZ_CP007726.1).

Subcloning of pBeloBAC11(6.1)

5 μg of purified BAC6.1 DNA was partially digested with 2 units of PstI restriction enzyme (NEB) at 37° C. for 15 min. Digested DNA was separated in a 0.7% agarose gel (1×TAE buffer) at 90V for 1 h. The region of the gel containing 5-10 kb fragments was excised and the DNA was extracted using gel extraction kit (Qiagen). To prepare vector DNA, 10 ng of pUC19 was digested with 10 units of PstI at 37° C. for 1 h. Digested pUC19 was incubated with 30 ng of inserts prepared above, in the presence of 2 μL of T4 ligase (Promega), per vendor specifications. Competent E. coli DH5a was transformed with 4 μL of ligation mixture. Transformants, after recovery in SOC medium at 37° C. for 1 h with continuous shaking, were selected on LB agar containing ampicillin (100 μg/mL). Plasmids were extracted from selected colonies and sequenced using M13 primers listed in Table 14.

Construction of Ngo TD3 (Deletion of the ngoII, ngoIV, and ngoV Restriction/Modification (RM) Loci)

For each RM locus, a plasmid containing sequences immediately flanking the ORFs was constructed as follows. ORFs and flanking sequences were PCR amplified with primers listed in Table 14, and the amplicons were digested with following restriction enzymes (NEB): ClaI and NaeI (ngoII), PmeI (ngoIV), and AseI (ngoV). Digested products were blunted with 1 unit of DNA polymerase fragment Klenow (Promega) at RT for 15 min, per vendor specifications. Pieces of DNA containing the flanking regions of each ORF (identified on a 0.7% agarose gel based on fragment sizes) were extracted and ligated with T4 ligase (Promega) per vendor specifications. Ligation products were cloned into pCR-Blunt (Fisher Scientific) with T4 ligase (Promega), generating plasmids pCR-Blunt (ngoII-fs), pCR-Blunt (ngoIV-fs), and pCR-Blunt (ngoV-fs). To generate single RM mutants, WT MS11 was spot transformed with 500 ng of each plasmid. Deletion of each RM system was verified by PCR and sequencing using primers listed in Table 14. To generate the triple RM mutant, TD3, MS11 ΔngoIV was sequentially spot transformed with 500 ng of pCR-Blunt (ngoV-fs) and pCR-Blunt (ngoII-fs). At each step, deletion of RM systems was verified by PCR and sequencing using primers listed in Table 14. Loss of methyltransferase activities in TD3 was verified by confirming the susceptibility of TD3 DNA to digestion with cognate restriction enzymes HaeIII, NgoIV, and BamHI (NEB).

Analysis of Ngo and Nel Chromosomes for Short Sequence Homology to pCR-Blunt

NCBI Nucleotide Blast program with blastn algorithm (blast.ncbi.nlm.nih.gov/Blast.cgi) was used to align pCR-Blunt to Ngo MS11 (taxid: 528354) and Nel ATCC 29315 (taxid:546263) chromosomes. The following algorithm parameters were used to align short <20 bp sequences: max target sequence of 20000 adjusted for short input sequences with expected threshold of 1000 and word size of 7. Match and mismatch scores were set to 1 and −4, respectively. Scoring costs for existence and extension of gap were set to 5 and 2, respectively. These parameters were selected to minimize the number of alignments containing mismatches or gaps. Of >14000 matches, one alignment contained a single mismatch and was removed from further analysis. Sequence alignments between pCR-Blunt and MS11 chromosome were imported into Unix program Vim and the number of recognition sequences from MS11 restriction modification systems were counted via regular expression searches.

Testing a DNA Fragment with an E. coli or Ngo Methylation Signature for its Ability to Kill Ngo For this experiment, the iga gene in Ngo was modified as follows. A DNA fragment containing a site for the AsiSI restriction enzyme, a DUS and the first 980 bp of the 5' coding sequence of iga was synthesized (Integrated DNA Technologies, San Jose, Calif., USA) (Table 15). A second fragment containing the terminal 687 bp of the iga coding sequence, 293 bp of the iga downstream flanking sequence, a DUS and an AsiSI site was also synthesized. The sequence order of the two fragments is AsiSI-DUS-5'iga and 3'iga-DUS-AsiSI. Each fragment was cloned into pCR-Blunt, generating pCR-Blunt (iga5) and pCR-Blunt (iga3), respectively. The iga locus in Ngo was converted to AsiSI-DUS-iga-DUS-AsiSI (ADIDA) by sequential transformation of WT bacteria with pCR-Blunt (iga5) and pCR-Blunt (iga3) DNA (500 ng each), generating mutant Ngo i35A. All construction steps were verified by sequencing (Table S8) and confirmed by restriction digestion. The WT Ngo genome contains 9 AsiSI sites; the shortest AsiSI fragment is >15 kb. i35A contains two new AsiSI sites, flanking iga, and AsiSI digestion releases the 4 kb ADIDA fragment (Fig S5).

The ADIDA fragment was isolated from Ngo i35A for killing assays. Chromosomal DNA from i35A (1 mg) was digested with AsiSI (500 units, 37° C. for 4 h), and the fragments were separated in a preparatory 0.7% agarose gel. The gel region containing 4 kb DNA was excised and the DNA purified using a gel-extraction kit (Thermo-Fisher, K0691).

The ADIDA locus in Ngo i35A was cloned into plasmid pCR-Blunt by PCR amplification using primers listed in Table 14 and the amplified DNA was transformed into E. coli DH5α, generating recombinant pCR-Blunt (ADIDA). The insert from pCR-Blunt (ADIDA) was purified from the vector by AsiSI digestion, agarose gel separation and extraction as described above.

ADIDA fragments derived from E. coli and i35A (1 μg/mL each) were compared for their ability to kill Ngo using the liquid killing assay described above. Nel DNA (20 μg/ml) served as the positive control.

Construction of pCR-Blunt(DUS)

The entirety of pCR-Blunt (Fisher Scientific) was PCR amplified with primers DUS-pCR-Blunt_F and pCR-Blunt_R (Table 14). DUS was added via DUS-pCR_Blunt_F, which contains a DUS (GCCGTCTGAA (SEQ ID NO:3)). PCR amplicons were circularized with T4 ligase (Promega), per vendor specifications, and transformed into chemically competent *E. coli* DH5α. Transformants were allowed to recover in SOC medium at 37° C. for 1 h, and selected on LB agar containing 50 µg/mL of kanamycin. DUS in the resulting plasmid pCR-Blunt(DUS) was confirmed by sequencing using M13 primers listed in Table 14.

In Vitro Methylation of DNA

DNA was incubated with CpG and GpC methyltransferases (M.CviPI and M.SssI, respectively) (NEB) per vendor specifications. Briefly, 100 µg of DNA was incubated with 20 µL of methyltransferase in nuclease-free water in a total volume of 500 µL (1×NEB methyltransferase buffer). S-adenosylmethionine (SAM) (NEB) was added to a final concentration of 640 uM. Methylation was verified by digesting 1 µg DNA with 20 units of HaeIII or BstUI at 37° C. for 1 h.

Determination of Modifications in *Neisseria* and *E. coli* DNA

Total DNA was extracted from Nel using a Wizard Genomic DNA Purification Kit (Promega, USA). Whole-genome sequencing was conducted using the PacBio RSII platform (Pacific Biosciences, Menlo Park, Calif.) with P6-C4 chemistry. Each isolate was sequenced using one SMRT cell. Sequencing reads were then assembled using the hierarchical genome assembly process (HGAP3, SMR-TAnalysis 2.3.0) workflow, which included consensus polishing using Quiver (Chin et al., 2013). The resulting assembled genomes contained 1-7 contigs each. Methylation analyses were performed using the Modification and Motif Analysis pipeline in SMRT Portal, and motifs and associated modified bases were identified and characterized.

Example I

This example demonstrates that Nel dramatically reduces Ngo viability when the two species were cultured together in vitro (FIG. 1). Whether Nel inhibits Ngo growth in vitro was determined (FIG. 1).

Method: Nel 29315 SmR and Ngo MS11 SmR were suspended in liquid GCB+Supplements I/II, and inoculated together or alone into wells of tissue culture plates ($1 \times 10^7$ each species). The cultures were incubated at 37° C., 5% $CO_2$, and at various times triplicate wells were plated on GCB agar+Sm for Nel cfus, and GCB agar+VCN for Ngo cfus.

Result: Nel and Ngo grew normally when grown alone, but Ngo viability was reduced ~3 logs when Nel was present (5-hr vs 24-hr time point). Nel similarly reduced the viability of three fresh Ngo clinical isolates. Thus, Nel kills Ngo in liquid culture, and killing is not strain-specific.

Example II

This example demonstrates that Nel supernate reduces Ngo viability. It was determined whether the Nel compound that reduces Ngo viability is in the medium (FIG. 2).

Method: Nel was grown alone for 24 hrs in liquid GCB+Supplements I/II, at 37 C, 5% $CO_2$. Supernates were harvested at various times, filter sterilized, and incubated with Ngo MS11 for 5 hrs, in triplicate, and Ngo cfus were plated on GCB agar+VCN.

Result: Cell free supernates from the 12-hr and 18-hr time points reduced Ngo viability ~10-fold, while those from the 24-hr time point reduced viability >2.5 logs, compared to the 0-hr supernate (from Nel that had been freshly suspended in media). Three independent experiments yielded similar results. This suggests that Nel, in the absence of Ngo, releases/secretes a compound(s) into the medium that reduces Ngo viability.

Example III

This example shows that Nel DNA kills WT Ngo but not Ngo mutants that cannot take up or be transformed by neisserial DNA. In these experiments, $5 \times 10^5$ WT or mutant Ngo cells were incubated for 4 hours in presence or absence of Nel DNA (20 ug/mL). Ngo Only 22% of WT Ngo survived when cultured in the presence of Nel DNA (FIG. 3, first column). The Ngo ΔcomP mutant, which cannot bind to the neisserial DUS and therefore cannot take up neisserial DNA, is resistant to killing by Nel DNA (FIG. 3, second column). The complemented ΔcomP mutant, which expresses a WT copy of the comP gene, is now as sensitive to killing by Nel DNA as the WT Ngo strain (FIG. 3, third column). The Ngo ΔpilT mutant, which cannot take up the neisserial DNA that is bound to the ComP protein, is significantly more resistant to killing by Nel DNA, compared to WT Ngo (FIG. 3, fourth column). The Ngo N400 mutant, which cannot be transformed by DNA because it cannot recombine the entering DNA into its genome, is as resistant to killing by Nel DNA as the ΔcomP mutant (FIG. 3, fifth column). Taken together, these results indicate that the sensitivity of Ngo to killing by Nel requires its ability to take up neisserial DNA, and that the killing activity of Nel consists at least in part to its DNA.

Example IV

This example demonstrates Nel killing of Ngo is replicated by an agar plate assay. An agar plate assay was developed to study Ngo killing by Nel supernate (FIG. 4).

Method: An agar plate assay was developed to detect killing of Ngo by Nel supernate Ngo (see, FIG. 4). Ngo MS11 cells are spread evenly (uniformly distributed) over an agar plate. Different concentrations (same volume) of highly purified (protein and RNA free) Npo DNA are spotted onto the lawn of Ngo cells, and the plate is incubated overnight at 37° C. After overnight incubation, Ngo cells will grow into a dense and opaque lawn that is visible by eye. A clear zone in the lawn where a DNA solution was applied indicates that that DNA has killed Ngo cells. The negative control for this assay is GC buffer. The positive control for this assay is Kanamycin (Kan) (50 mg/uL).

Result: The 24-hr cell free Nel supernate and Kanamycin (50 ug/ml) produced clear zones on the lawn, indicating they inhibited Ngo growth, while GC buffer did not affect Ngo growth.

Example V

This example demonstrates that Ngo susceptibility to killing involves its uptake of Nel DNA. The nature of the lethal compound in the Nel supernate was determined using the agar plate assay.

Experimental protocol: Nel cells were grown in liquid for 24 hours, and the cells were pelleted by centrifugation. The supernate was passed through a membrane with small pores to remove any remaining bacteria. A portion of the filtured supernate was plated on agar to corroborate its sterility. The sterile 24-hr Nel supernate was subjected to various treatments and these samples were assessed for their ability to kill Ngo using the agar plate assay.

Result: Boiling, digestion with RNAse-free DNAse I, and UV cross-linking abolished the ability of the Nel supernate to kill Ngo. Proteinase K digestion and RNAse A digestion did not affect its killing activity. This suggests that Nel supernate killing of Ngo involves a DNA component (Table 1).

TABLE 1

Anti-Ngo activity of Nel supernates and DNAs; and susceptibility of Ngo mutants to killing by 24-hr Nel supernate.

|  | Exp1 | Exp2 | Exp3 |
|---|---|---|---|
| Treatment of supernate | | | |
| 37 C., 3 hr | + | + | + |
| 100 C., 3 hr | − | − | − |
| DNAse I | − | − | − |
| Boiled DNAse I (100 C., 3 hr) | + | + | + |
| UV, 30 min | − | − | − |
| Mock UV, 30 min | + | + | + |
| Proteinase K | + | + | + |
| Proteinas K (boiled 1 hr) | + | + | + |
| DNA | | | |
| Nel DNA | + | + | + |
| Ngo DNA | − | − | − |
| Nme DNA | − | − | − |
| E. coli DNA | − | − | − |
| Nel DNA + DNAse I | − | − | − |
| Nel DNA + HpyCH4IV | − | − | − |
| Nel DNA + HpyCH4IV buffer | + | + | + |
| Nel DNA + SfoI | − | − | − |
| Nel DNA + SfoI buffer | + | + | + |
| Nel DNA + BglII | + | + | + |
| Nel DNA + BglII buffer | + | + | + |
| Ngo strains | | | |
| MS11 wt | + | + | + |
| MS11ΔpilT | − | − | − |
| MS11ΔpilE | − | − | − |
| MS11ΔcomP | − | − | − |

(+) Killing; (−) No killing.

Nel does not have plasmids (see, e.g., Swanson, J., J Exp Med, 1973. 137(3): p. 571-89). It was determined whether Nel chromosomal DNA kills Ngo. Method: chromosomal DNA from Nel, Ngo, Nme and E. coli was digested with RNAse A, extracted with phenol/chloroform/isopropanol, and washed twice with ethanol. All DNAs have an $OD_{260/280}$ ratio of ≥1.98 (highly pure). The DNAs were spotted (30 ng/uL) on a Ngo lawn to test killing activity.

Result: Only purified Nel DNA killed Ngo (Table 1). The purity of the DNA argues against the Trojan Horse theory, whereby an agent enters Ngo by "hitchhiking" on Nel DNA. Ngo, Nme and E. coli DNA did not kill Nel.

Neisseria are naturally competent and readily take up DNA. DNA uptake requires retraction of the Type IV pilus (Tfp) fiber and binding of ComP, a pilus-associated protein, to a 10-bp DNA uptake sequence (DUS) that is abundant in neisserial genomes (see, e.g., Swanson, J., J Exp Med, 1973. 137(3): p. 571-89; Wolfgang, M., et al., Mol Microbiol, 1999. 31(5): p. 1345-57; Berry, J. L., et al., PLoS Genet, 2013. 9(12): p. e1004014). Mutations in pilE, the Tfp fiber subunit gene (see, e.g., Merz, A. J., M. So, and M. P. Sheetz, Nature, 2000. 407(6800): p. 98-102); pilT, the Tfp retraction motor gene (see, e.g., Merz, A. J., M. So, and M. P. Sheetz, Nature, 2000. 407(6800): p. 98-102); and comP (see, e.g., Berry, J. L., et al., PLoS Genet, 2013. 9(12): p. e1004014; Cehovin, A., et al., Proc Natl Acad Sci USA, 2013. 110(8): p. 3065-70) abolish competence.

It was determined whether DNA uptake by Ngo is required for its susceptibility to killing by Nel supernate.

Method 1: Wt Ngo MS11, MS11ΔpilE, MS11ΔpilT and MS11ΔcomP were tested for susceptibility to killing by 24-hr cell free Nel supernates, using the agar plate assay. In MS11ΔcomP, a Kanamycin (Kan) resistance cassette has replaced comP; this in-frame mutation does not affect expression of flanking genes. Result: All mutants were resistant to supernate killing, unlike the wt strain (Table 1). Thus, DNA uptake by Ngo via Tfp/DUS is key to its suseptibility to killing by Nel supernate.

Method 2: Nel DNA was digested with restriction enzymes HpyCH4IV (which cuts in the DNA uptake sequence (DUS)), SfoI, or BglII, or incubated with buffer alone, and the samples were tested for killing activity using the plate assay. Result: HpyCH4IV and SfoI, but not BglII or any of the buffers, abolished killing activity (Table 1). The HpyCH4IV result strongly suggests that the lethal effect of Nel DNA on Ngo requires intact DUSs. The SfoI result suggests that at least one other enzyme abolishes the ability of Nel DNA to kill Ngo.

Example VI

This example demonstrates DNAse I prevents Nel killing of Ngo in liquid culture. It was determined whether DNAse I could protect Ngo from Nel killing in liquid culture.

Method: Nel and Ngo were preincubated separately with DNAse I (50 U/mL) or buffer for 30 min, then either mixed together or kept in separate tubes, and incubated for 5 hrs. DNAse I (50 U/mL) or buffer was added twice more to the tubes, at 2 and 4 hrs. Nel and Ngo cfus from three independent experiments were averaged and the median values compared using Students' t-test.

Result: In the mixed cultures, DNAse I increased Ngo viability ~20-fold over the buffer control (p<0.001). DNase I did not affect Nel cfus in the mixed cultures, or Nel or Ngo cfus in the monocultures. This firmly supports the agar plate assay findings, indicating Nel DNA is the agent that kills Ngo in liquid culture.

Example VII

This example demonstrates that Nel dramatically reduces Ngo cfus in the lower genital tract of mice and accelerates its clearance. Ngo does not cause disease in animals. A mouse model for studying Ngo colonization and adaptation in the female lower genital tract has been developed (see, e.g., Jerse, A. E., et al., Front Microbiol, 2011. 2: p. 107). In this system, Ngo persists in the mouse vagina for 10-12 days before it is cleared by the innate defense system. This model recapitulates many events in Ngo infection in humans: 1) cytokine/chemokine production, PMN recruitment, an unprotective antibody response, and induction/suppression of Th17/Th1/Th2 responses (see, e.g., Packiam, M., et al., Mucosal Immunol, 2012. 5(1): p. 19-29; Wu, H., A. A. Soler-Garcia, and A. E. Jerse, Infect Immun, 2009. 77(3): p. 1091-102); 2) human innate defenses (see, e.g., Packiam, M., et al., Mucosal Immunol, 2012. 5(1): p. 19-29; Wu, H., A. A. Soler-Garcia, and A. E. Jerse, Infect Immun, 2009. 77(3): p. 1091-102); and 3) Opa antigenic variation (see, e.g., Simms, A. N. and A. E. Jerse, Infect Immun, 2006. 74(5): p. 2965-74; Cole, J. G., N. B. Fulcher, and A. E. Jerse, Infect Immun, 2010. 78(4): p. 1629-41). Jerse's model is used to test the role of Ngo factors in protecting against host innate defenses (see, e.g., Wu, H., A. A. Soler-Garcia, and A. E. Jerse, Infect Immun, 2009. 77(3): p. 1091-102; Warner, D. M., et al., J Infect Dis, 2007. 196(12): p. 1804-12; Warner, D. M., W. M. Shafer, and A. E. Jerse, Mol Microbiol, 2008. 70(2): p. 462-78).

Whether commensal *Neisseria* antagonizes Ngo was determined using this mouse model. Nel strain 29315 was focused on because its genome is sequenced (see, e.g., Marri, P. R., et al., PLoS One, 2010. 5(7): p. e11835) and Ngo strain MS11 (see, e.g., Swanson, J., J Exp Med, 1973. 137(3): p. 571-89) because its host cell interactions are well studied. Both strains are resistant to Streptomycin ($Sm^R$) to allow colonization of Sm-treated mice, and both grow as well as their wt parents.

Method: Mice were inoculated in the vagina with Nel or Ngo alone, or Nel+Ngo. The vaginas were swabbed periodically and swab suspensions were plated on L agar+Sm for Nel colony forming units (cfus), and GCB agar+Vancomycin, Colistin, and Nalidixic Acid (VCN) for Ngo cfus.

Figure 5A:
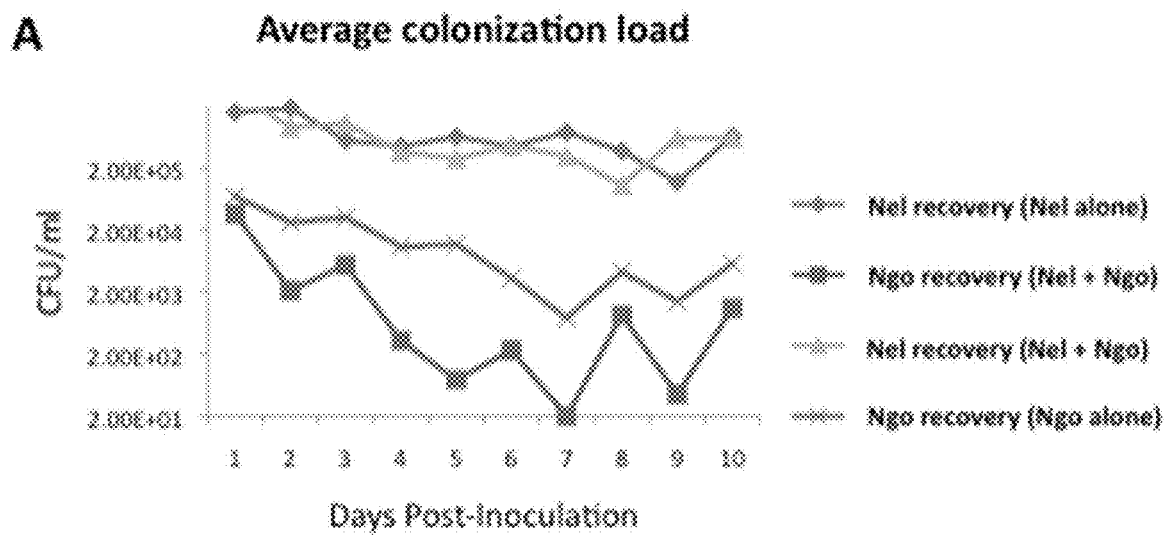
FIG. 5A and FIG. 5B: Ngo is cleared from mice more quickly when in the presence of Nel. The vagina of mice were inoculated with Ngo alone, or with a 50:50 ratio of Ngo and Nel and Ngo counts were measured over the course of 10 days.
Figure 5B:
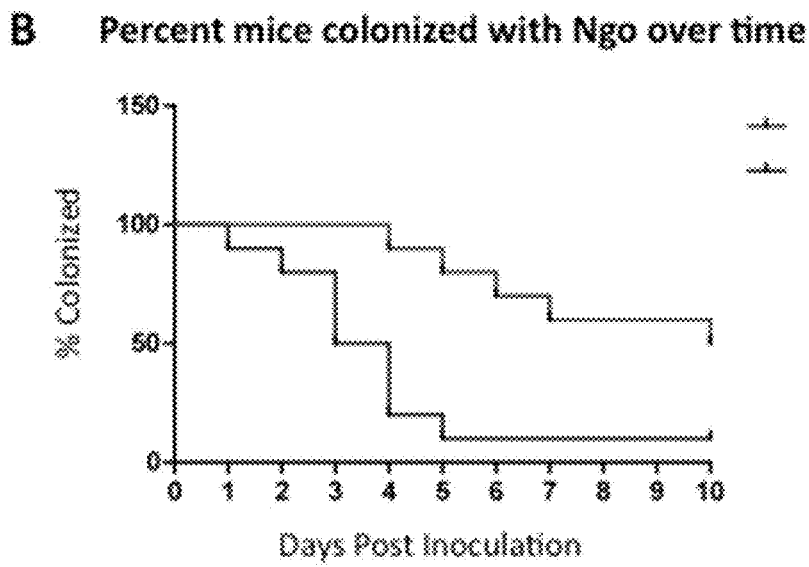
Figure 6A:
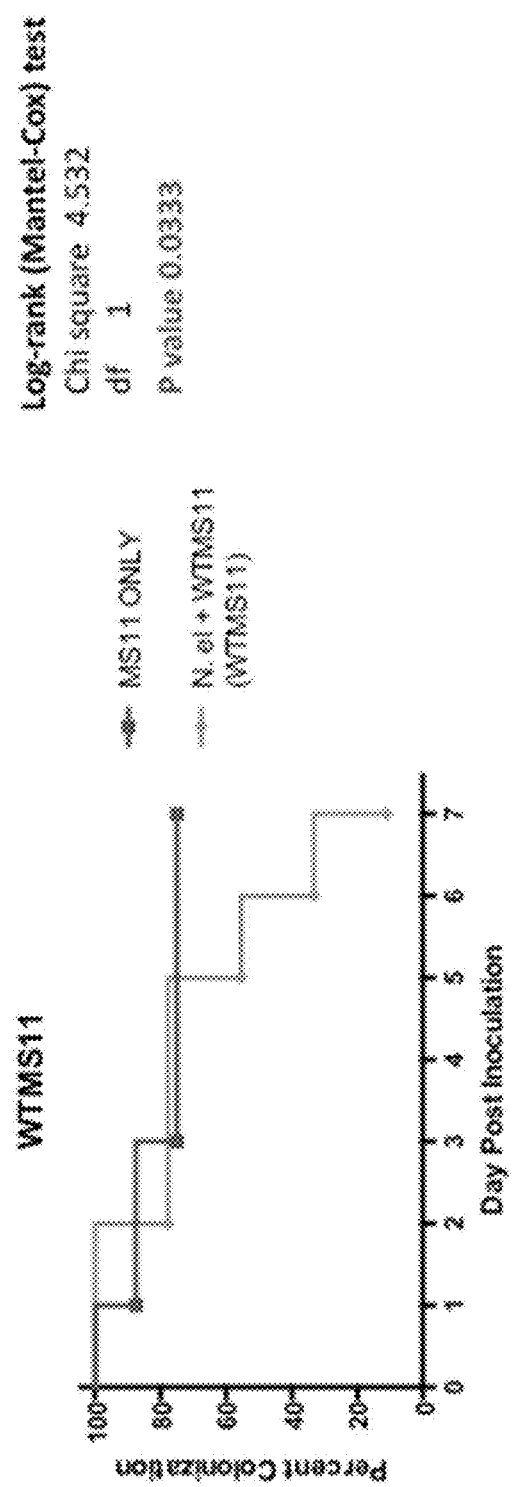
FIG. 6A and FIG. 6B: The DNA uptake mutant, Ngo ΔcomP, is resistant to Nel clearance from mice, compared to WT Ngo.
Figure 6B:
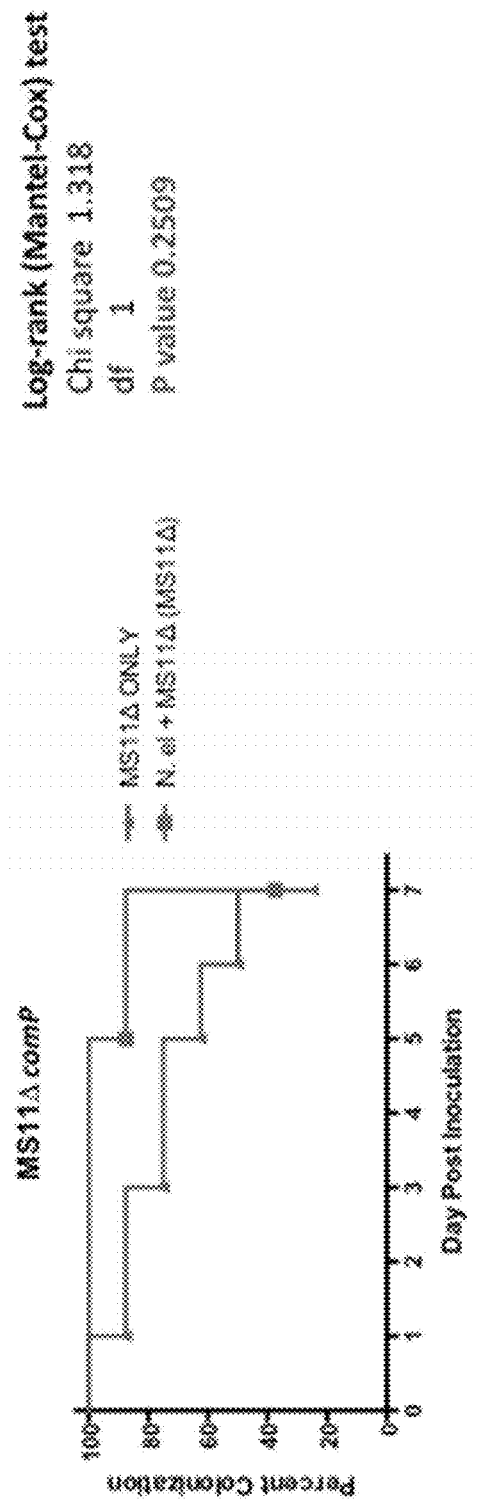

Result: Ngo was recovered at significantly lower levels from mice co-infected with Nel than mice inoculated with Ngo alone (FIG. 5A, red vs purple line). In addition, the duration of Ngo infection was significantly shorter in co-infected mice than mice infected with Ngo alone (3 days vs 7.7 days; FIG. 5B, blue vs red line). In co-infected mice, Ngo was cleared from 50% of the animals by day 3, and from 90% of the animals by day 5. In mice infected with Ngo alone, Ngo was recovered from 100% of the animals on day 3, and from 80% of the animals on day 5. In contrast, Nel was recovered from mice at high levels throughout the 10-day period whether Ngo was present or not (range of average cfu/ml: $1 \times 10^5$ to $3 \times 10^6$) (FIG. 5A). These results suggest that Ngo MS11 was cleared more quickly from mice when Nel was present.

That Nel colonizes the lower genital tract of female mice is a novel finding. It suggests the potential of this model for studying commensal *Neisseria* colonization, persistence and interactions with pathogens.

Example VIII

This example involves identification of the Nel locus/loci lethal for Ngo.

SmR strains of Nel 29315 (see, e.g., Swanson, J., J Exp Med, 1973. 137(3): p. 571-89) and Ngo MS11 (see, e.g., Swanson, J., J Exp Med, 1973. 137(3): p. 571-89) or their derivatives will be used in additional experiments. Both genomes are sequenced; both are piliated; Nel 29315 does not have opa genes; Ngo MS11 does not express Opa. Bacteria will be cultured in GCB medium+Supplements I/II or GCB agar.

Methods to identify the *N. elongata* locus/loci that kills Ngo have been identified. It involves identifying restriction enzymes that cut in the sequences crucial for killing Ngo, and matching the enzyme recognition sites to the restriction map of the *N. elongata* genome. Proof of principle for this method comes from the observations that Nel DNA kills Ngo when it is taken up by the pathogen, and its ability to kill is destroyed when it is digested with a restriction enzyme that cuts in the DUS.

Using the 2.26 Mb Nel 29315 genome sequence (see, e.g., Swanson, J., J Exp Med, 1973. 137(3): p. 571-89) as the starting point, restriction maps of the 53 contigs (the genome is not closed) will be constructed, using programs on the web. Nel DNA will be digested with 50 separate restriction enzymes (more if necessary), and the samples tested for Ngo killing activity using the agar plate assay. Enzyme selection will be guided by the restriction maps and by enzyme requirements.

Nel DNA will be extracted as described in Example V. DNA with $OD_{260/280}$ ratios ≥1.98 will be digested with enzymes per manufacturers' instructions, and spotted (30 ng/uL) on a lawn of Ngo MS11 to test for killing activity. Digestion will be monitored by agarose gel electrophoresis. Controls are: Nel DNA spiked with a plasmid containing a site for the enzyme to monitor digestion; Nel DNA incubated with buffer alone; enzyme alone; and *E. coli* DNA incubated with enzyme or buffer alone (*E. coli* DNA does not kill Ngo; Table 1). Three independent experiments will be performed.

DNAs allowing Ngo growth will be assigned a value of 1; enzymes in these samples are presumed to cut in the lethal locus or sequences important for its expression. DNAs that kill Ngo will be assigned a value of 0; enzymes in these samples are presumed not to interrupt these sequences. Scores for each enzyme will be tallied for all three experiments. A few enzymes will have a score of 3; most will have a score of 0. Enzymes with intermediate scores (e.g., score of 2; values of 1, 1, 0) will be retested, as the reactions may not have gone to completion. Enzymes and scores will be matched to the restriction map of each contig (FIG. 8).

A region with a cluster of high scoring enzymes and devoid of low scoring enzymes is presumed to contain a locus deleterious to Ngo. If the region is still very large, with many open reading frames, we will map it with additional enzymes, choosing ones that are in the restriction map of the contig. The region will be analyzed for determinants of cell death-inducing systems as discussed above and (see, e.g., Cascales, E., et al., Microbiol Mol Biol Rev, 2007. 71(1): p. 158-229; Makarova, K. S., Y. I. Wolf, and E. V. Koonin, Nucleic Acids Res, 2013. 41(8): p. 4360-77), and DUS. It is anticipated that one locus will be identified, two or more distinct loci, or multiple copies of the same locus, and a DUS within 1-2 kb of the locus/loci because of its abundance in neisserial genomes (see, e.g., Swanson, J., J Exp Med, 1973. 137(3): p. 571-89).

Experiments will be conducted to validate the results from above. The presumptively positive region(s) will be PCR amplified with flanking primers and directly assess the DNA for killing activity using the plate assay. PCR does not work well for very large regions of DNA; if faced with this situation, the presumptive positive region(s) will be cloned into a plasmid in *E. coli* and test the plasmid DNA for killing activity using the plate assay. The control is empty plasmid DNA. Subsequent subcloning and testing will pinpoint the sequences important for lethality.

A Nel mutant will be constructed that is deleted of the locus and complement the mutant, using standard protocols for *Neisseria* (see, e.g., Dillard, J. P., Curr Protoc in Microbiol, 2011 (Chapter 4:Unit4A.2)). Mutants have been successfully made in Nel. If multiple loci are identified, a mutant will be constructed with multiple deletions and a corresponding complemented strain. DNA from the mutant(s) and complemented mutant(s) will be tested for killing activity using the plate assay. The strains will also be co-cultured with Ngo (see Example II) to test their ability to kill the pathogen. The strains will be tested in mice, as described in (see, e.g., Jerse, A. E., et al., Front Microbiol, 2011. 2: p. 107) and below.

Large fragments of Nel DNA will be cloned into a plasmid vector in *E. coli*, and test plasmid DNAs for killing activity using the plate assay. Large fragments of Nel DNA will be generated by digestion with an enzyme with few sites in the Nel genome and which leaves the lethal locus intact (determined by the plate assay). Subsequent subcloning will pinpoint the locus/loci. Fragments will be inserted into a vector which accomodates large inserts, such as BAC (Bacterial Artificial Chromosome).

Example IX

This example involves determining whether Ngo DNA uptake mutants resist Nel clearing from mice.

The mouse model of Ngo genital tract infection was used to test whether uptake of Nel DNA by Ngo is the mechanism by which it is cleared in vivo. MS11☐comP was examined in particular. This mutant cannot bind to the neisserial DUS and therefore cannot take up neisserial DNA, but it behaves normally in Tfp biogenesis, twitching motility and infection of cultured cells (see, e.g., Wolfgang, M., et al., Mol Microbiol, 1999. 31(5): p. 1345-57; Berry, J. L., et al., PLoS Genet, 2013. 9(12): p. e1004014). MS11 ΔpilE or MS11 ΔpilT were not tested in mice as in vitro studies show MS11 ΔpilE does not attach to cells, and MS11 ΔpilT signals epithelial cells aberrantly, with consequences for later stages of infection (see, e.g., Merz, A. J. and M. So, Annu Rev Cell Dev Biol, 2000. 16: p. 423-57; Howie, H. L., S. L. Shiflett, and M. So, Infect Immun, 2008. 76(6): p. 2715-21). Neither ΔpilE nor ΔpilT has been tested in mice.

BALB/c mice (4-6 weeks old) were treated with 17β-estradiol and Streptomycin (Sm) using a standard protocol (Jerse, A. E., et al., Front Microbiol, 2011. 2: p. 107). Three groups of mice (8/group) were inoculated vaginally with a suspension containing similar numbers of Nel and either WT MS11, MS11 ΔcompP, or the complemented mutant MS11 ΔcomP+comP$_{wt}$. Control mice were inoculated with each strain alone. Vaginal swabs were collected daily for the duration of the experiment, and bacterial counts in swab suspensions were determined by plating on GC agar+Sm for Ng colony forming units (cfus), and Heart Infusion Agar (HIA) for Nel cfus. The duration of colonization of test and control groups were plotted as Kaplan Meier colonization curves and analyzed using the LogRank test. The cfus recovered over time in test and control groups were compared using a repeated measures ANOVA followed by a Bonferroni post-hoc analysis. For both sets of analyses, p<0.05 were considered significant. Experiments were performed at least twice to increase statistical power and test data reproducibility.

These experiments (see FIG. 5A-B, FIG. 6A-B, and FIG. 7A-B) show that WT MS11 colonized mice for a shorter period of time when Nel is present than when Nel is absent. ΔcomP persisted in mice for a longer period than WT MS11 whether Nel is present or not. MS11ΔcomP+comP$_{wt}$, the complemented mutant, behaved like the Wt strain, i.e., it colonized mice for a shorter period of time than the ΔcomP mutant.

The complemented mutant MS11ΔcomP+comP$_{wt}$ was constructed using standard *Neisseria* mutagenesis protocols (see, e.g., Dillard, J. P., Curr Protoc in Microbiol, 2011 (Chapter 4:Unit4A.2); Ramsey, M. E., et al., Appl Environ Microbiol, 2012. 78(9): p. 3068-78). The wt comP gene with an Erythromycin (Erm) cassette and a DUS downstream were introduced into an intergenic region of wt MS11 described previously (see, e.g., Dillard, J. P., Curr Protoc in Microbiol, 2011 (Chapter 4:Unit4A.2)). This construct also contained comP promoter elements. ΔcomP::Kan DNA was then transformed into this strain. The two loci were sequenced. All strains (wt MS11, MS11ΔcomP, and MS11ΔcomP+comP$_{wt}$) were tested for their ability to take up DNA and their growth curves examined.

Example X

This example demonstrated that Npo DNA kills Ngo. It was determined whether Npo DNA kills Ngo using an agar plate assay.

Positive control: Nel DNA, Kanamycin (Kan; 50 mg/uL)
Negative control: fresh sterile medium (GC medium)
NG=No growth; G=growth; SN=fresh undiluted Nel supernatant
Prep #=Nel supernate preparations with proven killing activity against Ngo MS11
Spot ID=position of spot on plate
Photo ID #=image of a plate or position of a plate containing the result

TABLE 2

| Spot ID | Sample | Concentration (ng/uL) | Photo ID # | Growth/No Growth | Photo ID # | Growth/No Growth |
|---|---|---|---|---|---|---|
| 1 | DNA Nel prep #7 | 60 | 100-6817 | NG | 100-6852 | NG |
| 2 | | 30 | 100-6816 | NG | 51 | NG |
| 3 | | 15 | 15 | NG | 50 | NG |
| 4 | | 7.5 | 14 | NG | 49 | NG |
| 5 | DNA Nel prep #10 | 60 | 24 | NG | 53 | NG |
| 6 | | 30 | 23 | NG | 54 | NG |
| 7 | | 15 | 22 | NG | 55 | NG |
| 8 | | 7.5 | 21 | NG | 56 | NG |
| 9 | DNA Npo | 60 | 41 | +/− | 57 | NG |
| 10 | | 30 | 40 | NG | 58 | NG |
| 11 | | 15 | 39 | NG | | NG |
| 12 | | 7.5 | 38 | NG | | +/− |
| C+ | Kanamycin | 5 mg/mL | 48 | NG | | NG |
| C− | GC medium | | 47 | G | | G |
| C+ | SN | | 46 | NG | | NG |

TABLE 3

| Spot ID | Sample | Concentration (ng/uL) | Photo ID # | Growth/No Growth |
|---|---|---|---|---|
| 1 | DNA Nel prep #7 | — | | |
| 2 | | 3.75 | [100-]6819 | G |
| 3 | | 1.875 | 18 | G |
| 4 | | 0.9375 | 20 | G |
| 5 | DNA Nel prep #10 | 3.75 | 25 | G |
| 6 | | 1.875 | 26 | G |
| 7 | | 0.9375 | 6827 | G |
| 8 | | — | | G |
| 9 | DNA N poly | 3.75 | [68]32/[68]42 | G |
| 10 | | 1.875 | 6833/[68]43 | G |
| 11 | | 0.9375 | [100-68]44 | G |
| 12 | | — | | |
| C+ | Kanamycin (5 mg/mL) | | | NG |
| C− | GC medium | | | G |
| C+ | SN | | [100-68]45 | NG |

Example XI

This example investigates whether a gene transfer between *N. elongata* and *N. gonorrhoeae* is responsible for Ngo inhibition during coinfection. In particular, Ngo inhibition was compared between a *N. gonorrhoeae* ΔcomP mutant that is unable to take up DNA compared and the wild type strain. Five groups of eight mice were tested in the following manner:

Group 1: *N. elongata* alone ($10^6$ CFU)

Group 2: Ngo strain MS11 Wild Type alone ($10^6$ CFU)

Group 3: Ngo strain MS11ΔcomP (mutant) alone ($10^6$ CFU)

Group 4: *N. elongata*+Ngo strain MS11 Wild Type ($10^6$ CFU)

Group 5: *N. elongata*+Ngo strain MS11ΔcomP ($10^6$ CFU)

Group 1, 2, & 4 inocula were prepared together for the *N. elongata* solo group, MS11 wild type solo group, and *N. elongata*+MS11 wild group. Group 3 & 5 inocula were prepared about 45 min later with a new batch of *N. elongata* for experiments with the MS11ΔcomP only and *N. elongata*+MS11ΔcomP groups.

Figure 7A:
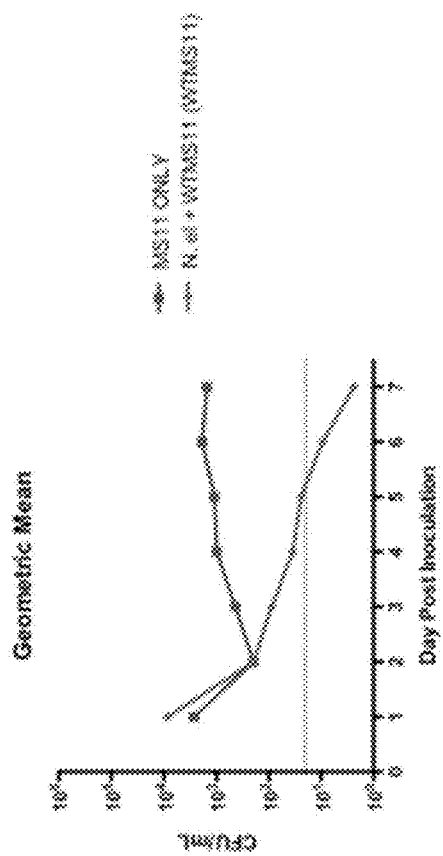
Figure 7A:
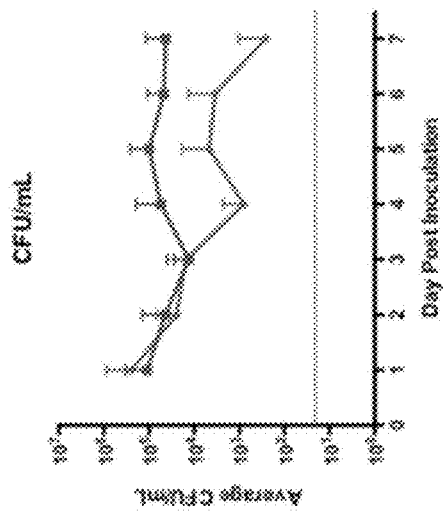

It was found that the MS11 ΔcomP mutant is able to survive during coinfection with *N. elongata*, but the wild type parent strain of Ngo is cleared at a significant rate when coinfected with *N. elongata* in vivo compared to infections with the wild type parent alone (see, FIGS. 5, 6 and 7). These results are consistent with the hypothesis that a DNA transfer from *N. elongata* to *N. gonorrhoeae* is responsible for *N. elongata*-mediated inhibition of Ngo in vivo.

Example XII

Figure 9A:
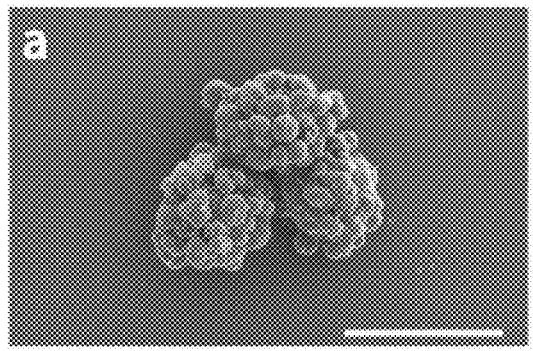
FIG. 9A-D: Nel and Ngo microcolonies associate with each other. Scanning electron micrograph of (FIG. 9A) Ngo and (FIG. 9B) Nel cultured alone, and (FIG. 9C, FIG. 9D) Ngo and Nel cultured together for 5 h. The image in (FIG. 9C) was pseudocolored to help discriminate Ngo (coccoid; yellow) and Nel (rods; blue).
Figure 9B:
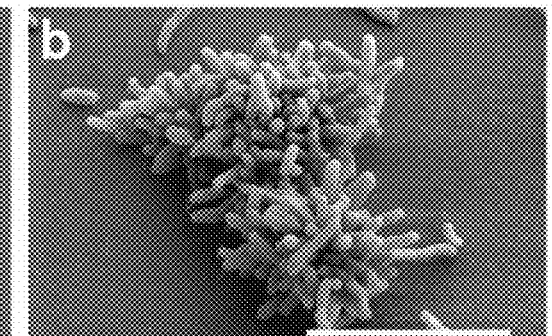
Figure 9C:
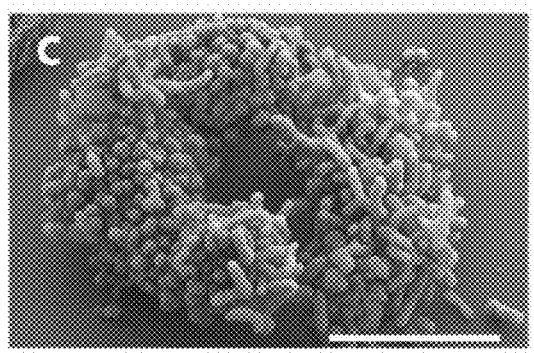
Figure 9D:
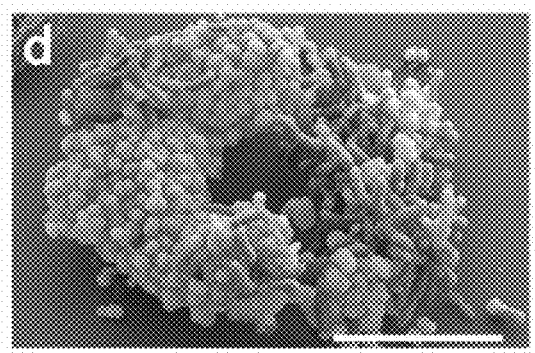

This Example demonstrates that Nel interacts physically with Ngo and kills the pathogen in vitro. Cultured alone, piliated Ngo and Nel cells actively aggregate into biofilm precursors known as microcolonies (Higashi et al., PLoS One 6, e21373 2011; Merz et al., Nature 407, 98-102 1999). To determine whether commensal and pathogen physically interact, planktonic Nel 29315 and Ngo MS11 (Table 6) cells were cultured alone or together on coverslips for 5 h, and viewed by Scanning Electron Microscopy (SEM). Representative images are shown in FIG. 9. The coccoid Ngo cells formed microcolonies with members of its own species (FIG. 9A). The majority of Nel cells, which are short rods, behaved similarly (FIG. 9B). Nel and Ngo microcolonies often abutted each other, and solitary Nel and Ngo cells were occasionally seen attached to or partially inserted into microcolonies of the other species (FIG. 9 C, D).

Figure 10:
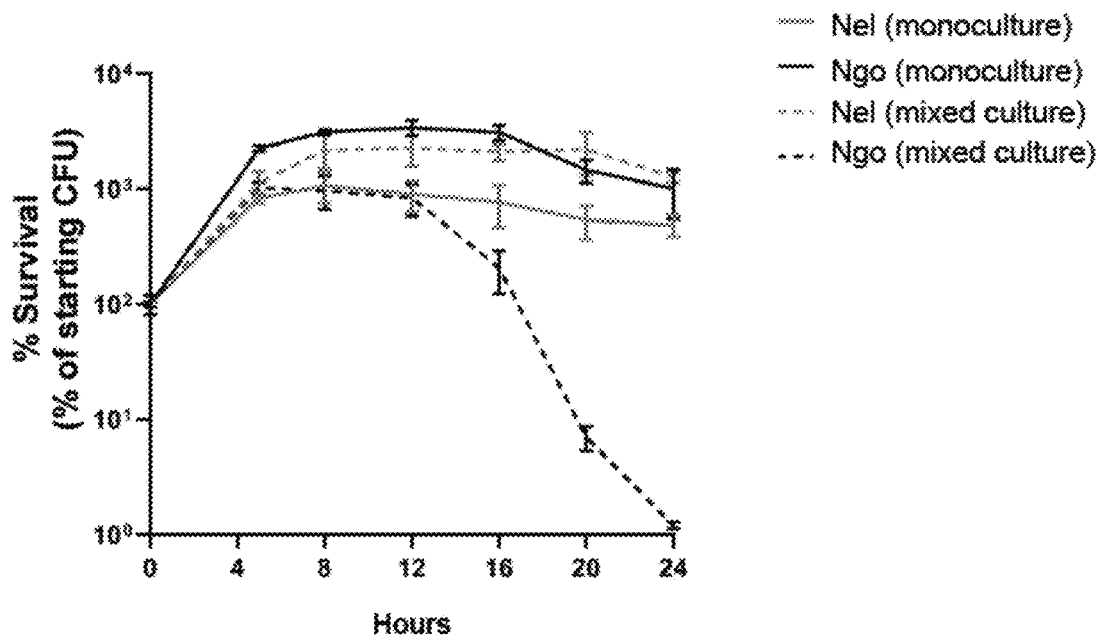
FIG. 10: Ngo kills Ngo in vitro. Ngo and Nel were cultured alone (~5×10$^7$ starting CFU) or together (~5×10$^7$ CFU each organism) in 6-well microtiter plates. At the indicated times, CFUs of each organism was determined by plating on selective agar.

Neither Nel 29315 nor Ngo MS11 lost viability when the two species were co-cultured for short periods (8 h) (Higashi et al., 2011, supra). To determine whether Nel and Ngo affected each other long term, commensal and pathogen were cultured alone or together for 24 h and their CFUs were determined by plating on selective agar. As reported, Nel CFUs in the monoculture reached stationary phase at 6 to 8 h (Rendon et al., Mol Microbiol 90, 103-113 2013). Its growth was unaffected by the presence of Ngo (FIG. 10). Ngo CFUs in the monoculture peaked at a similar time. In the presence of Nel, however, Ngo viable counts began to decline at 16 h; by 24 h they were 3 logs lower than those in the monoculture.

Figure 16:
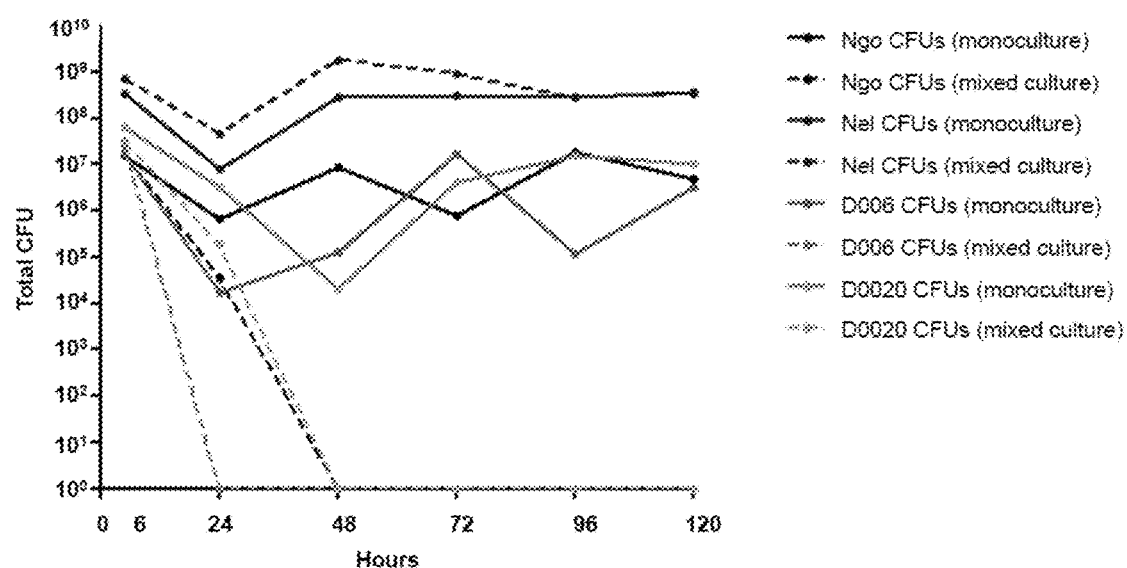
FIG. 16: Nel kills Ngo clinical isolates D006 and D020 in mixed culture. CFUs of Ngo clinical isolates D006 and D0020 and lab strain MS11 cultured alone (~5×10$^7$ CFUs total CFUs) or in the presence of Nel (~5×10$^7$ total CFUs each strain). Time of first plating: 6 h post-inoculation. Level of detection: 10 CFUs.

The experiment was repeated with Ngo strains D006 and D020, low passage strains isolated relatively recently from patients attending a county health department STD clinic (FIG. 16). In the presence of Nel, D006, D020 and MS11 CFUs were significantly reduced compared to CFUs recovered from monocultures. Like MS11, D006 and D020 did not affect Nel viability. These results show Nel kills lab and fresh isolates of Ngo.

Example XIII

Figure 11:
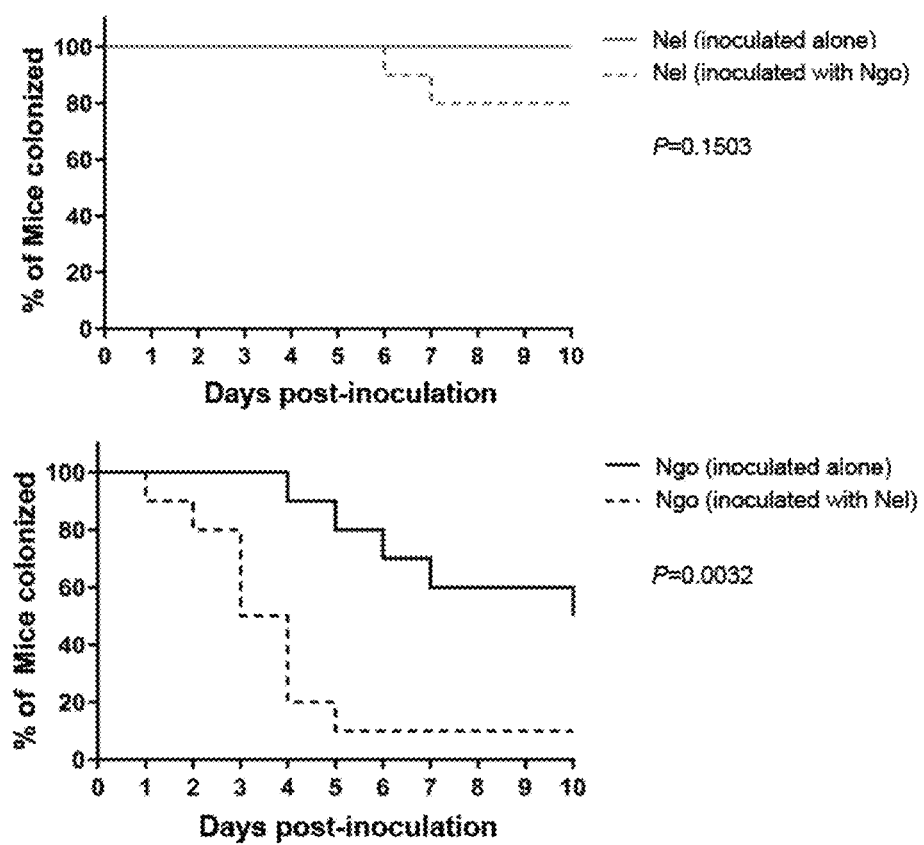
FIG. 11: Nel accelerates the clearance of WT Ngo from mice. Y-axis shows the percentage of mice culture-positive for Nel (left panel) and Ngo (right panel) at each time point, plotted as Kaplan Meier curves. n=8-9 mice/group.
Figure 17:
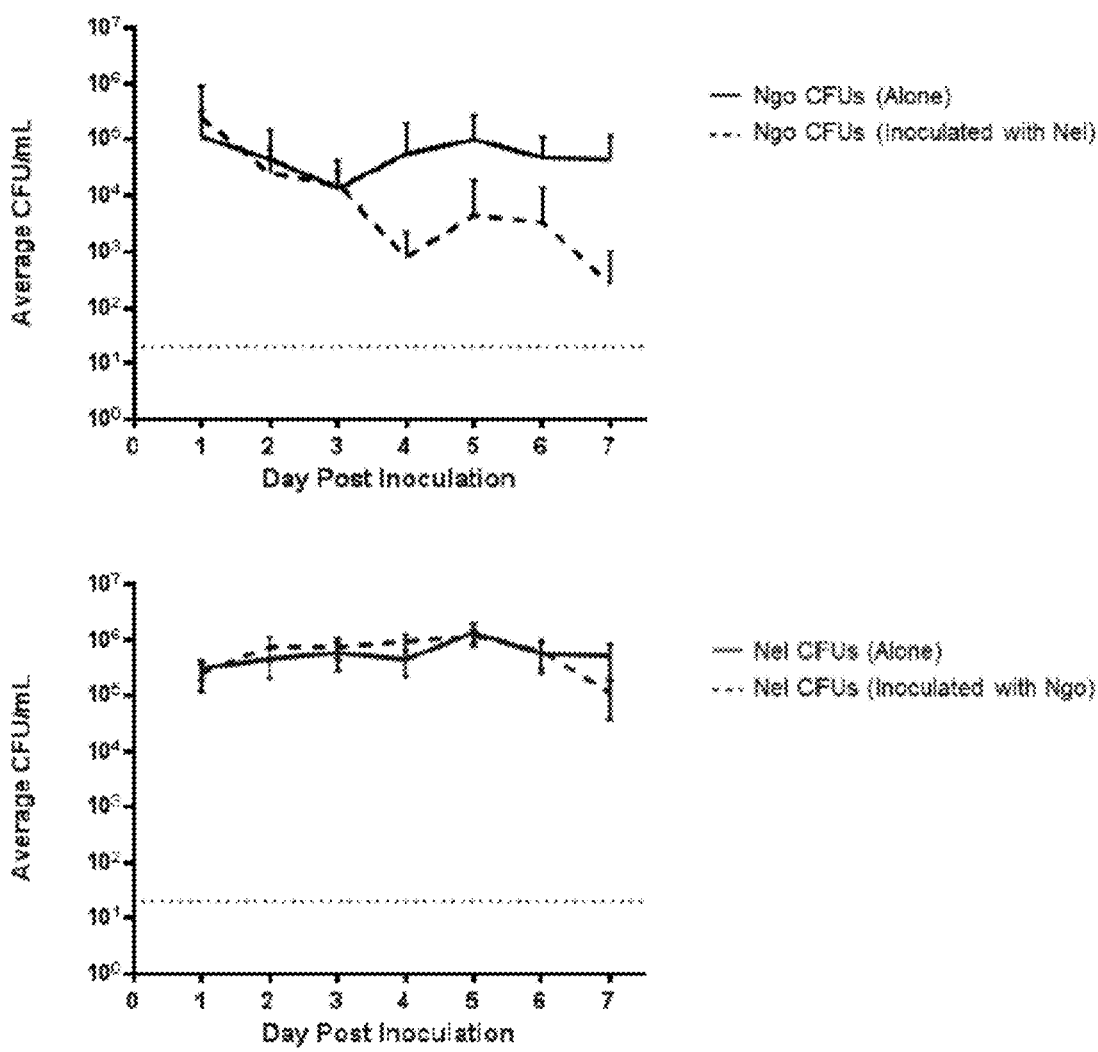
FIG. 17: Average CFU/mL of vaginal swabs in mice colonized by Ngo and Nel. Average number of Nel or Ngo CFUs recovered from 1 ml vaginal swab suspensions from mice inoculated vaginally with 106 CFU of Nel or Ngo alone or a mixture containing 106 CFU of each species. (n=8-9 mice/group). Dotted line indicates level of detection.

This Example demonstrates that Nel accelerates the clearance of Ngo in a mouse model of lower genital tract infection. To determine whether Nel affects Ngo colonization in vivo, an experiment was performed using the female BALB/c mouse model of lower genital tract infection (Jerse, Infect Immun 67, 5699-5708 1999; Jerse et al., Front Microbiol 2, 107 2011). Nel and Ngo were inoculated into the vagina of BALB/c mice either alone or mixed in equal numbers (FIG. 11). Commensal and pathogen CFUs were determined daily by plating vaginal swabs on selective agar. Nel colonized all mice throughout the experiment whether Ngo was present or not (FIG. 11, left panel). When inoculated alone, Ngo behaved as reported (Jerse, 1999, supra; Jerse et al., 2011, supra); it initially colonized all mice and was cleared from 50% of the animals by day 10. The presence of Nel significantly accelerated the clearance of Ngo from the animals (FIG. 11, right panel). In mice inoculated with Nel and Ngo, 50% of the animals were culture-positive for Ngo on day 4, compared to 90% of animals inoculated only with Ngo. By day 10, only 10% of mice in the Nel+Ngo group were colonized with Ngo compared to 50% of mice inoculated with Ngo alone (P=0.0032; log-rank test). The daily burdens of Nel and Ngo in the vagina, shown in FIG. 17, also illustrate the reduction in Ngo burden in co-inoculated mice.

Example XIV

Figure 12A:
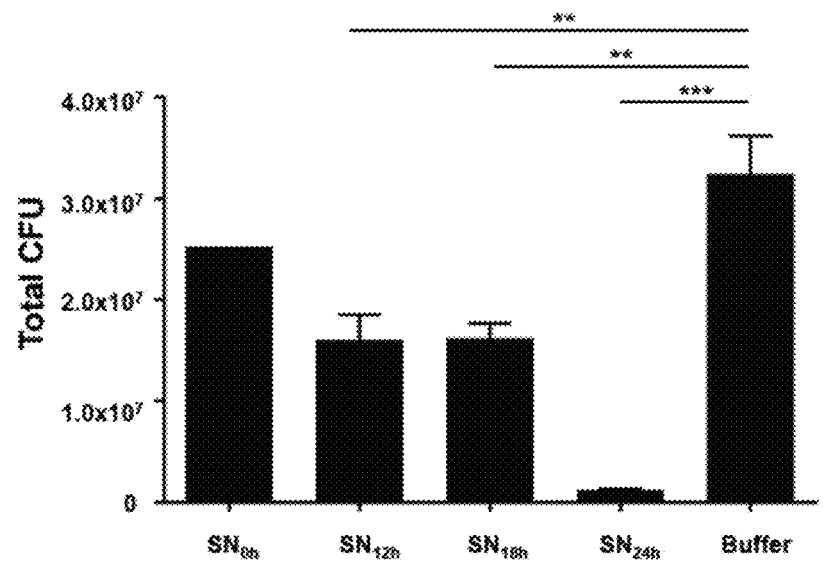
FIG. 12A-C: Cell-free Nel supernates (SN) and DNA kill Ngo.

This Example demonstrates that Nel kills Ngo through DNA it released into the medium. To determine whether Nel killing of Ngo requires cell contact, Ngo CFUs were determined after a 5-hr incubation with Nel cell-free supernatants (SN) (FIG. 12A). SN from 12 h and 18 h cultures significantly reduced Ngo viability compared to the GCB medium control (P<0.005, One-way ANOVA with Tukey's Multiple Comparison Test). The 24-h supernatant had the most dramatic effect, reducing Ngo CFUs by 27-fold (P<0.0001, One-way ANOVA with Tukey's Multiple Comparison Test). This indicates killing occurred through a component(s) that Nel released into the medium. The adverse effect of Nel supernatants on Ngo was unlikely to be caused by nutrient depletion, as the supernatants were diluted with an equal volume of fresh medium before the assay.

Figure 12B:
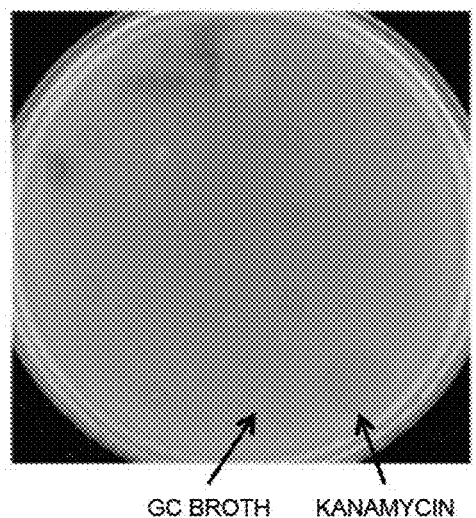

A spot assay was developed to provide a more rapid means of identifying the toxic compound(s) in Nel supernatants. Ngo cells were spread over an agar plate; supernatants were spotted on the lawn and the plate was incubated overnight. A zone of clearance on the lawn served as the readout for toxicity (FIG. 12B). Kanamycin and GC broth served as the positive and negative controls, respectively.

Figure 12C:
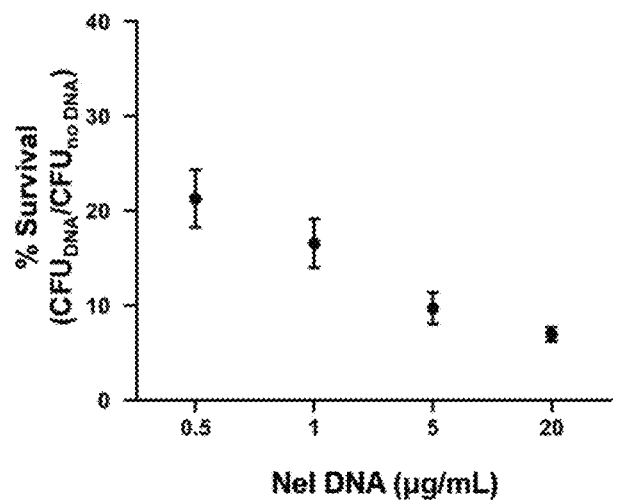

Supernatants from a 24-h culture of Nel were digested with various enzymes and tested for toxicity to Ngo using the spot assay. DNAse I abolished the toxicity of the supernatant for Ngo, while heat-inactivated DNAse I, and native and heat-inactivated Proteinase K and RNAse were still toxic (Table 4). This indicates that DNA is the killing agent. To verify that Nel DNA is the toxic component, Ngo was incubated with purified Nel chromosomal DNA, and its CFUs determined. Results from this liquid assay show Nel DNA killed Ngo in a dose-dependent manner (FIG. 12C).

TABLE 4

Identification of DNA as the toxic compound
in *N. elongata* supernates.

| Supernatant treatment | Clearance zone |
|---|---|
| DNAse I | No |
| DNAse I, boiled | Yes |
| Proteinase K | Yes |
| Proteinase K, boiled | Yes |
| RNAse I | Yes |

Example XV

Figure 13:
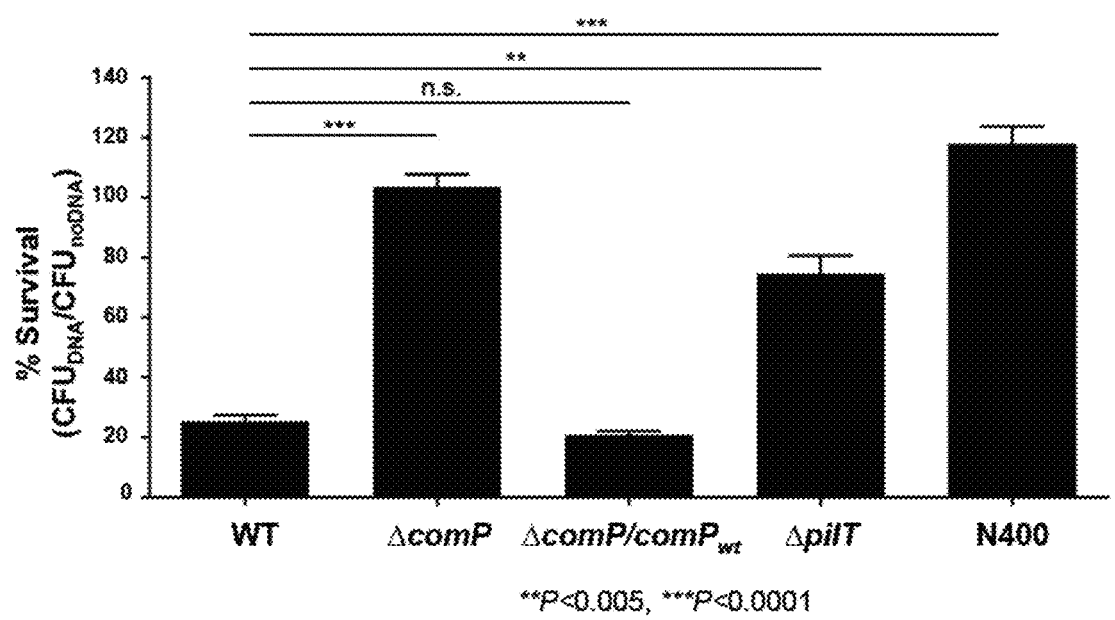
FIG. 13: Ngo DNA uptake/transformation mutants resist killing by Nel DNA. CFUs of Ngo strains incubated for 4 h with purified Nel DNA (20 ng/mL). WT: wild type Ngo; ΔcomP and ΔpilT: isogenic DNA uptake mutants of Ngo; ΔcomP (ΔcomP/comPwt): the complemented ΔcomP strain. N400: Ngo mutant whose recA is not expressed.

This Example demonstrates that Ngo DNA uptake mutants resist killing by Nel DNA. All *Neisseria* species examined to date are naturally competent and readily take up DNA in a sequence-specific manner. DNA uptake involves the binding of ComP, a Type IV pilus-associated protein, to a 10-base pair DNA Uptake Sequence (DUS; 5' GCCGTCT-GAA 3' (SEQ ID NO:3)) that is abundant in *Neisseria* genomes; in Ngo there is ~1 DUS/kb of DNA (Berry et al., PLoS Genet 9, e1004014 2013; Elkins et al., J Bacteriol 173, 3911-3913 1991; Marri et al., PLoS One 5, e11835 2010). DNA uptake also requires the Type IV pilus retraction motor PilT (Craig and Li, Curr Opin Struct Biol 18, 267-277 2008; Merz et al., Nature 407, 98-102 2000; Wolfgang et al., Mol Microbiol 29, 321-330 1998a). Ngo ΔcomP and ΔpilT transform at 3 to 5 log lower frequency than the WT parent (Wolfgang et al., Proc Natl Acad Sci USA 95, 14973-14978 1998b; Wolfgang et al., Mol Microbiol 31, 1345-1357 1999). In the spot assay, Ngo ΔcomP and ΔpilT were resistant to Nel DNA killing, while the complemented ΔcomP strain was as sensitive to killing as the WT parent (Table 5). In the liquid assay, all Ngo ΔcomP cells and 75% of ΔpilT cells survived exposure to Nel DNA. By contrast, only 25% of WT Ngo cells and 21% of complemented comP cells survived Nel DNA killing (P<0.0001 WT vs ΔcomP, P<0.005 WT vs ΔpilT, One-way ANOVA with Tukey's Multiple Comparison Test) (FIG. 13).

DNA taken up by *Neisseria* recombines with homologous sequences in the genome in a RecA-dependent manner, and Ngo ΔrecA is deficient in DNA transformation (Koomey and Falkow, J Bacteriol 169, 790-795 1987; Koomey et al., Genetics 117, 391-398 1987). Ngo N400 (Tonjum et al., Mol Microbiol 16, 451-464 1995), a recA non-expressing mutant, survived killing by Nel DNA (P<0.0005, One-way ANOVA with Tukey's Multiple Comparison Test) (FIG. 13). The resistance of N400, ΔcomP, and ΔpilT to DNA killing indicates that the killing mechanism involves the DNA uptake/transformation machinery. The results argue against the clumping hypothesis in which the decrease in CFUs reflects Ngo cells aggregating through DNA.

TABLE 5

Resistance of *N. gonorrhoeae* mutants
to killing by *N. elongata* DNA.

| Ngo mutants | Clearance zone |
|---|---|
| WT | Yes |
| ΔpilE | No |
| ΔcomP | No |
| ΔcomP/comP$_{wt}$ | Yes |
| ΔpilT | No |

Example XVI

Figure 14A:
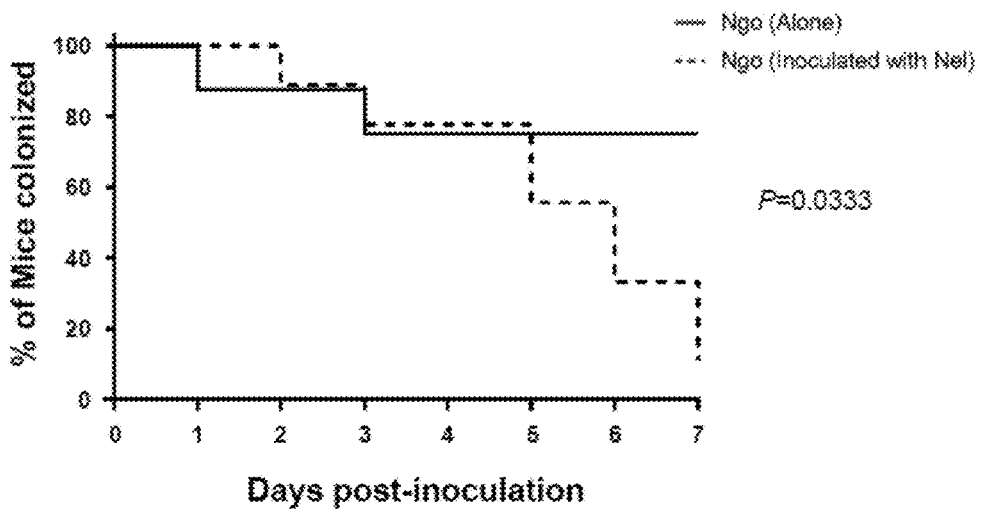
FIG. 14A-C: Nel does not accelerate the clearance of Ngo ΔcomP from mice. Y-axis shows the percentage of mice culture-positive for each strain over 7 days.
Figure 14B:
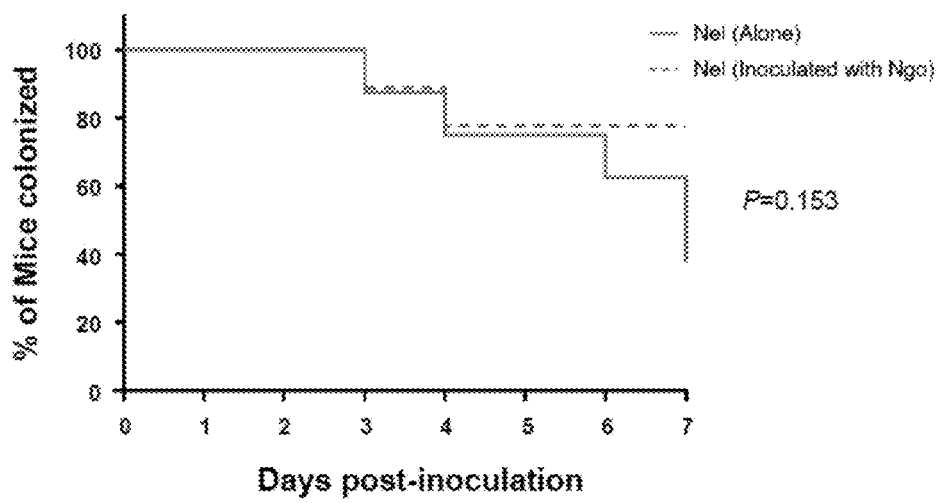
Figure 14C:
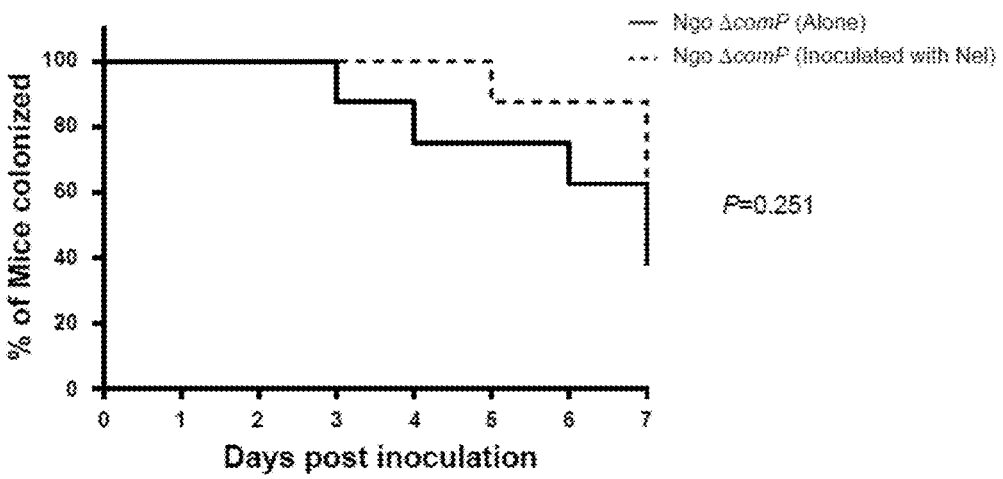

This Example demonstrates that Ngo ΔcomP resists Nel-accelerated clearance from the mouse. Ngo ΔcomP was tested for its ability to resist Nel clearance from the lower genital tract of the mouse. ΔcomP was inoculated into the vagina alone or with Nel in equal numbers. CFUs of each strain were quantitated daily. As observed above, Nel accelerated the clearance of WT Ngo (P=0.0333, log-rank test) (FIG. 14A). Furthermore, the duration of recovery of Nel from the mouse vagina was similar regardless of whether it was inoculated alone or together with Ngo, indicating Ngo did not influence Nel colonization (P=0.153; log-rank test) (FIG. 14B). In contrast, Nel did not accelerate the clearance of Ngo ΔcomP (P=0.251, log-rank test) (FIG. 14C), indicating that Nel accelerates Ngo clearance only if the pathogen is competent for DNA uptake.

Example XVII

Figure 18:
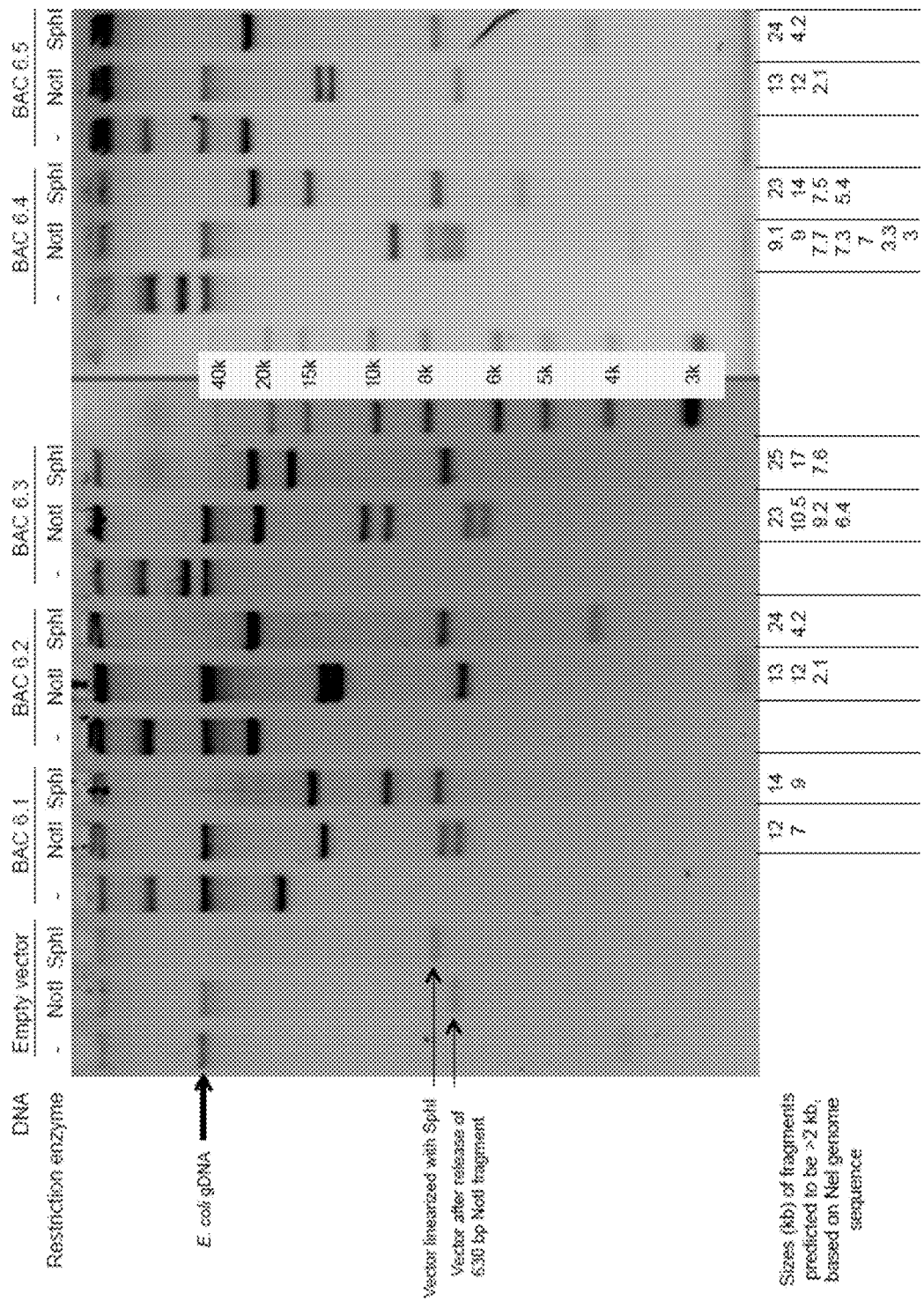
FIG. 18: Restriction analysis of BAC clones confirms DNA sequence data. Digestion of empty vector pBelo-BAC11 or pBeloBAC11 clones (6.1-6.5) containing inserts from the Nel genome. Expected fragment sizes (bottom) were determined by locating the sequenced BAC inserts relative to the reference Nel genome (RefSeq NZ_CP007726.1). Thick arrow indicates the position of the remnant of *E. coli* DNA after BAC purification. Top thin arrow indicates the position of the vector linearized with SphI. Bottom thin arrow indicates the position of the vector after release of 630 bp DNA fragment between the two NotI sites.

This Example demonstrates that Nel DNA does not kill Ngo via a "toxic" locus. To determine whether Nel DNA toxicity is conferred by a specific gene/genetic element, a library of Bacterial Artificial Chromosomes (BACs) containing 20-50 kb inserts of Nel DNA was constructed in *E. coli* using the vector pBeloBAC11. The inserts were sequenced and verified by restriction analysis (FIG. 18), and DNAs from several BACs with unique inserts were tested for their ability to kill Ngo in the liquid assay. All tested BAC DNAs, but not empty vector, were toxic to Ngo (Table 8). Overlapping fragments of the insert in the BAC clone pBeloBAC11(6.1), subcloned into pUC19, also killed Ngo. It is unlikely that there is a toxic locus in all tested BACs and pBeloBAC11(6.1) subclones, because these clones did not have sequences in common except for the DUS.

Figure 15A:
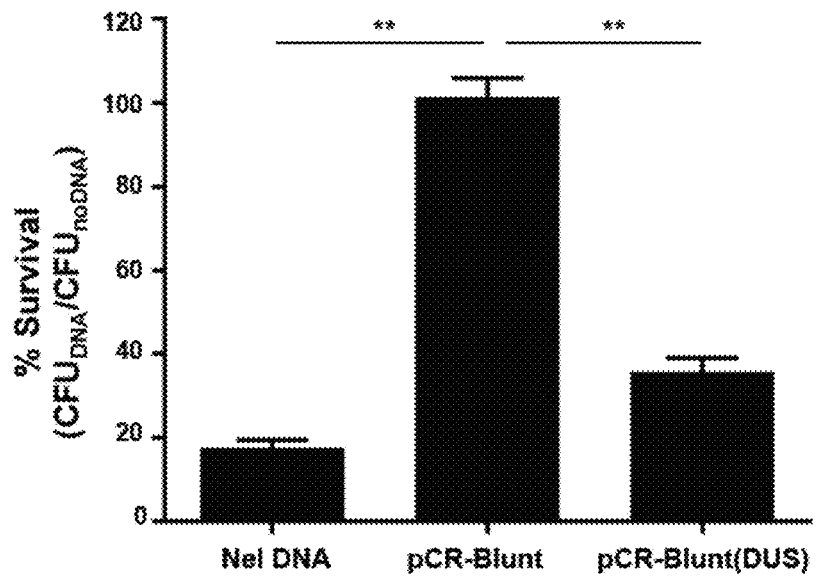
FIG. 15A-F: Ngo MS11 is killed when it takes up DNA with a different methylation pattern.
Figure 15B:
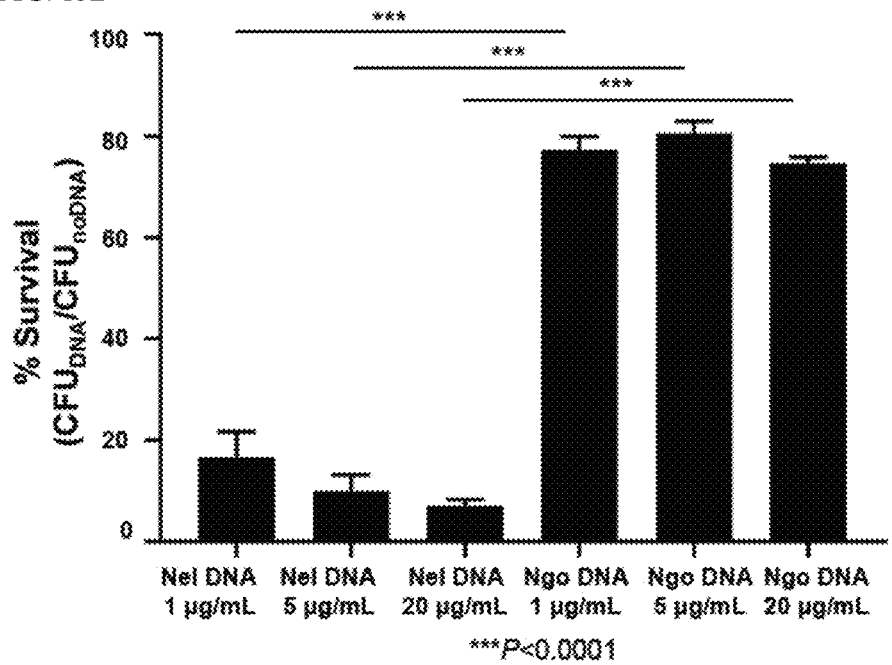

It was determined whether the DUS is a toxic sequence. *E. coli* plasmid pCR-Blunt DNA did not kill Ngo unless it contained a DUS (FIG. 15A). DUS is abundant in *Neisseria* genomes (Marri et al., PLoS One 5, e11835 2010); in the Ngo chromosome, there is ~1 DUS/kb of DNA. Yet, Ngo is not killed when incubated with its own DNA (FIG. 15B). Taken in context with the BAC cloning data, these results indicate that the DUS is not a toxic sequence.

TABLE 8

Toxicity of DNA from BACs and BAC
subclones for *N. gonorrhoeae*.

| | Insert start position | Insert end position | Insert length (bp) | Clearance zone |
|---|---|---|---|---|
| BAC clones | | | | |
| pBeloBAC11 vector (7.5 kb) | — | — | 0 | No |
| 6.1 | 1021119 | 1044807 | 23688 | Yes |
| 6.2 | 2097448 | 2126542 | 29094 | Yes |
| 6.3 | 1193060 | 1242918 | 49858 | Yes |
| 6.4 | 1030576 | 1081623 | 51047 | Yes |
| 6.5 | 2097448 | 2126542 | 28358 | Yes |
| BAC 6.1 subclones | | | | |
| pUC19 vector (2.7 kb) | — | — | 0 | No |
| 6.1.3 | 1024777 | 1029727 | 4950 | Yes |
| 6.1.11 | 1033760 | 1038767 | 5007 | Yes |
| 6.1.13 | 1042473 | 1044193 | 1720 | Yes |
| 6.1.20 | 1021144 | 1024413 | 3269 | Yes |

TABLE 8-continued

Toxicity of DNA from BACs and BAC subclones for *N. gonorrhoeae*.

| | Insert start position | Insert end position | Insert length (bp) | Clearance zone |
|---|---|---|---|---|
| 6.1.24 | 1039200 | 1044555 | 5355 | Yes |
| 6.1.26 | 1031310 | 1038748 | 7438 | Yes |

Example XVIII

This Example demonstrates that the methylation state of the DNA determines its toxicity for Ngo. The lack of evidence for a toxic locus in Nel DNA led to a determination of whether an epigenetic feature of the DNA is responsible for killing Ngo. Bacteria modify their DNA by means of methyltransferases that covalently link methyl groups to bases in specific sequences (Noyer-Weidner M., 1992 Methylation of DNA in prokaryotes. in DNA methylation: molecular biology & biological significance. eds Jost J. P., Saluz H. P. (Birkhauser, Basel, Switzerland). 39-108). Among bacteria, the Ngo genome is one of the most heavily methylated; Ngo strains encode/express 14-19 DNA methyltransferases (Blow et al., PLoS Genet 12, e1005854 2016; Roberts et al., Nucleic Acids Res 43, D298-299 2015; Stein et al., Gene 157, 19-22 1995) (tools.neb.com/genomes/index.php?page=N). PacBio Single Molecule, Real-Time (SMRT) sequencing of Ngo FA1090 DNA revealed the methylation patterns consistent with the activity of 10 methyltransferases (Blow et al., 2016, supra; Roberts et al., 2015, supra). In Ngo MS11, the activity of at least 7 of these methyltransferases has been demonstrated experimentally (Gunn et al., J Bacteriol 174, 5654-5660 1992) (Table 9). Commensal species of *Neisseria*, by contrast, encode fewer DNA methyltransferases. In particular, Nel isolates encode 7-10 predicted methyltransferases. Single Molecule, Real-Time (SMRT) sequencing of Nel 29315 DNA indicates 3 methyltransferases are active in this strain (Table 6). These methyltransferases modify sequence motifs that are not modified in Ngo (Table 6 and 9). These findings indicate Ngo and Nel DNA have distinct methylation patterns.

Figure 15C:
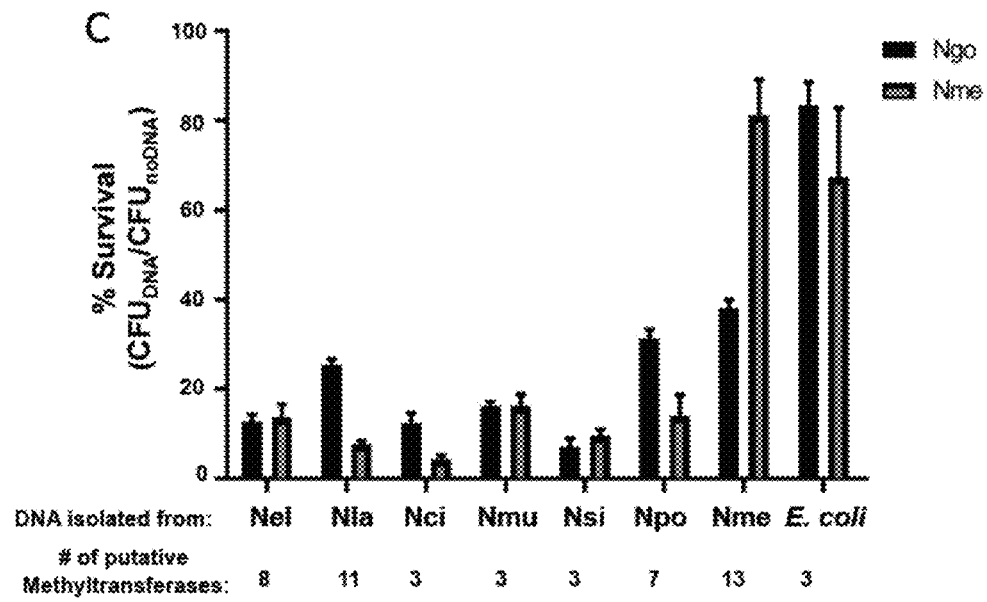

That commensal *Neisseria* encode fewer DNA methyltransferases than Ngo (Roberts et al., 2015, supra) (tools.neb.com/genomes/index.php?page=N) led to a test of their chromosomal DNA for toxicity to Ngo. DNA from *N. lactamica* (Nla), *N. cinerea* (Nci), *N. mucosa* (Nmu), *N. sicca* (Nsi), *N. polysaccharea* (Npo), and *N. meningiditis* (Nme) all significantly reduced Ngo viability (FIG. 15C). The putative number of DNA methyltransferases specific to the *Neisseria* strains used in this study is listed under the strain names. *E. coli* DH5a expresses only 3 methyltransferases (Table 10). In contrast to commensal *Neisseria* DNA however, *E. coli* DNA, with 1000-fold fewer copies of the DUS, did not affect Ngo viability. These results are consistent with the hypothesis that Ngo is killed when it takes up DNA whose methylation state is different from its own.

Figure 15D:
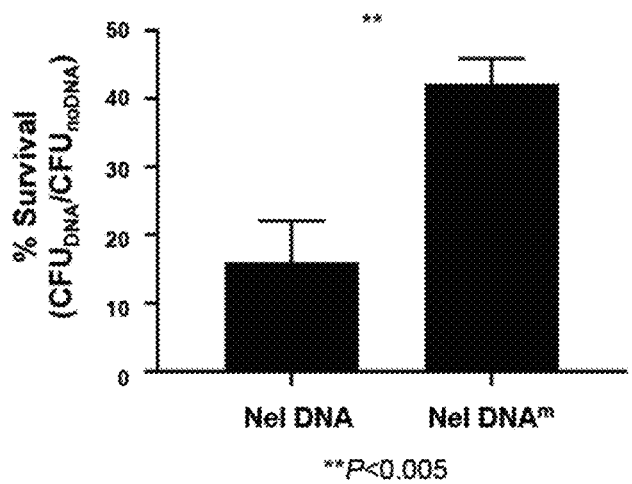
Figure 19:
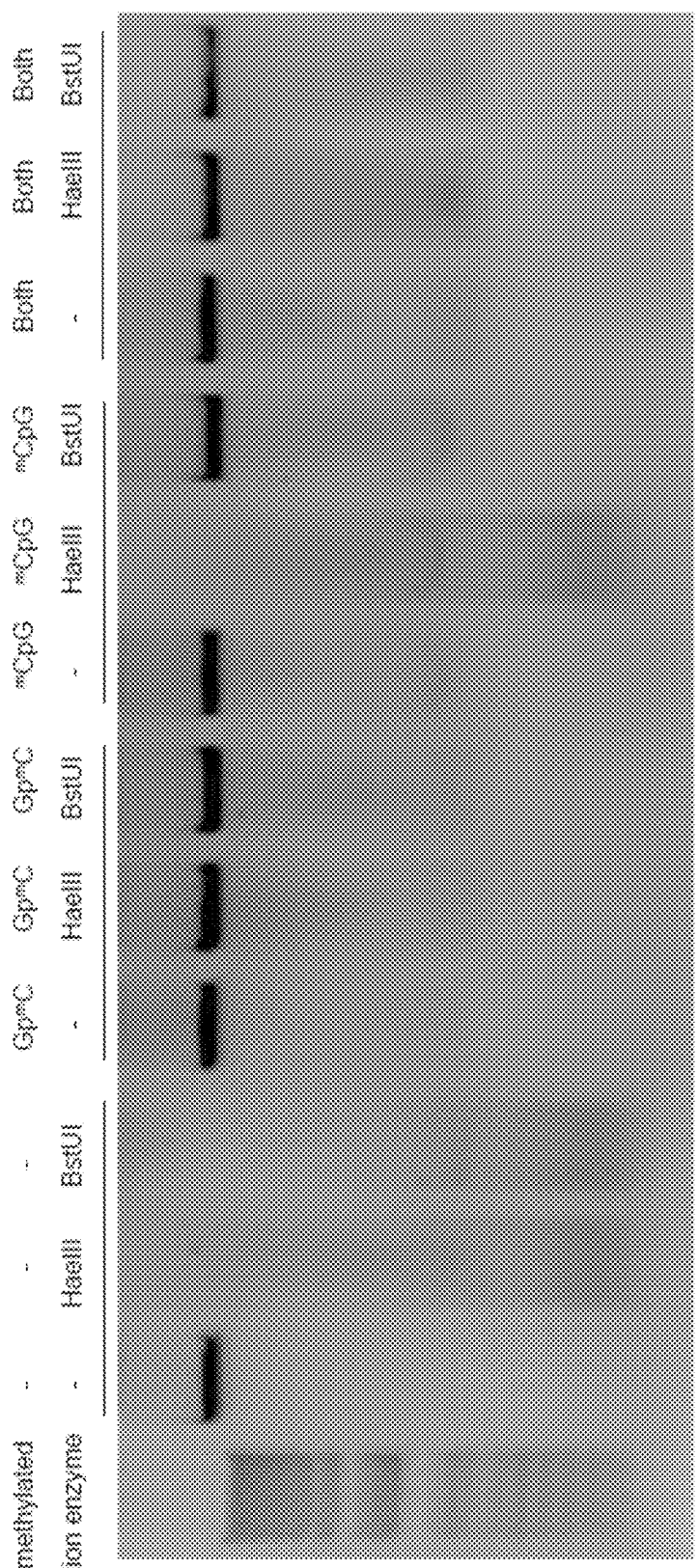
FIG. 19: Restriction digestion of Nel DNA confirms the methylation of GpC and CpG sequences. Purified Nel DNA was incubated with buffer or M.CviPI and/or M.SssI methyltransferases, and subsequently digested with HaeIII or BstUI, restriction enzymes which cleave only unmethylated GGCC and CGCG sequence, respectively.

It was determined whether modifying Nel DNA to partially mimic the Ngo methylation pattern would abolish its toxicity for Ngo. Several Ngo DNA methyltransferases modify cytosines in CpG and GpC motifs (Table 9). The cytosines in CpG and GpC sequences in Nel DNA were methylated in vitro using M.CviPI and M.SssI, respectively; methylation was verified by confirming the resistance of the modified DNA to digestion by the cognate restriction enzymes (FIG. 19). Modified DNA was significantly less toxic to Ngo than unmodified DNA (P<0.005; Student's t-test, FIG. 15D). This indicates that the toxicity of DNA is determined, at least in part, by differences in the methylation state of the incoming DNA and the recipient Ngo cell.

Figure 15E:
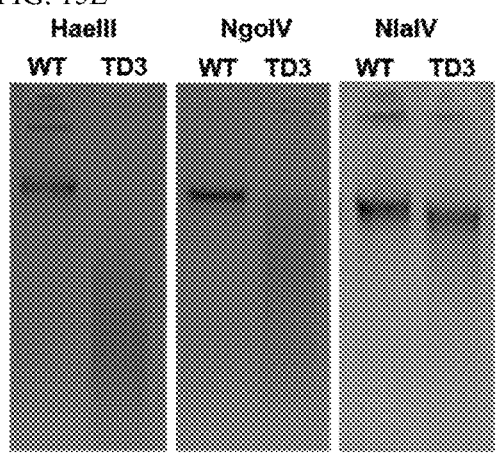

Ngo is not killed when incubated with its own DNA (FIG. 15B). If the methylation state of the incoming DNA is at the root of the toxicity, then undermethylated Ngo DNA would kill more efficiently than native Ngo DNA. To test this hypothesis, Ngo TD3, a mutant deleted of the ngoII, ngoIV, and ngoV restriction/modification (R/M) loci, was constructed. The mutations were verified by sequencing, and loss of methyltransferase activity was verified by confirming the susceptibility of TD3 DNA to digestion with the cognate restriction enzymes (FIG. 15E). As expected, HaeIII (an isoschizomer of NgoII, with 4783 sites in Ngo genome) digested TD3 DNA into smaller fragments than NgoIV (1600 sites) or NlaIV (an isoschizomer of NgoV, 1937 sites) (FIG. 7E). In addition, the partial digestion of TD3 by NlaIV is likely explained by the activity of methyltransferase NgoIII, which modifies sequences within the NlaIV site (6, Table FIG. 15E). TD3 DNA was slightly more toxic to Ngo than WT DNA (Ngo survival in the presence of WT Ngo DNA: 89.7%+/−2.10 SEM; of TD3 DNA: 79.8%+/−1.34 SEM; P<0.0182, Student's t-test). In TD3, only 3 R/M loci were deleted, which likely explains the mild difference in toxicity of its DNA.

As a final test of the importance of methylation in determining the toxicity of DNA for Ngo, a DNA fragment of Ngo origin with either an *E. coli* or Ngo methylation signature was tested for toxicity to Ngo. The 4 kb iga gene in Ngo was modified by insertion of a recognition site for restriction enzyme AsiSI and a DUS into its 5' and 3' ends (FIG. 7F, top panel). In this mutant, Ngo i35A, the order of this locus is 5' AsiSI-DUS-iga-DUS-AsiSI 3' (ADIDA for short). There are few AsiSI sites in the WT Ngo chromosome; the smallest AsiSI fragment is >15 kb. In i35A, the smallest AsiSI fragment is the ~4 kb ADIDA. i35A DNA was digested with AsiSI and separated in an agarose gel and DNA migrating at 4 kb, which contains only ADIDA, was purified.

Figure 20:
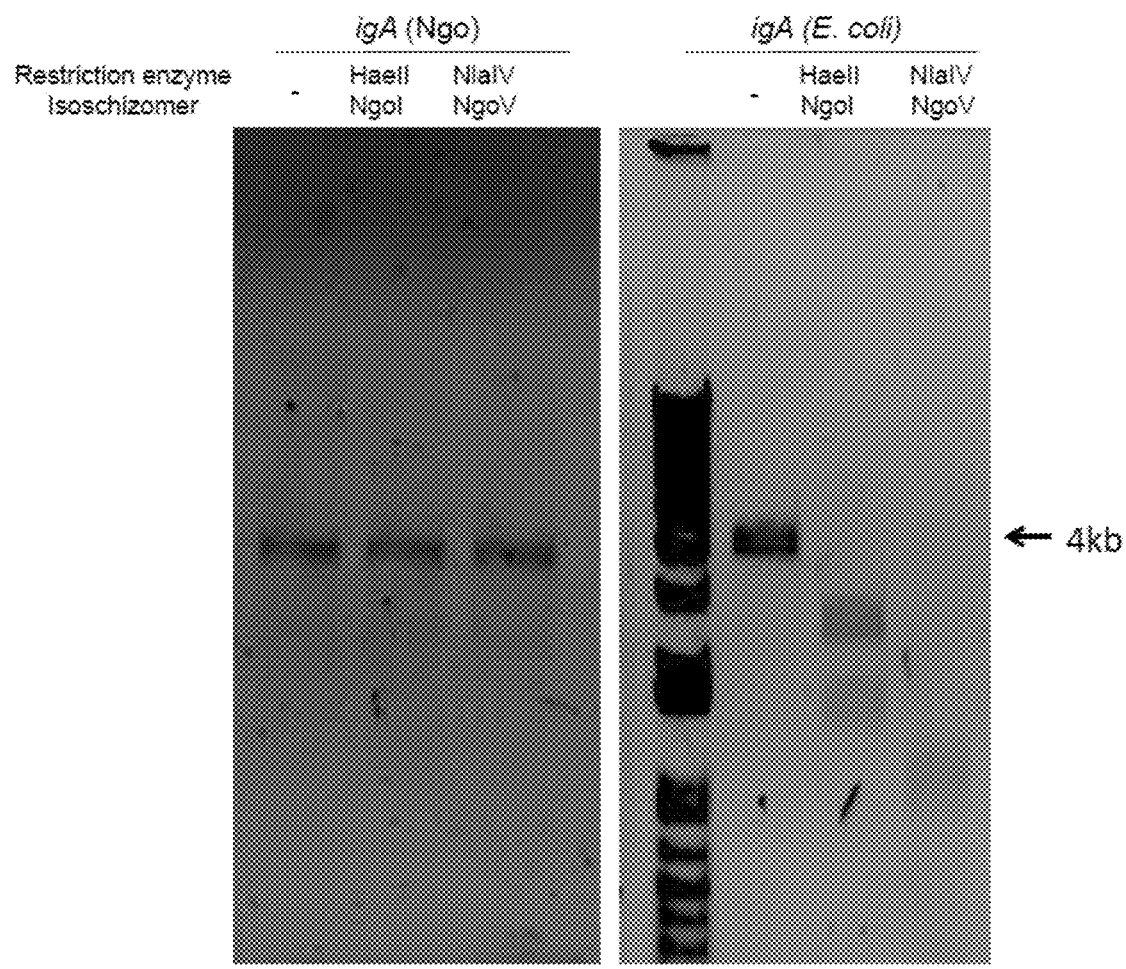
FIG. 20: Ngo restriction enzymes digest ADIDA DNA with *E. coli* but not Ngo methylation signature. ADIDA DNA fragment derived from Ngo i35A (left) and *E. coli* K-12 (right) digested with HaeII or NlaIV (isoschizomers of NgoI and NgoV) and separated in a 0.7% agarose gel. (−) indicates incubation with buffer alone.

Concurrently, ADIDA was replicated in *E. coli* DH5a, which expresses 3 DNA methyltransferases, and the insert was gel purified. ADIDA (*E. coli*) and ADIDA (Ngo) would have distinct methylation patterns since their hosts express DNA methylases with different specificities. This was verified by restriction analysis. iga contains NgoI and NgoV recognition sites. The ADIDA (*E. coli*) was susceptible to digestion by HaeII and NlaIV (isoschizomers of NgoI and NgoV), whereas ADIDA (Ngo) was resistant to restriction (FIG. 20).

Figure 15F:
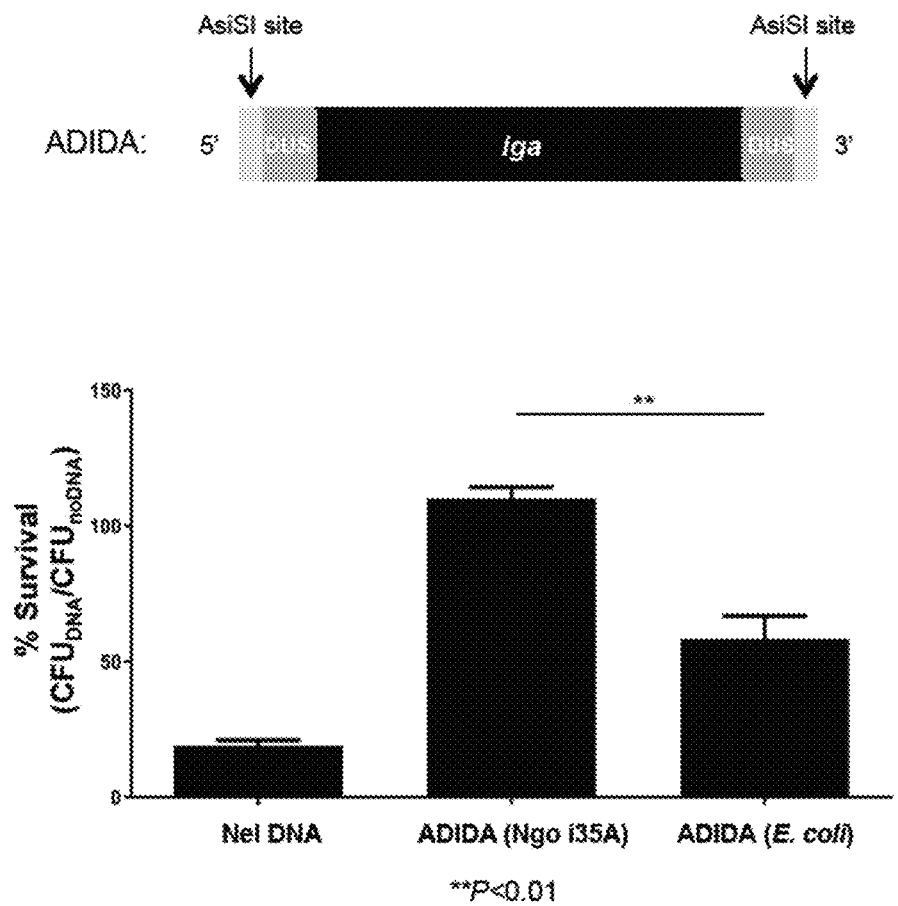

ADIDA with *E. coli* and i35A methylation signatures were evaluated for their ability to kill Ngo. ADIDA (*E. coli*) killed Ngo significantly more efficiently than ADIDA (Ngo i35A) (P<0.01; Student's t-test; FIG. 15F, bottom panel). ADIDA (*E. coli*) did not kill Ngo as efficiently as Nel chromosomal DNA, the positive control, most likely because it was used at a lower concentration in the assay and has a much lower sequence complexity than Nel chromosomal DNA (see Tables 11 and 12). These experiments demonstrate that Ngo is killed when it takes up DNA with a methylation pattern it does not recognize.

TABLE 6

Resistance of N. gonorrhoeae mutants to killing by N. elongata DNA.

| Ngo mutants | Clearance zone |
|---|---|
| WT | Yes |
| ΔpilE | No |
| ΔcomP | No |
| ΔcomP/comP$_{wt}$ | Yes |
| ΔpilT | No |

TABLE 9

Modifications in Ngo strain FA1090

| Modification system | Ngo FA1090 | SEQ ID NO: | Nucleotide modified | Detection method |
|---|---|---|---|---|
| NgoI | RG$^m$CGCY | 4 | Cytosine | PacBio SMRT |
| NgoII | GG$^m$CC | 5 | Cytosine | |
| NgoIII | $^m$CCGCGG | 6 | Cytosine | |
| NgoIV | G$^m$CCGGC | 7 | Cytosine | |
| NgoV | GGNN$^m$CC | 8 | Cytosine | |
| NgoAV | GC$^m$ANNNNNNNNTGC | 9 | Adenine | |
| NgoAXVII | G$^m$AGNNNNNTAC | 10 | Adenine | |
| NgoAXVI | GGTG$^m$A | 11 | Adenine | |
| NgoAX | CC$^m$ACC | 12 | Adenine | |
| NgoAXII | AGAA$^m$A | 13 | Adenine | Restriction analysis |

| | Ngo MS11 | | Nucleotide | Detection Method |
|---|---|---|---|---|
| NgoI | RG$^m$CGCY | 4 | Cytosine | Restriction analysis |
| NgoII | GG$^m$CC | 5 | Cytosine | |
| NgoIII | $^m$CCGCGG | 6 | Cytosine | |
| NgoIV | G$^m$CCGGC | 7 | Cytosine | |
| NgoV | GGNN$^m$CC | 8 | Cytosine | |
| NgoVIII | T$^m$CACC | 14 | Cytosine | |
| NgoAXVI | GGTG$^m$A | 11 | Adenine | PacBio SMRT |

R: A or G;
Y: C or T;
N: any base.

TABLE 10

Modifications[1] in E. coli K-12 strain

| Modification system | Ngo FA1090 | SEQ ID NO: | Nucleotide modified |
|---|---|---|---|
| EcoKI | A$^m$ACNNNNNNGTCG | 15 | Adenine |
| Dam | G$^m$ATC | 16 | Adenine |
| Dcm | C$^m$CWGG | 17 | Cytosine |

R: A or G;
W: A or T;
N: any base.
[1]The EcoKII/YhdJ system in K-12 is not expressed under laboratory conditions Example XIX This Example demonstrates that commensal DNA also kills N. meningitidis (Nme). Nme, the only other Neisseria species that is pathogenic to humans, is also genetically competent and takes up DNA in a DUS-dependent manner (Rotman and Seifert, 2014). IT was determined whether commensal Neisseria DNAs are able to kill Nme 8013 in the liquid assay. Nel, Nla, Nci, Nmu, Nsi and Npo DNAs, which have fewer putative DNA methyltransferases than Nme DNA, significantly reduced the viability of this pathogen (FIG. 15C, gray bars). Thus, the DNA methylation-based killing mechanism described for Ngo functions in Nme as well.

Example XX

This example describes a model for killing by commensal DNA. Commensals have been shown to inhibit the colonization of pathogens through protein-based killing mechanisms or outcompeting them for nutrients. The present disclosure provides evidence that commensal species of Neisseria kill pathogenic Neisseria based on genetic competence and DNA methylation state.

Commensal Neisseria elongata (Nel) kills pathogen Neisseria gonorrhoeae (Ngo) through DNA it releases into its surroundings. Ngo is a naturally competent organism that preferentially takes up DNA containing the Neisseria-specific DNA Uptake Sequence (DUS; 5'-GCCGTCTGAA-3' (SEQ ID NO:3)) (Elkins et al., J Bacteriol 173, 3911-3913 1991; Goodman and Scocca, Proc Natl Acad Sci USA 85, 6982-6986 1988; Graves et al., J Bacteriol 152, 1071-1077 1982). Ngo is killed when it takes up chromosomal DNA purified from Nel and other commensal Neisseria, and Ngo mutants defective in DNA uptake/transformation resist DNA killing. These findings indicate that DNA is toxic to Ngo, but only if it is taken up by the pathogen. Consistent with these in vitro findings, Nel accelerates the clearance of Ngo from the vagina of mice in a DNA uptake-dependent manner.

The Ngo genome is one of the most heavily methylated of bacterial genomes, encoding 14-19 predicted DNA methylases (Blow et al., 2016, supra; Roberts et al., 2015, supra; Stein et al., 1995, supra) (tools.neb.com/genomes/index.php?page=N). Nel DNA modified to partially mimic the Ngo methylation pattern kills the pathogen less efficiently than unmodified DNA. Conversely, DNA from Ngo TD3, which is deleted of 3 of its 7 restriction/modification loci, is more toxic to Ngo than WT Ngo DNA. Importantly, an Ngo sequence (ADIDA) with an E. coli methylation pattern kills the pathogen significantly more efficiently than the same sequence with the Ngo methylation signature. These findings indicate that the toxicity of DNA for Ngo is determined at least in part by differences in the methylation state of the incoming DNA and the host genome. They demonstrate that any DNA will kill Ngo, provided it is taken up by the pathogen, and its methylation state differs from that of the recipient cell.

The resistance of the Ngo recA mutant to the bactericidal effect of DNA provides a clue to the killing mechanism. In prokaryotes, RecA plays a central role in homologous recombination, binding to single stranded (ss) DNA to form pre-synaptic filaments, searching for sequences homologous to the ssDNA, and initiating synapse formation at regions of homology (Lee et al., Nucleic Acids Res 45, 11743-11751 2017; Renkawitz et al., Nat Rev Mol Cell Biol 15, 369-383 2014). *Neisseria* genomes have large regions of sequence homology; DNA taken up by Ngo recombines with their homologues in the chromosome in a RecA-dependent manner (Bennett et al., 2012, supra; Koomey and Falkow, 1987, supra; Koomey et al., 1987, supra; Marri et al., 2010, supra; Mehr and Seifert, Mol Microbiol 30, 697-710 1998).

Based on these and other observations, a model is provided for how Ngo is killed when it takes up commensal *Neisseria* DNA. The present invention is not limited to a particular model or mechanism of action of commensal DNA in killing target bacteria. Commensal DNA is converted to ss form as it enters the Ngo cytoplasm (Chaussee and Hill, J Bacteriol 180, 5117-5122 1998). RecA binds to the ssDNA and begins to form synaptic joints at homologous sites in the chromosome (Lee et al., 2017; Renkawitz et al., Nat Rev Mol Cell Biol 15, 369-383 2014). In these structures, the commensal DNA has a foreign signature. Restriction enzyme(s) cleave at cognate sequences in these duplexes, destroying chromosome integrity. Consistent with this model, all sources of toxic DNA used in this study have multiple recognition sites for Ngo MS11 restriction/modification enzymes (Table 11).

Many restriction enzymes are known to cleave hemimethylated DNA (Gruenbaum et al., Nature 292, 860-862 1981). During replication, newly synthesized DNA is temporarily unmodified. In Caulobacter, the process of methylating the new DNA strand takes ~50 minutes to complete (Stephens et al., Proc Natl Acad Sci USA 93, 1210-1214 1996). This indicates that synaptic joints in Ngo with mismatched methylation patterns may exist for some duration. Chromosome integrity is therefore likely to result from a race between DNA methylase and restriction enzyme activity at these synapses. It is also affected by how much DNA is taken into the cell, as multiple synapses formed by these DNA fragment may overwhelm DNA repair enzymes.

How much DNA Ngo takes up in a short period of time is not known. The highly competent Ngo expresses multiple Tfp, so it is possible that many if not all Tfps are capable of taking up DNA concurrently. Multiple segments of commensal *Neisseria* DNA entering Ngo therefore recombine at multiple homologous sites in the chromosome, making these sites sensitive to restriction cleavage.

The *E. coli* plasmid pCR-Blunt becomes toxic to Ngo when a DUS is inserted. An examination of pCR-Blunt revealed short stretches (10 to 17 bp) with 100% nucleotide sequence homology to >14000 sites throughout the pathogen genome (Table 12). Many of these microhomologies contain sequence motifs recognized by 6 of 7 restriction/modification systems in Ngo MS11 (Table 12). Sequence homology as short as 8 bp is sufficient to initiate RecA-mediated synapse formation (Qi et al., Cell 160, 856-869 2015). It is contemplated that once pCR-BLUNT(DUS) enters Ngo (enable by the DUS), the short tracts of microhomology serve as sites of synapse formation.

Ngo extrudes its DNA using Type IV Secretion System (T4SS) proteins AtlA and ParB, encoded in the Gonococcal Genetic Island (GGI) (Dillard and Seifert, Mol Microbiol 41, 263-277 2001; Ramsey et al., Front Microbiol 2, 61 2011). GGI and T4SS are in the commensal *Neisseria bacilliformis* (Pachulec et al., PLoS One 9, e109613 2014), but neither atlA nor parB are in 15 other commensal *Neisseria* tested (Dillard and Seifert, 2001, supra).

Commensal DNA is more likely released into the environment through autolysis. During growth, approximately 4% of Ngo cells autolyse each generation, releasing DNA into the medium (Kohler et al., J Bacteriol 189, 5421-5428 2007). Autolysis requires AmiC, a N-acetylmuramyl-L-alanine-amidase, and LtgA, a lytic transglycosylase. Commensal *Neisseria*, including Nel, encode orthologs of these enzymes (Table 15) (Garcia and Dillard, J Bacteriol 188, 7211-7221 2006; Hebeler and Young, J Bacteriol 122, 385-392 1975, 1976; Kohler et al., J Bacteriol 126, 1186-1193 2007). While the liquid assays indicate that relatively high concentrations of Nel DNA are required to kill Ngo, the SEM images show Nel and Ngo microcolonies physically contact each other. At these Nel-Ngo interfaces the concentration of extracellular DNA is likely to be very high. The mouse studies indicate that extracellular Nel DNA can reach a high enough local concentration to antagonize Ngo in vivo.

The available evidence indicates that Ngo is a weak pathogen. Only a subset of individuals exposed to Ngo becomes infected. The transmission rate of Ngo ranges from 20% (female to male) to 70% (male to a female) (Holmes et al., Am J Epidemiol 91, 170-174 1970; Lin et al., J Infect Dis 178, 1707-1712 1998). In human challenge studies, 30-90% of males inoculated with Ngo become infected (Cohen et al., J Infect Dis 169, 532-537 1994; Schmidt et al., Sex Transm Dis 28, 555-564 2001; Schneider et al., J Infect Dis 172, 180-185 1995). Host factors including genetics and sex affect susceptibility to Ngo infection (Densen, Clin Microbiol Rev 2 Suppl, S11-17 1989; Holmes et al., 1970, supra; Lin et al., 1998, supra). The experiments described herein indicate that microbiota composition and commensal *Neisseria* abundance also influences the risk for Ngo infection.

The DNA-based mechanism of tribal warfare presented here is also relevant to pathogen *Neisseria meningitidis* (Nme). Carriage of commensal *Neisseria* is inversely correlated with Nme carriage (Deasy et al., Clinical infectious diseases: an official publication of the Infectious Diseases Society of America 60, 1512-1520 2015; Diallo et al., J Infect 72, 667-677 2016). Specifically, commensal *Neisseria lactamica* (Nla) protects against Nme colonization of the nasopharynx (Cartwright et al., Epidemiol Infect 99, 591-601 1987; Deasy et al., 2015, supra; Evans et al., Clin Infect Dis 52, 70-77 2011). This protective effect was postulated to be due to the presence of cross-reactive antibodies to the pathogen (Oliver et al., 2002); however, natural bactericidal antibodies against Nme have been shown to predate Nla carriage (Trotter et al., Clin Vaccine Immunol 14, 863-868 2007). The observation that commensal *Neisseria* DNA also kills Nme indicates that commensal *Neisseria* residing in the nasopharynx may inhibit Nme colonization through the DNA-based killing mechanism described for Ngo.

Based on the data and model described herein, it is contemplated that Ngo and Nme DNA do not kill commensal *Neisseria*. Ngo and Nme DNA is more heavily methylated than commensal *Neisseria* DNA, and the growth of Nel, a genetically competent organism (Higashi et al., 2011, supra), is unaffected in the presence of Ngo. Several other pathogens are naturally competent for DNA transformation, among them *Bacteroides, Streptococcus pneumonia, Acine-* tobacter baylyi, Haemophilus influenzae, Helicobacter pylori, and Vibrio cholerae (Blokesch, Curr Biol 26, 3255 2016).

TABLE 11

Toxic DNA contains sequence recognized by Ngo MS11 R/M systems.

| R/M system | Recognition sequence | SEQ ID NO: | # occurrences Ne1 DNA | pCR-Blunt (DUS) | ADIDA |
|---|---|---|---|---|---|
| NgoI | RG$^m$CGCY | 4 | 514 | 3 | 2 |
| NgoII | GG$^m$CC | 5 | 16392 | 24 | 9 |
| NgoIII | $^m$CCGCGG | 6 | 420 | 0 | 0 |
| NgoIV | G$^m$CCGGC | 7 | 1592 | 3 | 4 |
| NgoV | GGNN$^m$CC | 8 | 2710 | 9 | 7 |
| NgoVIII | T$^m$CACC | 14 | 1582 | 3 | 2 |
| NgoAXVI | GGTG$^m$A | 11 | 1656 | 3 | 2 |

R: A or G;
Y: C or T;
N: any base.

TABLE 12

Short regions of homology (10-17 bp) between pCR-Blunt and Ngo chromosome contain recognition sequences from Ngo restriction modification (R/M) systems.

| R/M system | Recognition sequence | SEQ ID NO: | # of occurrences in NgO chromosome | Homology length (minimum) | Homology length (maximum) |
|---|---|---|---|---|---|
| NgoI | RG$^m$CGCY | 4 | 11 | 10 | 12 |
| NgoII | GG$^m$CC | 5 | 414 | 10 | 17 |
| NgoIII | $^m$CCGCGG | 6 | 0 | — | — |
| NgoIV | G$^m$CCGGC | 7 | 94 | 10 | 17 |
| NgoV | GGNN$^m$CC | 8 | 36 | 10 | 15 |
| NgoVIII | T$^m$CACC | 14 | 14 | 10 | 15 |
| NgoAXVI | GGTG$^m$A | 11 | 21 | 10 | 13 |

TABLE 15

Orthologs of N-acetylmuramyl-L-alanine-amidase AmiC and lytic transglycosylase LtgA in commensal Neisseria.

| | AmiC | | LtgA | |
|---|---|---|---|---|
| Neisseria species (strain) | Coverage (%) | Identity (%) | Coverage (%) | Identity (%) |
| N. elongata (ATCC 29315) | 99 | 56 | 99 | 61 |
| N. sicca (ATCC 29256) | 99 | 76 | 98 | 69 |
| N. mucosa (ATCC 25996) | 99 | 76 | 99 | 68 |
| N. subflava (NJ9703) | 100 | 75 | 98 | 71 |
| N. flavescens (NRL30031) | 86 | 79 | 98 | 71 |
| N. cinerea (ATCC 14685) | 100 | 94 | 99 | 88 |
| N. polysaccharea (ATCC 43768) | 100 | 95 | 100 | 96 |
| N. lactamica (ATCC 23970) | 100 | 97 | 100 | 97 |

Coverage and identity values were obtained by querying AmiC and LtgA amino acid sequences against the genome database using blastp at ncbi.

TABLE 7

Bacterial strains

| Organism | Strain and Genotype | Source |
|---|---|---|
| E. coli | DH5α dam$^+$, dcm$^+$ | Lab collection |
| Ngo | MS11 wt, P+, Opa-nonexpressing | (Segal et al., 1985) |
| Ngo ΔpilT | MS11 ΔpilT | (Dietrich, 2009) |
| Ngo ΔcomP | MS11 ΔcomP | This study |
| Ngo ΔcomP comP$_{wt}$ | MS11 ΔcomP comP$_{wt}$ | This study |
| Ngo TD3 | MS11 ΔNgoII ΔNgoIV ΔNgoV | This study |
| Ngo N400 | MS11 recA (tetM) | (Tonjum et. al., 1995) |
| Ngo i35A | MS11 AsiSI-DUS-iga-DUS-AsiSI (ADIDA) | This study |
| Nel | ATCC 29315 | (Marri et al., 2010) |
| N. lactamica | ATCC 23970 | (Marri et al., 2010) |
| N. cinereal | ATCC 14685 | (Marri et al., 2010) |
| N. mucosa | ATCC 25996 | (Marri et al., 2010) |
| N. sicca | ATCC 29256 | (Marri et al., 2010) |
| N. polysaccharea | ATCC 32768 | (Marri et al., 2010) |
| N. meningitidis | 8013 | (Nassif et al., 1993) |

TABLE 13

Sequence of DNA fragments.

| Primer | Sequence (5'-3') | Use |
|---|---|---|
| Iga5AD | CGGTTTGGGCGTGGATAC GCCTGACCACGCCGCGCCGATTACT TCGGGCGCACCGATTGGCGTACTGC ACGGCTTCCGCAGCTATCTGATCGA GGACGAAAACGGCCAAGTCTTGGGG ACGCACTCTGTTTCCGCAGGCTTGG ATTACCCCGGCATCGGCCCGGAACA CAGCCATCTGCACGACATCAAGCGC GTCGAATACACCGTTGCCAAAGATG ACGAAGCACTCGAAGCCTTTGACTT GCTCTGCCGATTCGAGGGCATCATC CCCGCGCTCGAATCCAGCCACGCCG TTGCTTGGGCGGTGAAAAACGCGCC GAAAATGGGTAAAGACCAAGTGATT TTGGTCAACCTGTCGGGTCGCGGCG ACAAAGACATCAATACCGTGGCGAA ACTCAAAGGCATTGAGCTGTAGCTT TGTTAGTCTGATAAAAATGCCGTCC GAAGCTTGAGTTCAGACGGCATTTT ATTTTGCTATGAATTTGGTATTGCG ATCGCATGCCGTCTGAATTAGAAAC GAATCTGTATTTTAATTTGTCCGGA TTTTTGTTTTTCCAATTGTTTTCCT TTTGTAATACTGCCATTTACGTTTA ATGTAACATTACGGTACAGTAACGC GGCGCCTGCTGAATATTGCTGTTGA TTATCTGCTTTATAGGCGAAGGATT TACCGCCCACATTCACGCCGCCTTT GCCATAATTGGCAAAGTAAGCTGCA GATAACAAGGGTTTTACGGTAAGGT | Introduction of AsiSI restriction site and DUS to 5' end of iga |

TABLE 13-continued

Sequence of DNA fragments.

| Primer | Sequence (5'-3') | Use |
|---|---|---|
|  | TGCCGACTTTAAACCGATAAGCAAA<br>ATCCAGTCCGCCGTTAGTGTTTTC<br>ACTGCCATAGAACTTACTTTAACAC<br>TGTCGTCACCCAACTTGTAATCTGC<br>AGATGACAGGCGGCTGTAACGGATA<br>CCCGCACTAGGGACAATCTCGAATT<br>GATTGATTTTCAGCGTATTGCCCAA<br>AGTAAGGCCGGTTTGGATGCTTGTT<br>CGGTTAAAGTTTGCTTTTTGCTGCG<br>TTTGTAACCGGCTTCTCAAGCTGCC<br>CGCACCA(SEQ ID NO: 18) |  |
| DAIga3 | TCGTGTTGTTTGATTTTATCTGCAA<br>ATTCTTTTTTATAGATATTCCATTC<br>TTGCCATGAAGACCCATTGATTTTT<br>TTGTTTGTCAAAAGCAAATAGTGGA<br>GAGCCGCTATCGCCCAACACGCCGT<br>AATTTGTTAACGCATCTTGCGAAAG<br>TGCTTGTTTAAGTTCTTCTGCCGAA<br>TACTGTTTATGTATTCATTGTTTGG<br>TCAATATTAATATCTTTATAAGGCG<br>TACCTGCAATGGCATAACGATAGGC<br>TTGTGAAAGATCGCGCAAATCGTAG<br>CCTTTTTCATTTCCTTCTTGATGAT<br>AAACCCCTTTTTCATAAACTAATTG<br>CCTGCCCGCACCGATTCTGACAAAA | Introduction of DUS and AsiSI restriction site to 3' end of iga |

TABLE 13-continued

Sequence of DNA fragments.

| Primer | Sequence (5'-3') | Use |
|---|---|---|
|  | GAGGAAAAACGGTTTTTATCTTTGT<br>AGGTATCCAATCCGCCGCCGGCATC<br>AGTTGGTGCAATCGGTGCCA<u>ATGCC<br>GTCTGAA</u>GCGATCGCCTTCGGTTAC<br>AAACTTATTAAAACGCGCCATATTA<br>TAATCTTCGAGGCGGCCTAAATTGC<br>TCGCACCCCAAGCTTTATGGGGTTC<br>ATAGTTATTTTGTTCGACAACGCGG<br>TATTCATTTTCTTTGTCGGCTACAT<br>CATTATGACCGTTGTATTGGCCGTA<br>ATAAAAGTATGGACTTCTGCTTTG<br>GCGTGTTTGACGCTGACGGCATATT<br>GGGGATCGACTACCGTTGCTATGCG<br>TTTGTTGACATCTGCAACGCTAAAA<br>TCAATCATCGGTACGTTGGATAATG<br>CGTTGCCGATGTTTTGACCTCGTTT<br>GTTTTTCACTGATAAATCGGTTGCG<br>CCGACAAAAAATTTGCCTTTGTTTT<br>CTGCAAAGTCACGGAATATTTGATA<br>ATCGACATCGTCTCTCACCAATGCC<br>GCTTCTGAGTATGGCGTAAGGGCAT<br>AGGCAAGAAAGATGGATAAGGATAT<br>GGCGTTAATTTTAAAACGTTTGGCT<br>TTCAT(SEQ ID NO: 19) |  |

AsiSI restriction site is in bold; DUS is underlined.

TABLE 14

Primers.

| Primer | Sequence (5'-3') | Use |
|---|---|---|
| comP_MS11_F | CGCCCGCACCAAAAGGCCCCGCCAAACCGGTG<br>CTGCCTGCGGTTAAAAAATAGAGTGGGAAATAT<br>GCATACTGCTGAATGGGATAGTAAGTCTGTTCA<br>AAGAAATATGTTGAATAATCTGTTCTTATTGGAA<br>GTAAAGTAATGACTGATAATCGGGGTTTCTCG<br>AGGGCTTGACACTTTATG (SEQ ID NO: 20) | Deletion of comP |
| comP_MS11_R | GATACGGATCACGGGTCATAACTATAGGCTTAA<br>TATTACACGATTCTCATTCCATCAAGGCGGAAAA<br>CCGCACAAATACTGAAACACTATCGATCGATTTG<br>TAAACAAGCCTACTTAAGTAACTTGCAGTCATCG<br>ATGTTTAAACTTCAGACGGC (SEQ ID NO: 21) | Deletion of comP |
| MR392 | CCGTCCATTTCGGTATTCAC (SEQ ID NO: 22) | Confirmation of comP deletion |
| MR395 | TTTTCGATTTCTTCGCTGTG (SEQ ID NO: 23) | Confirmation of comP deletion |
| MR396 | GTAAACATCAATGCGGCTTC (SEQ ID NO: 24) | Confirmation of comP insertion |
| 16SF | CTCGAAGCCTTTGACTTGCT (SEQ ID NO: 25) | Confirmation of comP insertion |
| NgoII_FC_F | CAAAATGCGCCAAATCAAC (SEQ ID NO: 26) | Deletion of ngoII; confirmation of ngoII deletion |
| NgoII_FC_R | GGGTTCAGTCCCAAGTTTGA (SEQ ID NO: 27) | Delete ngoII; confirmation of ngoII deletion |
| NgoIV_FC_F | GAAATCGCCGAACACGTTAT (SEQ ID NO: 28) | Deletion of ngoIV; confirmation of ngoIV deletion |
| NgoIV_FC_R | CCAATACGCCGACATAATCC (SEQ ID NO: 29) | Deletion of ngoIV; confirmation of ngoIV deletion |

TABLE 14-continued

Primers.

| Primer | Sequence (5'-3') | Use |
|---|---|---|
| NgoV_FC_F | TCGCGCACAATCAAAATATC (SEQ ID NO: 30) | Deletion of ngoV; confirmation of ngoV deletion |
| NgoV_FC_R | ACGCGTAAAAACTTCGGTTG (SEQ ID NO: 31) | Delete ngoV; confirmation of ngoV deletion |
| DUS_pCR-Blunt_F | ATGCCGTCTGAAGTACGGCA GTTTAAGGTTTACACC (SEQ ID NO: 32) | Addition of DUS to pCR-Blunt; PCR amplification of pCR-Blunt |
| pCR-Blunt_R | GTATAGGCTGCGCAACTGTT (SEQ ID NO: 33) | PCR amplification of pCR-Blunt |
| M13_F | TGTAAAACGACGGCCAGT (SEQ ID NO: 34) | Sequencing of pCR-Blunt and BAC clones/subclones |
| M13_R | CAGGAAACAGCTATGAC (SEQ ID NO: 35) | Sequencing of pCR-Blunt and BAC clones/subclones |
| Iga5_F | GCAGCTATCTGATGCAGGAC (SEQ ID NO: 36) | Sequencing of i35A; PCR amplification of ADIDA |
| Iga5_R | AGCTTGAGAAGCCGGTTACA (SEQ ID NO: 37) | Sequencing of i35A |
| Iga3_F | TTCCATTCTTGCCATGATTTT (SEQ ID NO: 38) | Sequencing of i35A |
| Iga3_R | TTCTTGCCTATGCCCTTACG (SEQ ID NO: 39) | Sequencing of i35A; PCR amplification of ADIDA |

Example XXI

This example describes killing of Ngo by Nel DNA in hydroxyethyl cellulose.

Ngo ($5 \times 10^5$ CFUs) were suspended in 150 ul of GC broth containing Kellogg's Supplements I and II and $MgSO_4$ (5 mM), and seeded into 24-well microplates (Corning). Purified Neisseria elongata (Nel) DNA was diluted in GCB containing 1% hydroxyethyl cellulose (HEC) to the desired concentration. One hundred microliters of DNA was added to the wells at the indicated concentrations. GCB-1% HEC without DNA was used as control. The plates were incubated for 4 h at 37° C., 5% $CO_2$. The bacteria were harvested with a P1000 pipette, and serially diluted in liquid GC broth. The serial dilutions were plated onto GCB agar containing Kellogg's Supplements I and II and the plates incubated overnight before colony forming units were counted.

Figure 21:
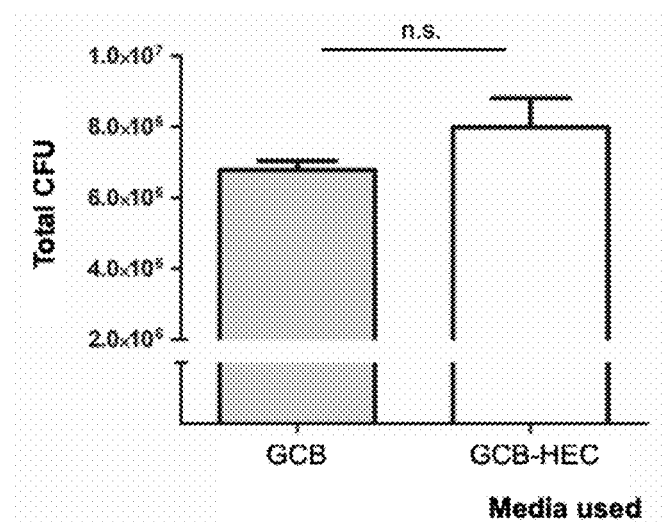
FIG. 21: Hydroxyethyl cellulose does not affect Ngo MS11 growth. Ngo MS11 was grown in GCB alone or GCB-HEC for 4 h. Bacteria were recovered after a 4 h of incubation and plated onto GCB agar to enumerate. n=3. Error bars: SEM. (n.s. not significant; un paired two-tailed t-test).

It was tested if Ngo is killed by Nel gDNA when it is suspended in hydroxyethyl cellulose (HEC). HEC was selected because it is thickening agent widely used in personal lubricants. First, the effect of HEC on Ngo MS11 growth was determined. Although Ngo MS11 grew slightly better in media containing HEC compared to just GCB, this difference is not significant. (FIG. 21).

Figure 22:
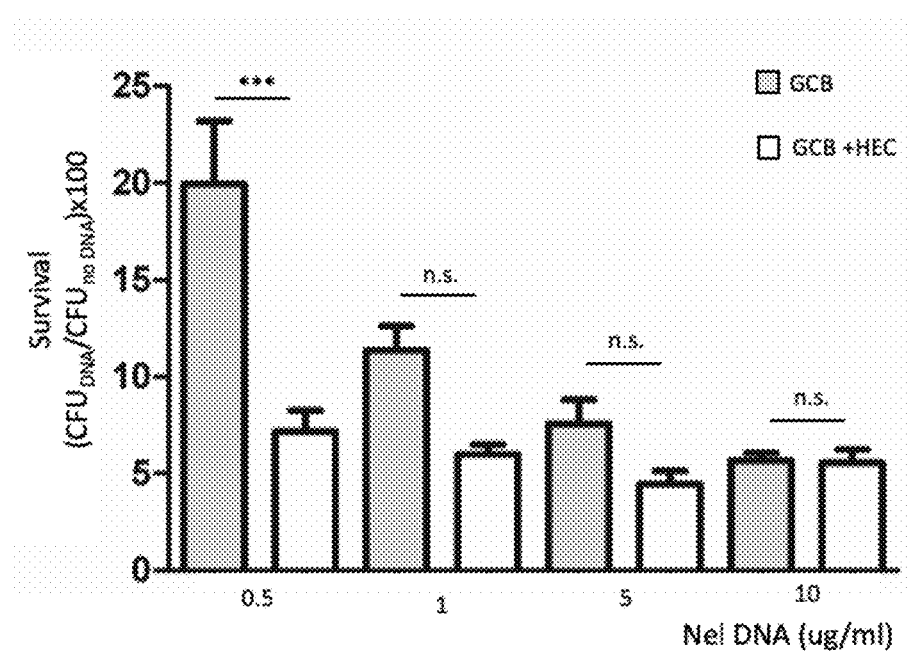
FIG. 22: Ngo MS11 is killed more effectively when Nel DNA is suspended in 1% hydroxyethyl cellulose. CFUs of Ngo recovered after a 4 h incubation with different concentrations of DNA in GCB (grey bars), or in GCB −1% hydroxyethyl cellulose (white bars). Survival is calculated as CFU of Ngo incubated with DNA normalized to CFU of Ngo incubated with buffer. n=3. Error bars: SEM. (***$P<0.0001$; n.s. not significant; One-way ANOVA with Tukey's Multiple Comparison Test)

Next, the sensitivity of Ngo to DNA killing in the presence of HEC was assayed. Ngo survival was dose dependent when the DNA was suspended in GCB. When HEC was used, less DNA (0.5 µg/ml of DNA in GCB-HEC vs 1 µg/ml of DNA in GCB) was needed to kill ~95% of Ngo (FIG. 22). This result indicates that HEC does not interfere with Ngo killing by DNA; instead HEC potentiates the DNA-mediated killing. The results demonstrated that Nel DNA acts as a microbicide.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes. The following references are referenced within this application and are herein incorporated by reference in all entireties:

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method of killing or inhibiting the growth of *Neisseria gonorrhoeae* (Ngo) comprising adding to the Ngo a composition comprising an effective amount of a first isolated or purified nucleic acid comprising one or more copies of a DNA uptake sequence(DUS) comprising SEQ ID NO: 2 or SEQ ID NO: 3 and a second isolated or purified nucleic acid possessing a pattern of methylation that is different from that of the Ngo, thereby killing or inhibiting the growth of the Ngo.

2. The method of claim 1, wherein the nucleic acid is a plasmid, a bacterial artificial chromosome, or a genomic DNA.

3. The method of claim 1, wherein said methylation is cytosine methylation in CpG dinucleotides and/or adenine methylation.

4. The method of claim 1, wherein said second nucleic acid is produced in a microorganism that possesses a methylation system that results in the pattern of methylation that is different from that of the Ngo.

5. The method of claim 4, wherein said microorganism is *E. coli*.

6. The method of claim 1, wherein said nucleic acid is 0.1 kb to 100 kb in length.

7. The method of claim 1, wherein said second nucleic acid comprises a portion of a gene or nucleic acid sequence specific to the Ngo and absent in human-dwelling commensal species of *Neisseria*.

8. The method of claim 7, wherein said portion is at least ten nucleotides.

9. The method of claim 7, wherein said gene is selected from the group consisting of tdfF, tdfH, and iga.

10. The method of claim 1, wherein the composition does not inhibit the growth of or kill a commensal species of *Neisseria*.

11. The method of claim 1, wherein said adding comprises topical delivery of the composition to a mucosal surface of an individual in need thereof.

12. The method of claim 11, wherein the composition is topically delivered as a vaginal gel.

* * * * *